(12) United States Patent
Matzke-Ogi et al.

(10) Patent No.: US 10,703,796 B2
(45) Date of Patent: Jul. 7, 2020

(54) CD44V6-DERIVED CYCLIC PEPTIDES FOR TREATING CANCERS AND ANGIOGENESIS RELATED DISEASES

(71) Applicant: AMCURE GMBH, Eggenstein-Leopoldshafen (DE)

(72) Inventors: Alexandra Matzke-Ogi, Eggenstein-Leopoldshafen (DE); Véronique Orian-Rousseau, Rittershofen (FR); Uwe Haberkorn, Schwetzingen (DE); Thomas Lindner, Eppelheim (DE); Walter Mier, Bensheim (DE)

(73) Assignees: AMCURE GMBH, Eggenstein-Leopoldshafen (DE); RUPRECHT-KARLS-UNIVERSITÄT, Heidelberg (DE)

( * ) Notice: Subject to any disclaimer, the term of this patent is extended or adjusted under 35 U.S.C. 154(b) by 0 days.

(21) Appl. No.: 15/532,817

(22) PCT Filed: Dec. 7, 2015

(86) PCT No.: PCT/EP2015/078892
§ 371 (c)(1),
(2) Date: Jun. 2, 2017

(87) PCT Pub. No.: WO2016/087680
PCT Pub. Date: Jun. 9, 2016

(65) Prior Publication Data
US 2017/0320930 A1 Nov. 9, 2017

(30) Foreign Application Priority Data
Dec. 5, 2014 (GB) .................... 1421647.7

(51) Int. Cl.
| | | |
|---|---|---|
| *C07K 14/705* | (2006.01) | |
| *A61K 38/17* | (2006.01) | |
| *A61P 35/00* | (2006.01) | |
| *A61K 9/00* | (2006.01) | |
| *A61K 45/06* | (2006.01) | |
| *A61K 38/00* | (2006.01) | |

(52) U.S. Cl.
CPC ...... *C07K 14/70585* (2013.01); *A61K 9/0019* (2013.01); *A61K 38/177* (2013.01); *A61K 45/06* (2013.01); *A61K 38/00* (2013.01)

(58) Field of Classification Search
None
See application file for complete search history.

(56) References Cited

U.S. PATENT DOCUMENTS 5,696,229 A 12/1997 Laurie et al.
2007/0032415 A1* 2/2007 Macina .................. C07H 21/04
435/6.14
2012/0045393 A1 2/2012 Linder et al.
2012/0115794 A1 5/2012 Matzke et al.
2012/0258998 A1 10/2012 Tan et al.

FOREIGN PATENT DOCUMENTS

| EP | 1258255 A1 | 11/2002 | |
|---|---|---|---|
| EP | 1391213 A1 | 2/2004 | |
| EP | 1417974 A1 | 5/2004 | |
| EP | 1647556 A1 * | 4/2006 | ....... C07K 14/70585 |
| EP | 2218457 A1 | 8/2010 | |
| EP | 2266593 A1 | 12/2010 | |
| JP | H05213996 | 8/1993 | |
| JP | 2002533299 A | 10/2002 | |
| JP | 2003089700 A | 3/2003 | |
| WO | 199716557 A1 | 5/1997 | |
| WO | 2000044771 A1 | 8/2000 | |
| WO | 2005065709 A2 | 7/2005 | |
| WO | 2007121147 A2 | 10/2007 | |
| WO | 2011022335 A1 | 2/2011 | |
| WO | WO 2014079914 A1 | 5/2014 | |
| WO | WO 2014079940 A1 | 5/2014 | |
| WO | WO 2014079943 A1 | 5/2014 | |
| WO | 2014173842 A1 | 10/2014 | |

OTHER PUBLICATIONS

Davies, "The Cyclization of Peptides and Depsipeptides," J. Pept. Sci. 9:471-501 (2003).*
International Search Report and Written Opinion in corresponding PCT Application No. PCT/EP2015/078892, dated Mar. 23, 2016.
"MCF-10 product literature from ThermoFischer Scientific" accessed Apr. 4, 2016 at URL thermofisher.com/us/en/home/technical-resources/cell-lines/m/cell-lines-detail-553 .html; 2 pgs.
Alexandra Matzke et al., "A Five-Amino-Acid Peptide Blocks Met- and Ron-Dependent Cell Migration," Cancer Research, Jul. 15, 2005, pp. 6105-6110.
Anonymous, Biotechnology/Life Sciences in Baden-Wurttemberg amcure GmbH is working on a new compound against pancreatic cancer, URL:http://www.bio-pro.de/medtech/biopharma/ <http://www.bio-pro.de/medtech/biopharma/> aktuelles/ index.htrnl?lang en&artikelid/artikel/08196/index.htrn, Jul. 2, 2012.
Breast Cancer Staging, American Joint Committee on Cancer, 7th ed., American Cancer Society, pp. 1-2 (2009).
Breast Cancer, Merck Manual, accessed Aug. 21, 2014 at merckmanuals. com/home/womens-health-issues/breast-disorders/; 20 pgs).
Britt Winkelmann, Kit-Innovation-Innovation Department- Shareholdings-amcure GmbH, URL:http://www.innovation.kit. edu/english/ shareholdings_679.php, (May 7, 2012).
Chen et al., "Expression of heparanase gene, CD44v6, MMP-7, and nm23 protein and their relationship with the invasion and metastasis of gastric carcinomas," World J. Gastroenterol. 10:776-782 (2004).

(Continued)

*Primary Examiner* — James H Alstrum-Acevedo
*Assistant Examiner* — Kristina M Hellman
(74) *Attorney, Agent, or Firm* — Fenwick & West LLP

(57) ABSTRACT

The present invention relates to compounds, pharmaceutical compositions and methods for treating different forms of cancer and angiogenesis related diseases using cyclic peptides.

Figure 2:
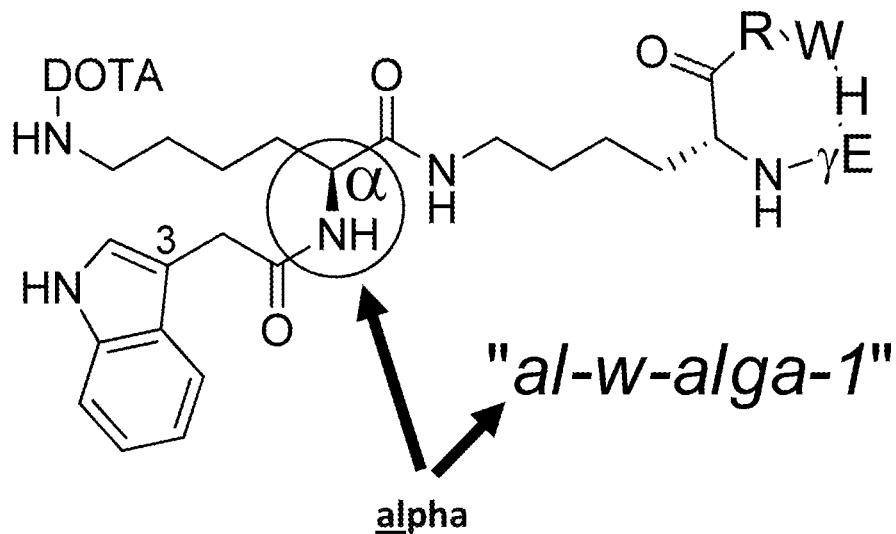

19 Claims, 22 Drawing Sheets
Specification includes a Sequence Listing.

(56) References Cited

OTHER PUBLICATIONS

Hoffman et al., CD44 Splice Variants Confer Metastatic Behaviour in Rats: Homologous Sequences are Expressed in Human Tumor Cell Linesl, Cancer Research, American Association for Cancer Research, vol. 51, No. 19, Oct. 1, 1991, pp. 5292-5297.

Hoffman M., et al., "CD44 Splice Variants Confer Metastatic Behaviour in Rats: Homologous Sequences are Expressed in Human Tumor Cell Linesl," Cancer Research, American Association for Cancer Research, vol. 51, No. 19, Oct. 1, 1991, pp. 5292-5297.

Holliday et al., "Choosing the right cell line for breast cancer research," Br. Can. Res. (2011) 13:215 pp. 1-7.

Kawano et al., "Evaluation of soluble adhesion molecules CD44 (CD44st, CD44v5, CD44v6), ICAM-1, and VCAM-1 as tumor markers in head and neck cancer," Amer. J. Otolnaryn. Head Neck Med. Surg. (2008) 25:308-313.

Livstone "Pancreatic Cancer,"Pancreatic Cancer—Gastrointestinal Disorders Merck Manual Professional Edition, (2016) pp. 1-5.

Matzke et al., A Five-Amino-Acid Peptide Blocks Met- and Ron-Dependent, Cancer Research Cell Migration, Jul. 15, 2005, pp. 6105-6110.

Orian-Rousseau et al., CD44, a therapeutic target for metastasizing tumours, European Journal of Cancer, Pergamon Press, Oxford, GB, vol. 46, No. 7, (May 1, 2010), pp. 1271-1277.

Reid et al., "Dual inhibition of ErbBl (EGFR/HERI) and ErbB2 (HER2/neu)," Eur. J. Cane. (2007). 43(3):481-489.

Ropponen et al., "Expression of CD44 and variant proteins in human colorectal cancer and its relevance for prognosis," Scand. J. Gastro. (1998) 33:301-309.

Rudy, W. et al.,"The Two Major CD44 Proteins Expressed on a Metastatic Rat Tumor Cell Line are Derived from Different." Cancer Research, vol. 53, pp. 1262-1268. Mar. 1993.

Stauder et al. "CD44 Variant Isoforms in Non-Hodgkin's Lymphona: A New Independent Prognostic Factor," Blood, vol. 85, No. 10, p. 2885-2899. May 1995.

Tempher et al., "Prognostic Value of Immunohistochemically Detected CD44 Isoforms CD44v5, CD44v6 and CD44v7-8 in Human Breast Cancer," Eur. J. Cane. (1996) 32A:2023-2025.

Tremmel et al., A CD44v6 peptide reveals a rold of CD44 in VEGFR-2 signaling and angiogenesis, Blood, vol. 114, No. 25, Sep. 22, 2009, pp. 5236-5244.

Vu et al., "Trastuxumab: updated mechanisms of action and resistance in breast cancer," Front. Oncol. 2:1-6 (Jun. 2012).

Wielenga, V. et al., "CD44 Glycoproteins in Colorectal Cancer: Expression, Function, and Prognostic Value," Adv Cancer Res, (2000) vol. 77, pp. 169-187.

Yamaguchi et al., "Expression of CD44v6 in advanced gastric cancer and its relationship to hematogenous metastasis and long-term prognosis," J. Surg. Oncol. 29:230-235 (2002).

Youngye et al., "Modeling of peptides containing D-amino acids: implications on cyclization", J. Comput. Aided Mol. Des. (2009) 23:677-689.

Zoller, CD44: Can a Cancer-Initiating Cell Profit from an Abundantly Expressed Molecule?, Nature Reviews Cancer, vol. 11, No. 4, (2011), pp. 254-267.

\* cited by examiner

Figure 1

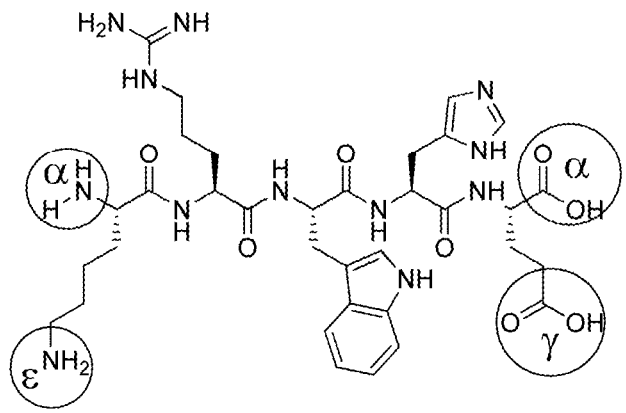

| Full name | abbreviation | sequence |
|---|---|---|
| [αKγE]cyCD44v6/3 | *alga-1* | cy[αKRWHEγ] |
| [εKγE]cyCD44v6/3 | *epga-1* | cy[εKRWHEγ] |
| [αKαE]cyCD44v6/4 | *alal-1* | cy[αKRWHEα] |
| [εKαE]cyCD44v6/4 | *epal-1* | cy[εKRWHEα] |
| [αKγE]cyCD44v6/4 | *alga-2* | cy[αKNRWHEγ] |
| [εKγE]cyCD44v6/4 | *epga-2* | cy[εKNRWHEγ] |
| [αKαE]cyCD44v6/5 | *alal-2* | cy[αKNRWHEα] |
| [εKαE]cyCD44v6/5 | *epal-2* | cy[εKNRWHEα] |
| [αKγE]cyCD44v6/5 | *alga-3* | cy[αKGNRWHEγ] |
| [εKγE]cyCD44v6/5 | *epga-3* | cy[εKGNRWHEγ] |
| [αKαE]cyCD44v6/6 | *alal-3* | cy[αKGNRWHEα] |
| [εKαE]cyCD44v6/6 | *epal-3* | cy[εKGNRWHEα] |
| DOTA-[αKγAbu]cyCD44v6/3 | *algaba-1* | DOTA-cy[αKRWHγAbu] |

Side chain derivatives

DOTA-sp[αKγE]cyCD44v6/3   *sp-alga-1*   DOTA-GGL-cy[αKRWHEγ]

Lys as linker & aromatic-hydrophobic modifications:

α or ε:     „f": phenyl acetic acid     „w": 3-indole acetic acid

Example:

alpha

| | |
|---|---|
| *al-f-alga-1* | (ε-DOTA- α-phenyl acetic acid)Lys-cy[αKRWHEγ] |
| *ep-f-alga-1* | (α-DOTA- ε- phenyl acetic acid)Lys-cy[αKRWHEγ] |
| *al-w-alga-1* | (ε-DOTA- α-indole acetic acid)Lys-cy[αKRWHEγ] |
| *ep-w-alga-1* | (α-DOTA- ε- indole acetic acid)Lys-cy[αKRWHEγ] |

Figure 3
A
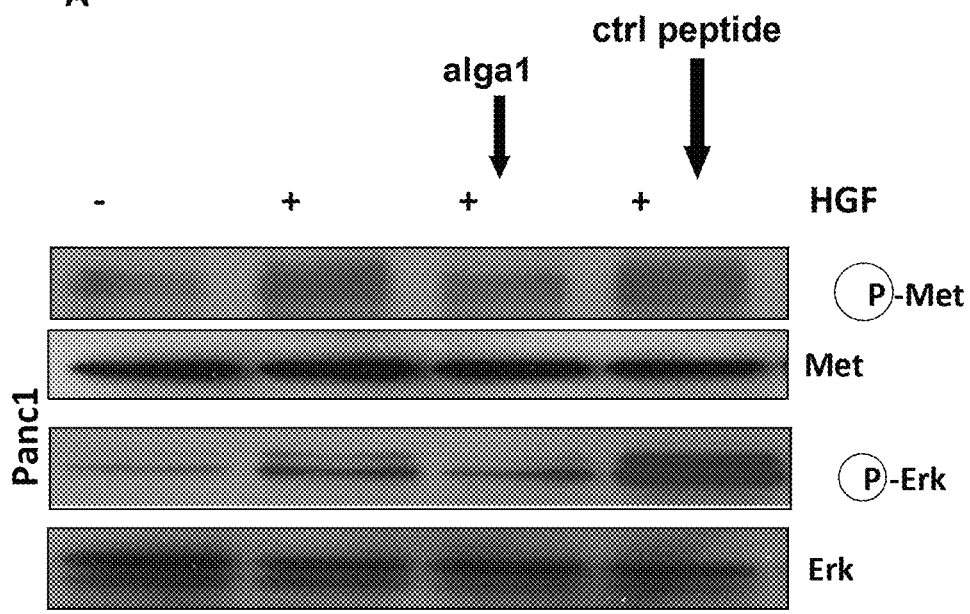
B
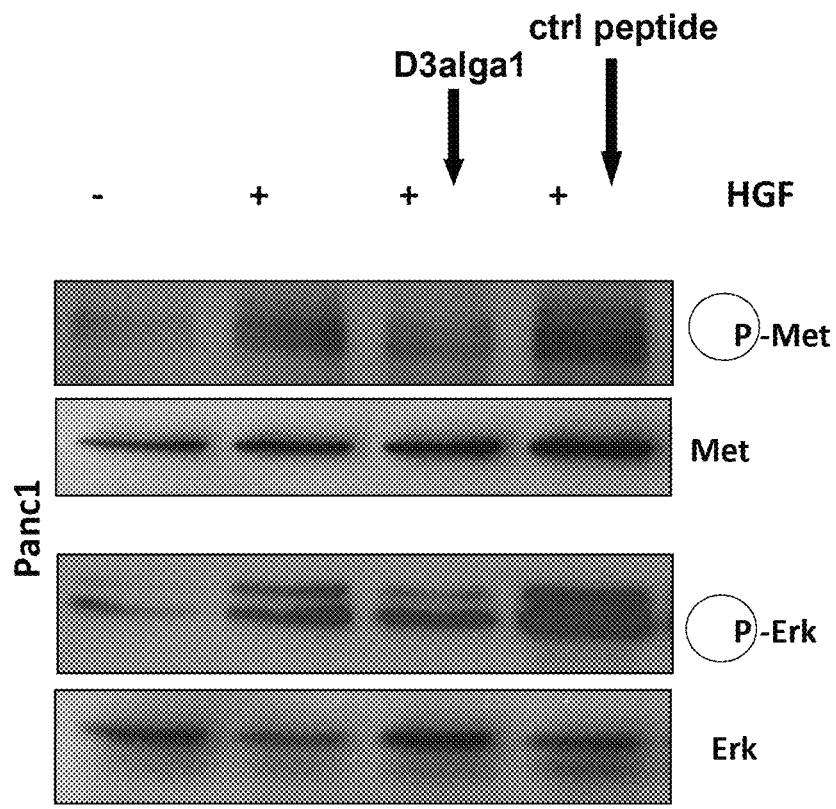

B

A

B

A

B

D3-alga1 (cy[αKRWHEγ])

D6-alga3 (cy[αKGNRWHEγ])

D2-epal1 (cy[εKRWHEα])

alga2 (cy[αKNRWHEγ])

Figure 13

Name: D2-epga-1; Sequence: [εKγE]cy(KrWHE)-OH

Name: D3-epga-1; Sequence: [εKγE]cy(KRwHE)-OH

Name: D4-epga-1; Sequence: [εKγE]cy(KRWhE)-OH

Name: D2-epal-1; Sequence: [εKαE]cy(KrWHE)

Name: D3-epal-1; Sequence: [εKαE]cy(KRwHE)

Name: D4-epal-1; Sequence: [εKαE]cy(KRWhE)

Name: D3-alga-2; Sequence: [αKγE]cy(KNrWHE)-OH

Name: D4-alga-2; Sequence: [αKγE]cy(KNRwHE)-OH

Name: D5-alga-2; Sequence: [αKγE]cy(KNRWhE)-OH

Name: D4-alga-3; Sequence: [αKγE]cy(KGNrWHE)-OH

Name: D5-alga-3; Sequence: [αKγE]cy(KGNRwHE)-OH

Name: D6-alga-3; Sequence: [αKγE]cy(KGNRWhE)-OH

Figure 14

Name: epga-1; Sequence: [εKγE]cy(KRWHE)-OH

Name: epal-1; Sequence: [εKαE]cy(KRWHE)

Name: alga-2; Sequence: [αKγE]cy(KNRWHE)-OH

Name: alga-3; Sequence: [αKγE]cy(KGNRWHE)-OH

US 10,703,796 B2

CD44V6-DERIVED CYCLIC PEPTIDES FOR TREATING CANCERS AND ANGIOGENESIS RELATED DISEASES

CROSS-REFERENCE TO RELATED PATENT APPLICATIONS

This is a U.S. National Phase Application under 35 U.S.C. § 371 of International Patent Application No. PCT/EP2015/078892, filed Dec. 7, 2015, and claims priority to GB Great Britain Application No. 1421647.7, filed Dec. 5, 2014, which are incorporated by reference in their entireties. The International Application was published on Jun. 9, 2016, as International Publication No. WO 2016/087680 A1.

SEQUENCE LISTING

The instant application contains a Sequence Listing which has been filed electronically in ASCII format and is hereby incorporated by reference in its entirety. Said ASCII copy, created on Jun. 14, 2019, is named 146998_00201_SL.txt and is 34,315 bytes in size.

TECHNICAL FIELD OF THE INVENTION

The present invention relates to compounds, pharmaceutical compositions and methods for treating forms of cancer and angiogenesis related diseases.

BACKGROUND OF THE INVENTION

Different types of cancer have been shown to involve at least in part over activation of receptor-tyrosine-kinases such as cMET, and VEGFR. Cancers include e.g. colorectal cancer, breast cancer, liver cancer and pancreatic cancer. DB:SL CD44 has been discussed as having a role in e.g. HGF and VEGF dependent activation of receptor-tyrosine-kinases such cMET, RON and VEGFR (see inter alia, Ponta et al., *Nature Reviews* (2003), 4, 33-45 and Tremmel et al., *Blood* (2009), 25, 5236-5244) which activate downstream MAP kinases like Erk. Further, expression of an alternatively spliced form of CD44, namely CD44v6 has been shown to occur in some of the cancers being characterized by over-activation of receptor-tyrosine-kinases. Peptides, which are able to block CD44v6 mediated activation of receptor-tyrosine-kinases have been discussed as being potentially useful in treatment of such cancers.

However, there is a continuing interest for pharmaceutically active agents that allow treatment of such cancers.

For example, treatment of pancreatic cancer typically depends on the stage of the cancer. Although only localized cancer is considered suitable for surgery with curative intent at present, only about 20% of cases are diagnosed with localized disease. Surgery can also be performed for palliation, if the malignancy is invading or compressing the duodenum or colon. Further treatment options include radiation and palliative chemotherapy. At present chemotherapy includes treatment with gemcitabine or combination therapies with gemcitabine such as gemcitabine/oxaliplatin or gemcitabine/cisplatin. Despite intensive research efforts, no treatment is currently available which would be considered to provide a long-term progression-free survival. Pancreatic cancer is therefore to date one of the malignancies with the worst prognosis of all neoplasias. Particularly if metastases have spread across the body such as to the liver, the peritoneal cavity and the lungs, no efficient treatment is available, which would allow to effectively regression of existing metastases.

Similar problems exist for other cancers, which have already formed metastases. For many of these cancers, palliative chemotherapy may be the only therapeutic option.

Angiogenesis denotes the formation of new blood vessels from already existing vessels. Although angiogenesis is in general a normal process in growth and development, it plays an essential role in malignant tumors since new blood vessels are required to provide the growing tumor with nutrients and oxygen. Tumors induce angiogenesis by secreting various growth factors, such as bFGF and VEGF which induce capillary growth into the tumor. Therefore, anti-angiogenesis reagents have gained increasing importance in cancer treatment.

Thus, there is a need for new compounds and methods which can be used to treat cancers such as pancreatic and liver cancers, before metastasis and when metastatic spreading has already occurred. It is further desirable that these compounds act as anti-angiogenesis agents to prevent the formation of new blood vessels which could provide the tumor with nutrients.

OBJECTIVE AND SUMMARY OF THE INVENTION

It is one objective of the present invention to provide compounds, and pharmaceutical compositions comprising such compounds, useful as medicament and in the treatment of cancer, and angiogenesis related diseases, diseases from the field of ophthalmology, diseases associated with an increased invasive potential of cells, and inflammatory disorders, in particular cancer and angiogenesis related diseases, in a human being before and after metastatic spreading. Another objective is to provide new methods for treating cancer in a human being before and after metastatic spreading and for treating angiogenesis related diseases.

These and other objectives as they will become apparent from the ensuing description are attained by the subject-matter of the independent claims. Some of the preferred embodiments of the present invention are mentioned in the dependent claims.

The present invention, to some extent, is based on the experimental data described hereinafter showing that the cyclic peptides described herein are able to block activation of cMET and Erk. Based on this, these peptides also inhibit/reduce metastasis and lead to a regression of metastases. CD44v6 has also been implicated for other cancers such as Hodgkin lymphoma, colorectal cancer, cervical cancer, head and neck cancer, gastric cancer and breast cancer, probably due to its role in HGF dependent activation of receptor-tyrosine-kinases such cMET, RON and VEGFR.

The experiments described hereinafter further show that a compound comprising a cyclic peptide having as a minimal requirement the peptide sequence R-W-H, an amino acid $X_1$, and further $X_{11}$, both being selected from the group comprising consisting of A, C, D, E, F, G, H, I, K, L, M, N, P, Q, R, S, T, V, W, or and Y is capable of blocking the formation of metastases in an animal model of human cancer.

As already mentioned above, it has been found that the peptides described herein are efficient for inhibiting metastasis if the tri-peptide sequence R-W-H is embedded in a cyclic peptide. Surprisingly, the cyclic peptides show a high pharmacological effectiveness as demonstrated in the experiments presented herein. The high pharmacological activity was surprising since cyclic peptides are characterized by a comparably rigid structure in the circle in comparison to non-cyclic peptides. Due to this, it would have been expected that the less flexible cyclic peptides interact less efficiently with the receptors. However, the opposite was found to be the case as shown in the experimental section below. Without intention to be bound by a particular theory, it is also believed that the cyclic structure of the claimed peptides reduces the peptides' susceptibility for proteolytic degradation. Thereby, the amount of peptide in the blood is increased so that more active peptide is available for interaction with the receptor. This leads to a higher overall pharmacological effect.

There are two further features which were found to additionally improve the pharmacological usefulness of the cyclic peptides and are therefore currently particularly preferred embodiments of the present invention. These two features improve the pharmacological activity of the claimed cyclic peptides preferably alone or—even more preferred—in combination.

Firstly, the cyclic peptides preferably comprise at least one chemical bond between a first and a second amino acid, in particular two adjacent amino acids, of the peptide which is not a chemical bond between the N-terminus of the first amino acid and the C-terminus of the second amino acid of the two amino acids, in particular of the two adjacent amino acids.

Hence, it is preferred that the circle or ring of the cyclic peptide not solely comprises chemical bonds between the N-terminal amino groups and the C-terminal carboxyl groups of the amino acids in the circle but e.g. between an N-terminal amino group and an amino acid side chain, preferably the carboxyl group of an amino acid side chain, a C-terminal carboxyl group and an amino acid side chain, preferably an amino group of an amino acid side chain, or between (at least) two amino acid side chains. Preferably one of said amino acid side chains bears a carboxyl group whereas the other amino acid side chain bears an amino group. Thus, it is preferred that the chemical bond between two adjacent amino acids involves the amino acid side chain of at least one of said two adjacent amino acids. Usually, cyclic peptides only comprise classical peptide bonds, i.e. all amino acids which participate in the circle of the cyclic peptide are connected via the C-terminal carboxyl group of one amino acid and the N-terminal amino group of a next or adjacent amino acid. However, according to the present invention it is particularly preferred that at least one chemical bond between two adjacent amino acids in the circle is not a classical peptide bond. It is particularly preferred that the chemical bond between the two adjacent amino acids involves the amino acid side chain of one of these adjacent amino acids. Such chemical bond forms the cyclic peptide structure via at least one amino acid side chain of one amino acid in the peptide circle. These chemical bonds are assumed to positively influence the pharmacological activity in two ways: (i) this kind of bond is not found in proteins or peptides in nature so that—again—standard proteases are not active on these chemical bonds and moieties. Hence, proteolytic cleavage is reduced. (ii) These chemical bonds which preferably involve at least one amino acid side chain seem to enhance the flexibility of the rigid structure of the cyclic peptides in comparison to cyclic peptides having only classical peptide bonds within the ring structure. This increases the number of conformations accessible for ligand interaction and may consequently lead to an improved binding of the cyclic peptide to the receptor in comparison to cyclic peptides solely with chemical bonds between the N- and C-terminus of the amino acids in the circle. However, the increased pharmacological activity of the cyclic peptides having such a chemical bond was surprising since these chemical bonds which are not the standard peptide bonds further differentiate the peptide from the natural peptide which binds to the receptor. Hence, preferably the cyclic peptides include at least one chemical bond between two adjacent amino acids which involves the amino acid side chain of at least one of two adjacent amino acids. In other words, at least one chemical bond between two adjacent amino acids is not formed between the N-terminal amino group of one of the two adjacent amino acids and the C-terminal carboxyl group of the other amino acid of the two adjacent amino acids. Preferably, the cyclic peptide comprises a chemical bond between two adjacent amino acids selected from the group consisting of a chemical bond between an N-terminal amino group of an amino acid and an amino acid side chain, a chemical bond between a C-terminal carboxyl group of an amino acid and an amino acid side chain, and a chemical bond between an amino acid side chain of a first amino acid of the peptide and an amino acid side chain of a second amino acid of the peptide.

Alternatively or additionally, it is highly preferred that the cyclic peptides include at least one D-amino acid. It is believed that the presence of at least one D-amino acid in the cyclic peptides further reduces the peptide's susceptibility to proteolytic cleavage since proteases are not evolutionary designed to act on D-amino acid containing proteins or peptides. This is in particular confirmed by the experimental data presented herein below. However, also with respect to this feature, the pharmacological inhibitory effect was absolutely surprising since the presence of D-amino acids further differentiates the peptide from the natural peptide which binds to the receptor. Thereby, the amount of peptide which is available for an interaction with the receptor is increased. In particular, the cyclic pentapeptide K-R-W-H-E having a D-amino acid W (D3alga1) (SEQ ID NO: 41) has been shown to be effective for inhibiting CD44v6-mediated activation of Met signaling. Hence, D-amino acids do not diminish the inhibitory effect of the peptides. In fact, D3alga1 even shows a higher inhibitory effect in the wound healing assay the results of which are presented in the Examples and FIG. 5. A "D-amino acid" is a term well understood by the skilled person. Usually, all of the amino acids derived from natural proteins are of the L configuration. D-amino acids are also found in nature, especially as components of certain peptide antibiotics, in walls of certain microorganisms and to some extent also in mammals including *Homo sapiens*. The L and D convention for amino acid configuration does not refer to the optical activity of the amino acid itself but rather to the optical activity of the isomer of glyceraldehyde from which that amino acid can, in theory, be synthesized (D-glyceraldehyde is dextrorotatory; L-glyceraldehyde is levorotatory).

In a particularly preferred embodiment, the cyclic peptide comprises a chemical bond between two adjacent amino acids of the peptide which is not a chemical bond between the N-terminus of the first amino acid and the C-terminus of the second amino acid of the two adjacent amino acids, preferably the chemical bond between the two adjacent amino acids involves the amino acid side chain of at least one of said two adjacent amino acids, and at least one D-amino acid. The experimental data presented herein below demonstrates impressively that the combination of these two features in the cyclic peptide leads to an even more increased pharmacological activity which was clearly unexpected and surprising since these cyclic peptides differ in many aspects from the natural peptide which binds to the receptor.

Figure 9:
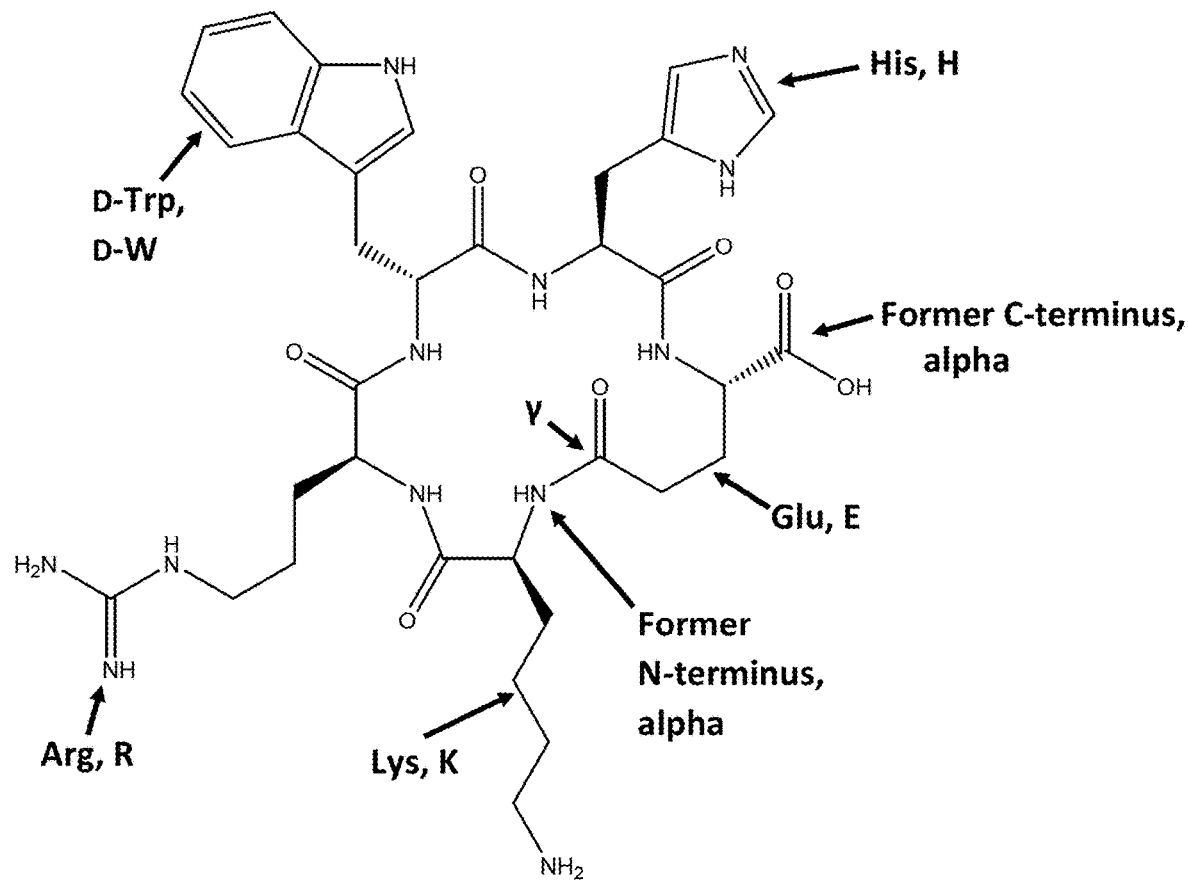

In a currently most preferred embodiment, the compound comprises the amino acid sequence K-R-W-H-E (SEQ ID No.: 41), a chemical bond between the N-terminal amino group of K and the carboxyl group of the amino acid side chain of E, and wherein W is a D-amino acid (D3alga1, cf. FIG. 9).

Figure 12:
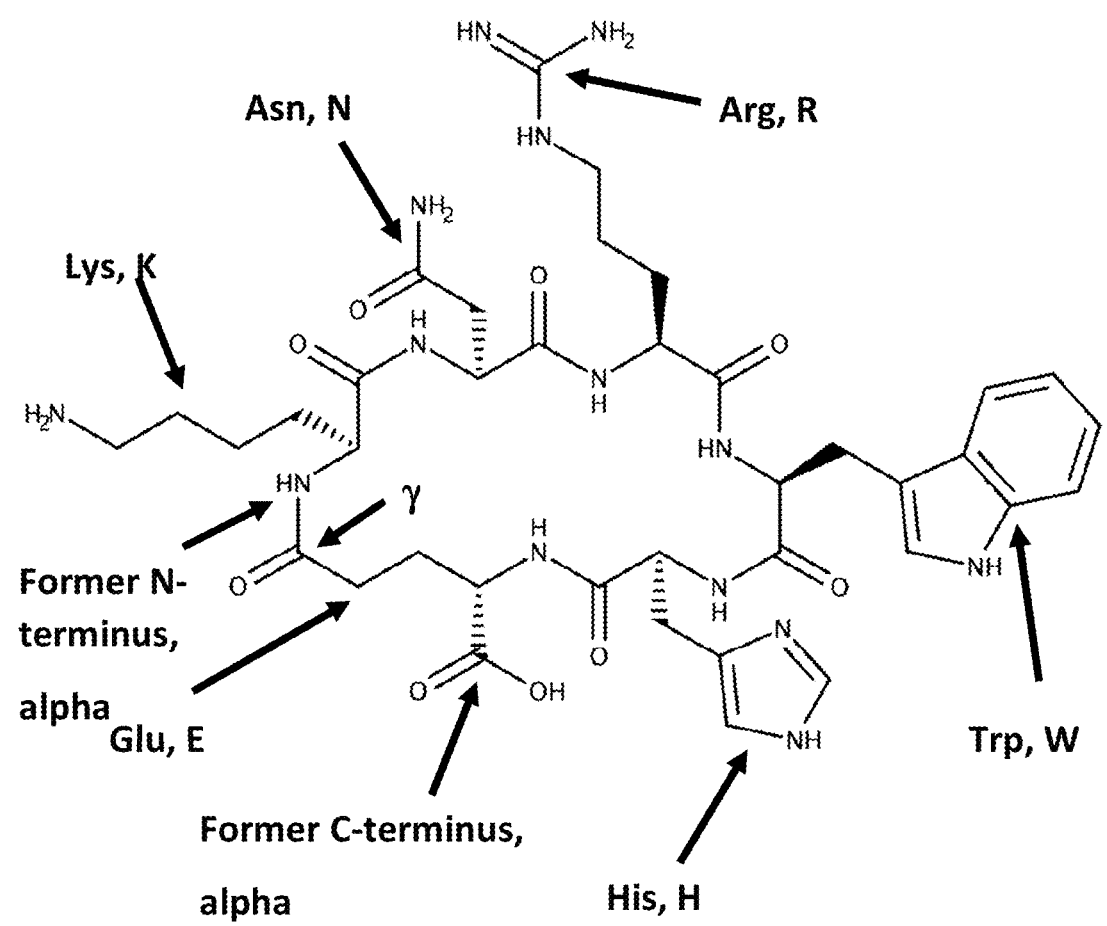

In another currently most preferred embodiment, the compound comprises a peptide which comprises the amino acid sequence as depicted in SEQ ID No.: 35 and comprises a chemical bond between an N-terminal amino group of K, and the carboxyl group of the amino acid side chain of E, such as alga-2 (FIG. 12).

Figure 10:
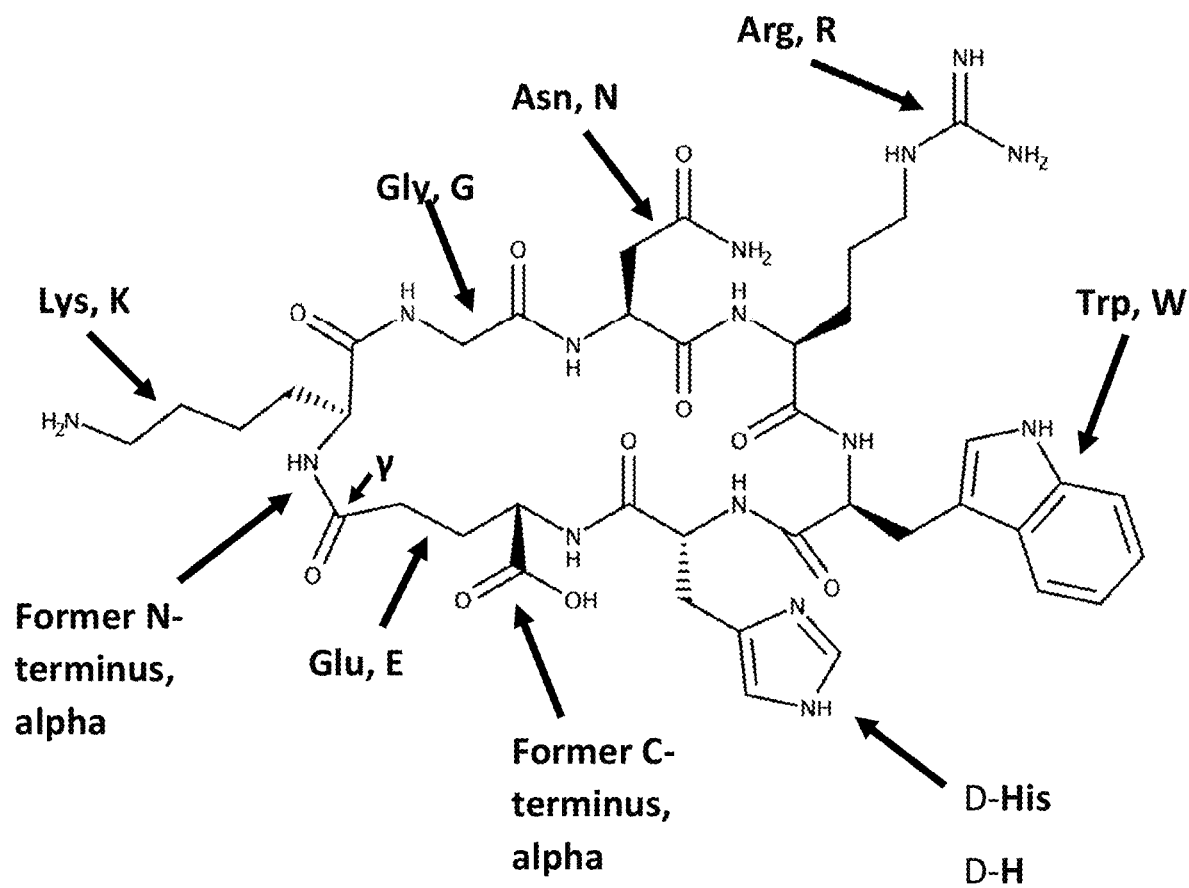

Currently most preferred is a compound of the invention, wherein the peptide comprises the amino acid sequence as depicted in SEQ ID No.: 36 and comprises a chemical bond between the N-terminal amino group of the amino acid K, and the carboxyl group of the amino acid side chain of the amino acid E, wherein the amino acid H is a D-amino acid, such as D6-alga-3 (cf. FIG. 10).

Figure 11:
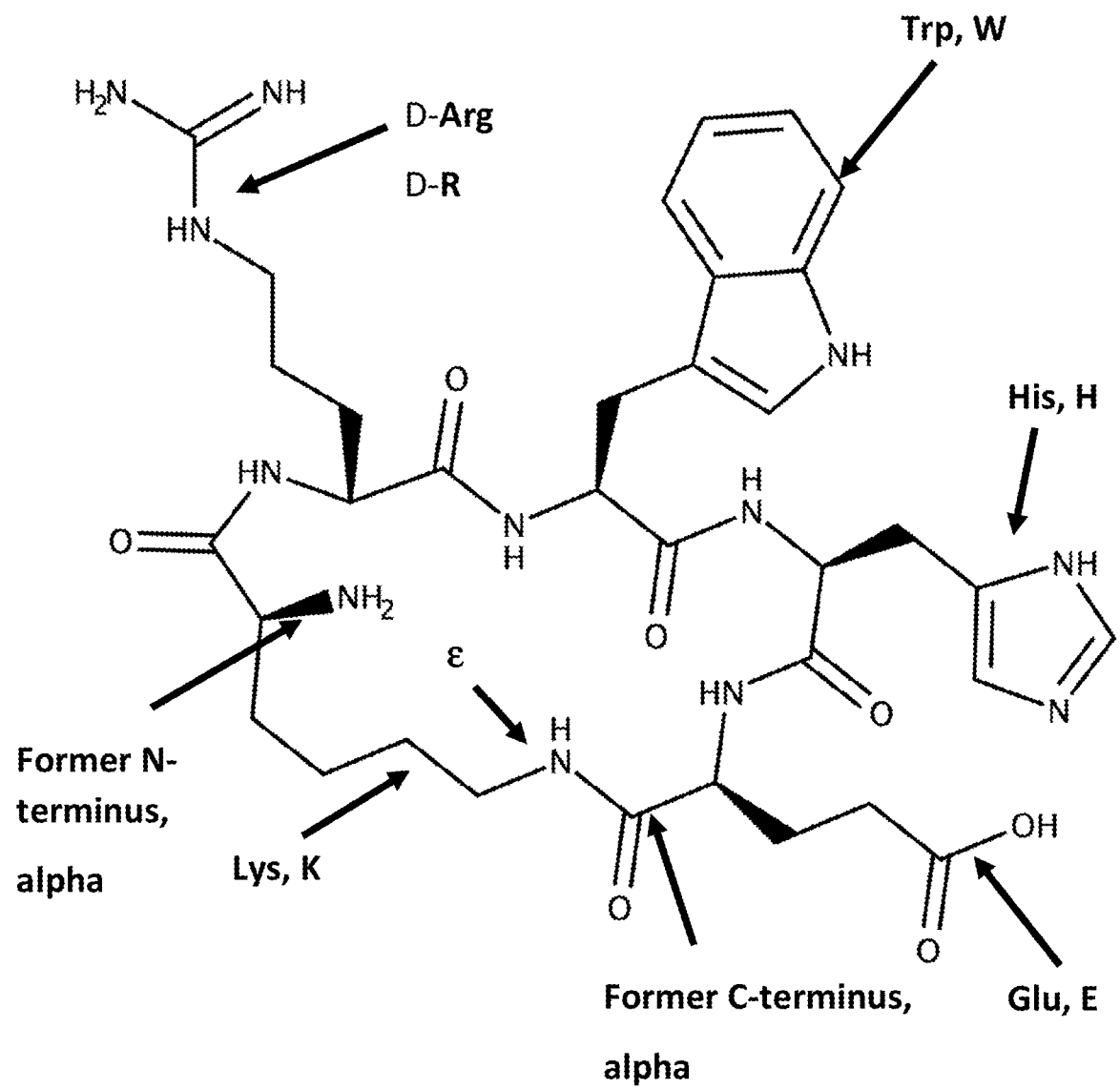

Currently most preferred is a compound of the invention, wherein the peptide comprises the amino acid sequence K-R-W-H-E (SEQ ID No.: 42) and comprises a chemical bond between the amino group of the amino acid side chain of the amino acid K, and the C-terminal carboxyl group of the amino acid E, wherein the amino acid R is a D-amino acid, such as D2-epal-1 (cf. FIG. 11).

Thus, the present invention relates to a compound comprising:
a cyclic peptide comprising at least
  (a) an amino acid $X_1$ being selected from the group consisting of A, C, D, E, F, G, H, I, K, L, M, N, P, Q, R, S, T, V, W, and Y, further
  (b) an amino acid sequence R-W-H, and further
  (c) an amino acid $X_{11}$ being selected from the group consisting of A, C, D, E, F, G, H, I, K, L, M, N, P, Q, R, S, T, V, W, and Y, or a peptidomimetic thereof,
  or
a cyclic peptide comprising at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein the amino acid $X_1$ is selected from the group consisting of A, C, D, E, F, G, H, I, K, L, M, N, P, Q, R, S, T, V, W, and Y, wherein the amino acids $X_2$, $X_3$, $X_4$, $X_5$, $X_6$, $X_7$, $X_{11}$, $X_{12}$, $X_{13}$, and $X_{14}$ are independently selected from the group consisting of A, C, D, E, F, G, H, I, K, L, M, N, P, Q, R, S, T, V, W, and Y, and wherein $X_2$, $X_3$, $X_4$, $X_5$, $X_6$, $X_7$, $X_{12}$, $X_{13}$, and $X_{14}$ are optionally present in the amino acid sequence, or a peptidomimetic thereof.

Preferred, the present invention relates to a compound comprising:
a cyclic peptide comprising at least
  (a) an amino acid $X_1$ being selected from the group consisting of A, C, D, E, F, G, H, I, K, L, M, N, P, Q, R, S, T, V, W, and Y, further
  (b) an amino acid sequence R-W-H, and further
  (c) an amino acid $X_{11}$ being selected from the group consisting of A, C, D, E, F, G, H, I, K, L, M, N, P, Q, R, S, T, V, W, and Y, or a peptidomimetic thereof,
  or
a cyclic peptide comprising at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein the amino acid $X_1$ is selected from the group consisting of A, C, D, E, F, G, H, I, K, L, M, N, P, Q, R, S, T, V, W, and Y, wherein the amino acids $X_2$, $X_3$, $X_4$, $X_5$, $X_6$, $X_7$, $X_{11}$, $X_{12}$, $X_{13}$, and $X_{14}$ are independently selected from the group consisting of A, C, D, E, F, G, H, I, K, L, M, N, P, Q, R, S, T, V, W, and Y, and wherein $X_2$, $X_3$, $X_4$, $X_5$, $X_6$, $X_7$, $X_{12}$, $X_{13}$, and $X_{14}$ are optionally present in the amino acid sequence, or a peptidomimetic thereof the compound comprising a chemical bond between two adjacent amino acids of the cyclic peptide which is not a chemical bond between the N-terminus of a first amino acid and the C-terminus of a second amino acid of the two adjacent amino acids.

Preferably, the present invention relates to a compound comprising:
a cyclic peptide comprising at least
  (a) an amino acid $X_1$ being selected from the group consisting of A, C, D, E, F, G, H, I, K, L, M, N, P, Q, R, S, T, V, W, and Y, further
  (b) an amino acid sequence R-W-H, and further
  (c) an amino acid $X_{11}$ being selected from the group consisting of A, C, D, E, F, G, H, I, K, L, M, N, P, Q, R, S, T, V, W, and Y, or a peptidomimetic thereof,
  or
a cyclic peptide comprising at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein the amino acid $X_1$ is selected from the group consisting of A, C, D, E, F, G, H, I, K, L, M, N, P, Q, R, S, T, V, W, and Y, wherein the amino acids $X_2$, $X_3$, $X_4$, $X_5$, $X_6$, $X_7$, $X_{11}$, $X_{12}$, $X_{13}$, and $X_{14}$ are independently selected from the group consisting of A, C, D, E, F, G, H, I, K, L, M, N, P, Q, R, S, T, V, W, and Y, and wherein $X_2$, $X_3$, $X_4$, $X_5$, $X_6$, $X_7$, $X_{12}$, $X_{13}$, and $X_{14}$ are optionally present in the amino acid sequence, or a peptidomimetic thereof, comprising a chemical bond between an amino acid side chain of a first amino acid and a member selected from the group consisting of the C-terminus, the N-terminus and the amino acid side chain of a second or a second adjacent amino acid.

Optionally, in the compound of the present invention, the amino acid $X_1$ is an amino acid having an $NH_2$ group in the amino acid side chain, such as K, R, N, or Q, $X_2$ is optionally present and optionally selected from the group consisting of amino acids with negatively charged side chains such as E or D, or amino acids with non-polar side chains such as A, V, L or I, $X_3$ is optionally present and optionally selected from the group consisting of amino acids with an $NH_2$ group in the amino acid side chain, such as K, R, N, or Q, and amino acids with non-polar side chains such as A, V, L or I, $X_4$ is optionally present and optionally selected from the group consisting of amino acids with non-polar or non-charged side changes and aromatic ring structures such as F, W, or Y, and amino acids with non-polar side chains such as A, V, L or I, $X_5$ is optionally present and optionally selected from the group consisting of amino acids with non-polar or non-charged side changes and aromatic rings structures such as F, W, or Y, and amino acids with non-polar side chains such as A, V, L or I, $X_6$ is optionally present and optionally selected from the group consisting of G and amino acids with non-polar side chains such as A, V, L or I, $X_7$ is optionally present and optionally selected from the group consisting of amino acids with an $NH_2$ group in the amino acid side chain, such as K, R, N, or Q, and amino acids with non-polar side chains such as A, V, L or I, $X_{11}$ is selected from the group consisting of amino acids with negatively charged side chains such as E or D, and amino acids with non-polar side chains such as A, V, L or I, $X_{12}$ is optionally present and optionally selected from the group consisting of G and amino acids with non-polar side chains such as A, V, L or I, $X_{13}$ is optionally present and optionally selected from the group consisting of amino acids with non-polar or non-charged side chains and aromatic rings structures such F, W, or Y, and amino acids with non-polar side chains such as A, V, L or I, and $X_{14}$ is optionally present and optionally selected from the group consisting of amino acids with an $NH_2$ group in the amino acid side chain, such as K, R, N, or Q, and amino acids with non-polar side chains such as A, V, L or I.

In another embodiment, in the compound of the invention, $X_1$ is selected from the group consisting of K, R, N, and Q, $X_2$ is optionally present and optionally selected from the group consisting of amino acids E and D, $X_3$ is optionally present and optionally selected from the group consisting of amino acids K, R, N, and Q, $X_4$ is optionally present and optionally selected from the group consisting of amino acids F, W, and Y, $X_5$ is optionally present and optionally selected from the group consisting of amino acids F, W, and Y, $X_6$ is optionally present and optionally selected from the group consisting of amino acids G, A, V, L and I, $X_7$ is optionally present and optionally selected from the group consisting of amino acids K, R, N, and Q, $X_{11}$ is present and optionally E or D, $X_{12}$ is optionally present and optionally selected from the group consisting of amino acids G, A, V, L and I, $X_{13}$ is optionally present and optionally selected from the group consisting of amino acids F, W, and Y, and $X_{14}$ is optionally present and optionally selected from the group consisting of amino acids K, R, N, and Q.

In another preferred embodiment, in the compound of the invention the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is optionally present and optionally selected from the group consisting of amino acids E and D, wherein $X_3$ is optionally present and optionally selected from the group consisting of amino acids K, R, N, and Q, wherein $X_4$ is optionally present and optionally selected from the group consisting of amino acids F, W, and Y, wherein $X_5$ is optionally present and optionally selected from the group consisting of amino acids F, W, and Y, wherein $X_6$ is optionally present and optionally selected from the group consisting of amino acids G, A, V, L and I, wherein $X_7$ is present and optionally selected from the group consisting of amino acids K, R, N, and Q, wherein $X_{11}$ is present and E or D, wherein $X_{12}$ is optionally present and optionally selected from the group consisting of amino acids G, A, V, L and I, wherein $X_{13}$ is optionally present and optionally selected from the group consisting of amino acids F, W, and Y, and wherein $X_{14}$ is optionally present and optionally selected from the group consisting of amino acids K, R, N, and Q, or a peptidomimetic thereof.

In another preferred embodiment, in the compound of the invention the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is optionally present and optionally selected from the group consisting of amino acids E and D, wherein $X_3$ is optionally present and optionally selected from the group consisting of amino acids K, R, N, and Q, wherein $X_4$ is optionally present and optionally selected from the group consisting of amino acids F, W, and Y, wherein $X_5$ is present and optionally selected from the group consisting of amino acids F, W, and Y, wherein $X_6$ is present and optionally selected from the group consisting of amino acids G, A, V, L and I, wherein $X_7$ is present and optionally selected from the group consisting of amino acids K, R, N, and Q, wherein $X_{11}$ is present and E or D, wherein $X_{12}$ is optionally present and optionally selected from the group consisting of amino acids G, A, V, L and I, wherein $X_{13}$ is optionally present and optionally selected from the group consisting of amino acids F, W, and Y, and wherein $X_{14}$ is optionally present and optionally selected from the group consisting of amino acids K, R, N, and Q, or a peptidomimetic thereof.

In another preferred embodiment, in the compound of the invention the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is optionally present and optionally selected from the group consisting of amino acids E and D, wherein $X_3$ is optionally present and optionally selected from the group consisting of amino acids K, R, N, and Q, wherein $X_4$ is present and optionally selected from the group consisting of amino acids F, W, and Y, wherein $X_5$ is present and optionally selected from the group consisting of amino acids F, W, and Y, wherein $X_6$ is present and optionally selected from the group consisting of amino acids G, A, V, L and I, wherein $X_7$ is present and optionally selected from the group consisting of amino acids K, R, N, and Q, wherein $X_{11}$ is present and optionally E or D, wherein $X_{12}$ is optionally present and optionally selected from the group consisting of amino acids G, A, V, L and I, wherein $X_{13}$ is optionally present and optionally selected from the group consisting of amino acids F, W, and Y, and wherein $X_{14}$ is optionally present and optionally selected from the group consisting of amino acids K, R, N, and Q, or a peptidomimetic thereof.

In another preferred embodiment, in the compound of the invention the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is optionally present and optionally selected from the group consisting of amino acids E and D, wherein $X_3$ is present and optionally selected from the group consisting of amino acids K, R, N, and Q, wherein $X_4$ is present and optionally selected from the group consisting of amino acids F, W, and Y, wherein $X_5$ present and is optionally selected from the group consisting of amino acids F, W, and Y, wherein $X_6$ is present and optionally selected from the group consisting of amino acids G, A, V, L and I, wherein $X_7$ is selected from the group consisting of amino acids K, R, N, and Q, wherein $X_{11}$ is present and optionally E or D, wherein $X_{12}$ is optionally present and optionally selected from the group consisting of amino acids G, A, V, L and I, wherein $X_{13}$ is optionally present and optionally selected from the group consisting of amino acids F, W, and Y, and wherein $X_{14}$ is optionally present and optionally selected from the group consisting of amino acids K, R, N, and Q, or a peptidomimetic thereof.

In another preferred embodiment, in the compound of the invention the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is present and optionally selected from the group consisting of amino acids E and D, wherein $X_3$ is present and optionally selected from the group consisting of amino acids K, R, N, and Q, wherein $X_4$ is present and optionally selected from the group consisting of amino acids F, W, and Y, wherein $X_5$ is present and is optionally selected from the group consisting of amino acids F, W, and Y, wherein $X_6$ is present and optionally selected from the group consisting of amino acids G, A, V, L and I, wherein $X_7$ is present and optionally selected from the group consisting of amino acids K, R, N, and Q, wherein $X_{11}$ is present and optionally E or D, wherein $X_{12}$ is optionally present and optionally selected from the group consisting of amino acids G, A, V, L and I, wherein $X_{13}$ is optionally present and optionally selected from the group consisting of amino acids F, W, and Y, and wherein $X_{14}$ is optionally present and optionally selected from the group consisting of amino acids K, R, N, and Q, or a peptidomimetic thereof.

In another preferred embodiment, in the compound of the invention the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is present and optionally selected from the group consisting of amino acids E and D, wherein $X_3$ is present and is optionally selected from the group consisting of amino acids K, R, N, and Q, wherein $X_4$ is present and is optionally selected from the group consisting of amino acids F, W, and Y, wherein $X_5$ is present and optionally selected from the group consisting of amino acids F, W, and Y, wherein $X_6$ is present and is optionally selected from the group consisting of amino acids G, A, V, L and I, wherein $X_7$ is present and optionally selected from the group consisting of amino acids K, R, N, and Q, wherein $X_{11}$ is optionally E or D, wherein $X_{12}$ is present and optionally selected from the group consisting of amino acids G, A, V, L and I, wherein $X_{13}$ is optionally present and optionally selected from the group consisting of amino acids F, W, and Y, and wherein $X_{14}$ is optionally present and optionally selected from the group consisting of amino acids K, R, N, and Q, or a peptidomimetic thereof.

In another preferred embodiment, in the compound of the invention the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is present and optionally selected from the group consisting of amino acids E and D, wherein $X_3$ is present and is optionally selected from the group consisting of amino acids K, R, N, and Q, wherein $X_4$ is present and optionally selected from the group consisting of amino acids F, W, and Y, wherein $X_5$ is present and optionally selected from the group consisting of amino acids F, W, and Y, wherein $X_6$ is present and optionally selected from the group consisting of amino acids G, A, V, L and I, wherein $X_7$ is present and optionally selected from the group consisting of amino acids K, R, N, and Q, wherein $X_{11}$ is present and optionally E or D, wherein $X_{12}$ is present and optionally selected from the group consisting of amino acids G, A, V, L and I, wherein $X_{13}$ is present and optionally selected from the group consisting of amino acids F, W, and Y, and wherein $X_{14}$ is optionally present and optionally selected from the group consisting of amino acids K, R, N, and Q, or a peptidomimetic thereof.

In a preferred embodiment, in the compound of the invention the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is present and optionally selected from the group consisting of K, R, N, and Q, preferably K, wherein $X_2$ is present and optionally selected from the group consisting of amino acids E and D, wherein $X_3$ is present and is optionally selected from the group consisting of amino acids K, R, N, and Q, wherein $X_4$ is present and optionally selected from the group consisting of amino acids F, W, and Y, wherein $X_5$ is present and optionally selected from the group consisting of amino acids F, W, and Y, wherein $X_6$ is present and optionally selected from the group consisting of amino acids G, A, V, L and I, wherein $X_7$ is present and optionally selected from the group consisting of amino acids K, R, N, and Q, wherein $X_{11}$ is present and optionally E or D, wherein $X_{12}$ is present and optionally selected from the group consisting of amino acids G, A, V, L and I, wherein $X_{13}$ is present and optionally selected from the group consisting of amino acids F, W, and Y, and wherein $X_{14}$ is present and is optionally selected from the group consisting of amino acids K, R, N, and Q, or a peptidomimetic thereof.

In a more preferred embodiment, in the compound of the invention $X_1$ is selected from the group consisting of K, R, N, and Q, preferably K, $X_2$, if present, is selected from the group consisting of amino acids E and D, $X_3$, if present, is selected from the group consisting of amino acids K, R, N, and Q, $X_4$, if present, is selected from the group consisting of amino acids F, W, and Y, $X_5$, if present, is selected from the group consisting of amino acids F, W, and Y, $X_6$, if present, is selected from the group consisting of amino acids G, A, V, L and I, $X_7$, if present, is selected from the group consisting of amino acids K, R, N, and Q, $X_{11}$ is D or E, $X_{12}$, if present, is selected from the group consisting of amino acids G, A, V, L and I, $X_{13}$, if present, is selected from the group consisting of amino acids F, W, and Y, and $X_{14}$, if present, is selected from the group consisting of amino acids K, R, N, and Q.

In an even more preferred embodiment of the invention, $X_1$ is K, $X_2$, if present, is E, $X_3$, if present, is Q, $X_4$, if present, is W, $X_5$, if present, is F, $X_6$, if present, is G, $X_7$, if present, is N, $X_{11}$ is E, $X_{12}$, if present, is G, $X_{13}$, if present, is Y, and $X_{14}$, if present, is R.

In a particularly preferred embodiment of the invention, the compound comprises a cyclic peptide which comprises at least the amino acid sequence $X_1$-$X_6$-$X_7$-R-W-H-$X_{11}$, wherein the amino acid $X_1$ is selected from the group consisting of the amino acids K, R, N, or Q, preferably $X_1$ is the amino acid K, wherein the amino acid $X_6$ is optionally present and selected from the group consisting of amino acids G, A, V, L and I, preferably $X_6$ is the amino acid G, wherein $X_7$ is optionally present and selected from a group consisting of amino acids K, R, N, and Q, preferably $X_7$ is N, and wherein $X_{11}$ is the amino acid D or E, preferably $X_{11}$ is the amino acid E, or a peptidomimetic thereof, the compound comprising a chemical bond between two adjacent amino acids of the cyclic peptide which is not a chemical bond between the N-terminus of a first amino acid and the C-terminus of a second amino acid of the two adjacent amino acids or the cyclic peptide comprising a chemical bond selected from the group consisting of a chemical bond between an N-terminal amino group of an amino acid and an amino acid side chain, a chemical bond between a C-terminal carboxyl group of an amino acid and an amino acid side chain, and a chemical bond between an amino acid side chain of a first amino acid of the cyclic peptide and an amino acid side chain of a second amino acid of the cyclic peptide.

In another very preferred embodiment, the cyclic peptide comprises, optionally consists of, the amino acid sequence K-R-W-H-E (SEQ ID No.: 34), K-N-R-W-H-E (SEQ ID No.: 35), K-G-N-R-W-H-E (SEQ ID No: 36), or a peptidomimetic thereof. Further preferably, the peptide of the invention does not comprise the amino acid sequence N-R-W-H-E (SEQ ID No.: 2), the amino acid sequence K-R-W-H-E (SEQ ID NO: 34) and a DOTA modification, the amino acid sequence K-G-N-R-W-H-E-G (SEQ ID NO: 18), the amino acid sequence K-E-Q-W-F-G-N-R-W-H-E-G-Y-R (SEQ ID No.: 6), or a 6mer or a peptidomimetic thereof.

Optionally, the cyclic peptide or peptidomimetic thereof comprises a modification. Optionally, the modification comprises an amino acid, amino acid derivative, a lipophilic modification or an aromatic hydrophobic modification, optionally the modification comprises phenyl acetic acid or 3-indole acetic acid. Examples of lipophilic modifications are fatty acids, isoprenoids, sterols, phospholipids, fatty acylation, attachment of a glycosyl phosphatidylinositol (GPI) anchor or attachment of palmitate, myristoylation, isoprenylation or prenylation, such as with farnesyl or geranylgeranyl moieties. In a preferred embodiment, the modification is not DOTA or a myristoyl group. The modification may be attached to the circle/ring of the peptide or to an amino acid side chain. It is further possible to modify the amino acid side chain or amino acid side chains which are involved in the circle/ring of the cyclic peptide. In particular, an amino acid side chain which is involved in the circle of the cyclic peptide, i.e. is—after ring/circle formation—a part of the circle, may be modified and/or truncated. "Modified" is to be understood according to its general meaning in the field of protein chemistry and denotes the chemical amendment by another chemical moiety. By a modification an additional chemical group is covalently attached to the respective part of the peptide. The position of the modification of the peptide is not limited. Further, more than one modification can be present at the peptide or even an amino acid side chain.

"Truncated" means that the amino acid side chain can be shortened in respect to the natural side chain of the amino acid.

In a particularly preferred embodiment, the compound of the invention comprises a chemical bond between two adjacent amino acids of the peptide which is not a chemical bond between the N-terminus of the first amino acid and the C-terminus of the second amino acid of the two adjacent amino acids.

"Adjacent" in the sense of the present invention denotes that the amino acids are located next to each other, in particular after formation of the circle of the cyclic peptide. Hence, the term adjacent includes that the two amino acids are next to each other when the circle of the cyclic peptide is closed. A first amino acid can be adjacent on the N-terminal or C-terminal side of a second amino acid. However, it is preferred that the chemical bond between at least two adjacent amino acids is not a peptide bond but e.g. involves at least the amino acid side chain of now of the two adjacent amino acids. In a preferred embodiment, the chemical bond which is not a chemical bond between the N-terminus of the first amino acid and the C-terminus of the second amino acid of the two adjacent amino acids forms the circle of the cyclic peptide. Hence, in a preferred embodiment said first and said second amino acid are the N-terminal and C-terminal amino acids of the peptide, respectively, before the circle of the cyclic peptide is formed. After forming the circle of the cyclic peptide, said first and second amino acids are adjacent to each other. More preferably, the chemical bond between the two adjacent amino acids involves the amino acid side chain of at least one of said two adjacent amino acids. Before the peptide is made cyclic, the first of the two adjacent amino acids is on the N-terminal side of the central RWH amino acid sequence motif and the second adjacent amino acid is on the C-terminal side of this central sequence motif. The numbers of amino acids which are present between the two adjacent amino acids and the central sequence motif RWH is variable on the N- or C-terminal side of the RWH motif and further explained hereinbelow. "Involves" in connection with the chemical bond between the two adjacent amino acids under participation of at least one amino acid side chain denotes that at least one atom of the amino acid side chain participates in a covalent bond which is localized between the two adjacent amino acids in the formed circle of the cyclic peptide. From the context it also becomes clear that the term "chemical bond" does not mean that there is necessarily only a single chemical bond between the two adjacent amino acids. In general, the term "chemical bond" is to be understood according to its meaning in the art of chemistry and is preferably a covalent atom bond. The chemical bond in the context of how the circle of the peptide is formed refers to the chemical bond which in fact connects the two amino acids: this can be the chemical bond between the N-terminal amino group of a first amino acid and the amino acid side chain of a second amino acid of the circle, the chemical bond between a C-terminal carboxyl group of a first amino acid and an amino acid side chain of a second amino acid, or the chemical bond between an amino acid side chain of a first amino acid of the peptide and an amino acid side chain of a second amino acid of the peptide. Hence the chemical bond described herein forms the circle so that the two amino acids which are denoted as "adjacent amino acids" become adjacent. A cyclic peptide of the invention can also comprise more than one chemical bond between two adjacent amino acids of the cyclic peptide which is not a chemical bond between the N-terminus of a first amino acid and the C-terminus of a second amino acid of the two adjacent amino acids In a preferred embodiment, the cyclic peptide comprises a chemical bond selected from the group consisting of a chemical bond between an N-terminal amino group of an amino acid and an amino acid side chain, a chemical bond between a C-terminal carboxyl group of an amino acid and an amino acid side chain, and a chemical bond between an amino acid side chain of a first amino acid of the peptide and an amino acid side chain of a second amino acid of the peptide.

As discussed, preferred is a chemical bond between the amino group of the N-terminus (alpha) and the carboxyl group of amino acid side chain (beta position in case of amino acid D and gamma position in case of amino acid E). Also preferred is the chemical bond between an amino group of an amino acid side chain and the carboxyl group of the C-terminus. Greek letters are used to denote the atoms of the amino acid and also the amino acid side chains, which are involved in the chemical bond between the amino acids that form the circle, such as the two adjacent amino acids, wherein the first atom of the side chain is denoted as alpha, the second beta, the third gamma, the fourth delta, the fifth epsilon and so forth. The "circle" or "ring" of the peptide is the ring or circle formed from the peptide backbone, and if applicable, the amino acid side chain or side chains or one or more $CH_2$ groups which participate(s) in the chemical bond which forms the ring or circle of the peptide. This is illustrated in FIG. 9. As cyclisation step in general the last chemical reaction is meant which leads to the chemical bond which finally closes the ring/circle. "In the circle" includes all atoms which participate in forming the circle. These can be the peptide backbone and one or more amino acid side chains or one or more $CH_2$ groups. The term does generally not include amino acid side chains which are not linked to another amino acid or another amino acid side chain of the peptide in a way that they participate in the circle but are attached to the peptide backbone as usual in naturally occurring peptides and proteins.

The high biological activity of cyclic peptides having a chemical bond between the N- or C-terminus and an amino acid side chain is proven by the compounds which are tested in the Examples, such as given in FIGS. 1, 2 and 9 to 14. Particularly, a chemical bond employing the amino group of the N-terminus and the carboxyl group of the amino acids E and D is preferred for circle formation. Cyclic peptides comprising at least one chemical bond in the circle which is not between the N- and C-terminus but either between the C- or the N-terminus of a first amino acid and the amino acid side chain of a second amino acid or between two amino acid side chains are preferred. As already explained above, the good pharmacological activity was surprising since these peptides of the invention differ significantly in their structure from the natural peptide which binds to the receptor. It is assumed that the reason for this is that the peptides are on the one hand particularly stable and less susceptible to proteolytic cleavage and on the other hand do not have the comparably rigid peptide backbone structure but are supposed to interact more flexibly and effectively with the receptor than a cyclic peptide, wherein all amino acids are connected via standard peptide bonds.

In a more preferred embodiment, the cyclic peptide comprises a chemical bond selected from the group consisting of a chemical bond between an N-terminal amino group of an amino acid and a carboxyl group of an amino acid side chain, preferably of E or D, a chemical bond between a C-terminal carboxyl group of an amino acid and an amino group of an amino acid side chain, preferably of K, R, N or Q, and a chemical bond between an amino group of an amino acid side chain of a first amino acid of the peptide, preferably of K, R, N or Q, and a carboxyl group of an amino acid side chain of a second amino acid of the peptide, preferably of E or D. Alternatively, the cyclic peptide of the compound of the invention comprises a chemical bond selected from the group consisting of a chemical bond between an N-terminal amino group of an amino acid and an amino acid side chain, a chemical bond between a C-terminal carboxyl group of an amino acid and an amino acid side chain, and a chemical bond between an amino acid side chain of a first amino acid of the two adjacent amino acids of the cyclic peptide and an amino acid side chain of a second amino acid of the two adjacent amino acids of the peptide. Alternatively, the cyclic peptide comprises a chemical bond selected from the group consisting of a chemical bond between an N-terminal amino group of a first amino acid and a carboxyl group of an amino acid side chain of a second amino acid, preferably being E or D, a chemical bond between a C-terminal carboxyl group of a first amino acid and an amino group of an amino acid side chain of a second amino acid, preferably being K, R, N or Q, and a chemical bond between an amino group of an amino acid side chain of a first amino acid of the cyclic peptide, preferably being K, R, N or Q, and a carboxyl group of an amino acid side chain of a second amino acid of the cyclic peptide, preferably being E or D.

In a particularly preferred embodiment, the peptide has the amino acid sequence K-R-W-H-E (SEQ ID No.: 34), K-N-R-W-H-E (SEQ ID No.: 35) or K-G-N-R-W-H-E (SEQ ID NO.: 36), and comprises a chemical bond selected from the group consisting of a chemical bond between an N-terminal amino group of an amino acid and an amino acid side chain, optionally a carboxyl group of an amino acid side chain, a chemical bond between a C-terminal carboxyl group of an amino acid and an amino acid side chain, optionally an amino group of an amino acid side chain, and a chemical bond between an amino acid side chain of a first amino acid of the peptide and an amino acid side chain of a second amino acid of the peptide, optionally between a carboxyl group of the amino acid side chain of the first amino acid and an amino group of the amino acid side chain of the second amino acid.

In a particularly preferred embodiment, the peptide has the amino acid sequence K-R-W-H-E (SEQ ID No.: 34), K-N-R-W-H-E (SEQ ID No.: 35) or K-G-N-R-W-H-E (SEQ ID NO.: 36), and comprises a chemical bond selected from the group consisting of a chemical bond between an N-terminal amino group of an amino acid and an amino acid side chain, optionally a carboxyl group of an amino acid side chain, a chemical bond between a C-terminal carboxyl group of an amino acid and an amino acid side chain, optionally an amino group of an amino acid side chain, and a chemical bond between an amino acid side chain of a first amino acid of the peptide and an amino acid side chain of a second amino acid of the peptide, optionally between a carboxyl group of the amino acid side chain of the first amino acid and an amino group of the amino acid side chain of the second amino acid, wherein the peptide comprises at least one D-amino acid.

In an even more preferred embodiment, the compound of the invention comprises a cyclic peptide, wherein the peptide has the amino acid sequence K-R-W-H-E (SEQ ID No.: 34) and comprises a chemical bond between an N-terminal amino group of a first amino acid and an amino acid side chain, preferably between an N-terminal amino group of a first amino acid, preferably of the amino acid K, and a carboxyl group of an amino acid side chain of a second amino acid, optionally of E. Preferably, the amino acid side chain is the amino acid side chain of an amino acid selected from the group consisting of the amino acids E, D, K, R, N and Q.

In an even more preferred embodiment, the compound comprises a peptide which comprises the amino acid sequence as depicted in SEQ ID No.: 35 and comprises a chemical bond between an N-terminal amino group of a first amino acid, preferably of the amino acid K, and an amino acid side chain, preferably a carboxyl group of an amino acid side chain, of a second amino acid, preferably of the amino acid E, such as alga-2 (FIG. 12).

In an even more preferred embodiment, the compound comprises a peptide which comprises the amino acid sequence as depicted in SEQ ID No.: 36 and comprises a chemical bond between an N-terminal amino group of a first amino acid, preferably of the amino acid K, and an amino acid side chain, preferably a carboxyl group of an amino acid side chain, of a second amino acid, preferably of the amino acid E.

In an even more preferred embodiment, the compound comprises a peptide which comprises the amino acid sequence K-R-W-H-E (SEQ ID No.: 34) and comprises a chemical bond between an amino acid side chain, preferably the amino group of an amino acid side chain, of a first amino acid, preferably of the amino acid K, and the C-terminal carboxyl group of a second amino acid, preferably of E.

In another preferred embodiment, the chemical bond comprises the carboxyl group of an amino acid side chain of an amino acid E or D and/or the chemical bond comprises the amino group of an amino acid side chain of any one of the amino acids K, R, N or Q. Optionally, the amino acid side chain is modified or truncated.

In particular preferred are also compounds, wherein the cyclic peptide in the circle comprises at least one $CH_2$ group, preferably two $CH_2$ groups or more.

In a particularly very preferred embodiment, the compound comprises at least one D-amino acid, alternatively at least one amino acid of the cyclic peptide is a D-amino acid, optionally, 2, 3, 4, 5, 6, 7, 8, 9, 10, 11, 12, 13 or 14 amino acids of the cyclic peptide are D-amino acids. In one preferred embodiment, in the compound at least one amino acid of the amino acid sequence K-R-W-H (SEQ ID NO: 43), K-R-W-H-E (SEQ ID NO: 34) or R-W-H is a D-amino acid, preferably H, R and/or W is a D-amino acid, most preferably W or R or H.

In a more preferred embodiment of the invention, the peptide has the amino acid sequence K-R-W-H-E (SEQ ID No.: 34), K-N-R-W-H-E (SEQ ID No.: 35) or K-G-N-R-W-H-E (SEQ ID NO.: 36), comprising a chemical bond selected from the group consisting of a chemical bond between an N-terminal amino group of a first amino acid and an amino acid side chain, optionally a carboxyl group of an amino acid side chain, of a second amino acid, a chemical bond between a C-terminal carboxyl group of a first amino acid and an amino acid side chain, optionally an amino group of an amino acid side chain, of a second amino acid, and a chemical bond between an amino acid side chain of a first amino acid of the peptide and an amino acid side chain of a second amino acid of the peptide, optionally between a carboxyl group of the amino acid side chain of the first amino acid and an amino group of the amino acid side chain of the second amino acid, wherein at least one amino acid is a D-amino acid, preferably at least one amino acid of the amino acid sequence R-W-H is a D-amino acid.

Currently even more preferred is a compound of the invention, wherein the peptide has the amino acid sequence K-R-W-H-E (SEQ ID No.: 34) comprising a chemical bond between an N-terminal amino group of a first amino acid and an amino acid side chain, preferably a carboxyl group of an amino acid side chain, of a second amino acid, more preferably between the N-terminal amino group of K and the carboxyl group of the amino acid side chain of E, wherein at least one amino acid is a D-amino acid, preferably at least one amino acid of the amino acid sequence R-W-H is a D-amino acid, more preferably W is a D-amino acid.

Currently most preferred is a compound of the invention, wherein the peptide has the amino acid sequence K-R-W-H-E (SEQ ID No.: 41) comprising a chemical bond between the N-terminal amino group of K and the carboxyl group of the amino acid side chain of E, and wherein W is a D-amino acid, such as D3alga1 (cf. FIG. 9).

Currently most preferred is a compound of the invention, wherein the peptide comprises the amino acid sequence as depicted in SEQ ID No.: 35 and comprises a chemical bond between an N-terminal amino group of a first amino acid, preferably of the amino acid K, and an amino acid side chain, preferably a carboxyl group of an amino acid side chain of a second amino acid, preferably of the amino acid E, wherein at least one amino acid is a D-amino acid.

Currently most preferred is a compound of the invention, wherein the peptide comprises the amino acid sequence as depicted in SEQ ID No.: 36 and comprises a chemical bond between an N-terminal amino group of a first amino acid, preferably of the amino acid K, and an amino acid side chain, preferably a carboxyl group of an amino acid side chain of a second amino acid, preferably of the amino acid E, wherein the amino acid H is a D-amino acid, such as D6-alga-3 (cf. FIG. 10).

Currently most preferred is a compound of the invention, wherein the peptide comprises the amino acid sequence K-R-W-H-E (SEQ ID No.: 42) and comprises a chemical bond between an amino acid side chain, preferably the amino group of an amino acid side chain of a first amino acid, preferably of the amino acid K, and the C-terminal carboxyl group of a second amino acid, preferably of the amino acid E, wherein the amino acid R is a D-amino acid, such as D2-epal-1 (cf. FIG. 11).

The compound of any one of the preceding claims, wherein the peptide is selected from the group consisting of a peptide having the amino acid sequence K-R-W-H-E (SEQ ID No.: 41), comprising a chemical bond between the N-terminal amino group of the amino acid K and the carboxyl group of the amino acid side chain of the amino acid E, and wherein the amino acid W is a D-amino acid, such as D3-alga-1, a peptide having the amino acid sequence as depicted in SEQ ID No.: 35, comprising a chemical bond between the N-terminal amino group of the amino acid K and the carboxyl group of the amino acid side chain of the amino acid E, such as alga-2, a peptide comprising the amino acid sequence SEQ ID No.: 36, comprising a chemical bond between the N-terminal amino group of the amino acid K and the carboxyl group of the amino acid side chain of the amino acid E, wherein the amino acid H is a D-amino acid, such as D6-alga-3, and a peptide comprising the amino acid sequence K-R-W-H-E (SEQ ID No.: 42), comprising a chemical bond between the amino group of the amino acid side chain of the amino acid K and the C-terminal carboxyl group of the amino acid E, wherein the amino acid R is a D-amino acid, such as D2-epal-1.

Also provided is a pharmaceutical composition comprising a compound of the invention and a pharmaceutically acceptable carrier. Optionally, the compound or the pharmaceutical composition is formulated for intravenous, oral, nasal, or subcutaneous administration.

Also provided is the compound of the invention or the pharmaceutical composition of the invention for use as a medicament. Also provided is the use of a compound of the invention or a pharmaceutical composition of the invention in the manufacturing of a medicament for treating any of the diseases herein listed below.

In a preferred embodiment, the compound or the pharmaceutical composition of the invention is for use in treating a disease selected from the group consisting of cancer, an angiogenesis related disease, a disease from the field of ophthalmology, diseases associated with an increased invasive potential of cells, and inflammatory disorders in a human being. Preferably, the cancer is a metastasizing cancer. A "metastasizing cancer" is a cancer which may form or often forms metastases. A metastasizing cancer which has already spread from the part of the body where it started, i.e. the primary site, to other parts of the body, is also denoted metastatic cancer. When cancer cells break away from a tumor, they can travel to other areas of the body through the bloodstream or the lymph system. Such cancer cells may then form new tumors in other areas of the body.

In another preferred embodiment, the disease is selected from the group consisting of estrogen receptor-dependent breast cancer, estrogen receptor-independent breast cancer, hormone receptor-dependent prostate cancer, hormone receptor-independent prostate cancer, brain cancer, renal cancer, colon cancer, familial adenomatous polyposis (FAP), colorectal cancer, pancreatic cancer, bladder cancer, esophageal cancer, stomach cancer, genitourinary cancer, gastrointestinal cancer, uterine cancer, ovarian cancer, astrocytomas, gliomas, skin cancer, squamous cell carcinoma, Keratoakantoma, Bowen disease, cutaneous T-Cell Lymphoma, melanoma, basal cell carcinoma, actinic keratosis; ichtiosis; acne, acne vulgaris, sarcomas, Kaposi's sarcoma, osteosarcoma, head and neck cancer, small cell lung carcinoma, non-small cell lung carcinoma, leukemia, lymphomas and/or other blood cell cancers, thyroid resistance syndrome, diabetes, thalassemia, cirrhosis, protozoal infection, rheumatoid arthritis, rheumatoid spondylitis, all forms of rheumatism, osteoarthritis, gouty arthritis, multiple sclerosis, insulin dependent diabetes mellitus, non-insulin dependent diabetes, asthma, rhinitis, uveithis, lupus erythematoidis, ulcerative colitis, Morbus Crohn, inflammatory bowel disease, chronic diarrhea, psoriasis, atopic dermatitis, bone disease, fibroproliferative disorders, atherosclerosis, aplastic anemia, DiGeorge syndrome, Graves' disease, epilepsia, status epilepticus, alzheimer's disease, depression, schizophrenia, schizoaffective disorder, mania, stroke, mood-incongruent psychotic symptoms, bipolar disorder, affective disorders, meningitis, muscular dystrophy, multiple sclerosis, agitation, cardiac hypertrophy, heart failure, reperfusion injury, diabetic retinopathy, age-related macular degeneration, allergic diseases, e.g. asthma, due to an increase in eosinophil granulocytes, rejection of heart transplantation, and obesity in a human being.

Preferably, the said cancer shows expression of CD44v6.

In another preferred embodiment, said cancer is classifiable as Stage III or Stage IV according to the TNM anatomic/prognostic group system of the cancer staging system of the American Joint Committee on Cancer. More preferably, said cancer is classifiable as Stage IV according to the TNM anatomic/prognostic group system of the cancer staging system of the American Joint Committee on Cancer.

In another preferred embodiment, said cancer is a metastasizing cancer selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, pancreatic cancer, head and neck squamous cell cancer, and breast cancer. In another more preferred embodiment of the invention, said cancer is a metastasizing cancer selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, pancreatic cancer, and breast cancer, wherein said metastasizing cancer is classifiable as Stage IV according to the TNM anatomic/prognostic group system of the cancer staging system of the American Joint Committee on Cancer, and wherein said metastasizing cancer shows expression of CD44v6.

Preferred cancers may be metastasizing forms of Hodgkin lymphoma, colorectal cancer, cervical cancer, head and neck cancer, gastric cancer, pancreatic cancer and breast cancer, as for these cancers an expression of CD44v6 has been shown. In a preferred embodiment, the compound and pharmaceutical composition of the invention are for use in treating cancers when metastases have already formed, such as metastasizing forms of Hodgkin lymphoma, colorectal cancer, cervical cancer, head and neck cancer, gastric cancer, pancreatic cancer and breast cancer in a human being A person skilled in the art will understand that any compound that provides for the same amino acids or at least the same overall configuration of the cyclic peptide as cyclic peptides described herein will also be efficient in not only preventing formation of metastasis, but also removing already formed metastases in cancers such as Hodgkin lymphoma, colorectal cancer, cervical cancer, head and neck cancer, gastric cancer, pancreatic cancer and breast cancer, as well as angiogenesis related diseases, a disease from the field of ophthalmology, diseases associated with an increased invasive potential of cells, and inflammatory disorders.

The invention therefore in some embodiments contemplates the use of peptidomimetics of any of the cyclic peptides described herein. These peptidomimetics will preferably have the same amino acids but an altered backbone which provides for the same overall configuration of the peptidomimetic as does the cyclic peptide itself, but which is e.g. more resistant to protease cleavage. Preferred peptidomimetics are e.g. isosteric peptoids, which comprise poly-N-substituted glycines in the peptide bonds of the backbone.

The present invention also considers further modified forms of the cyclic peptides and peptidomimetics described herein. Such modified cyclic peptides or peptidomimetics may comprise e.g. chemically or enzymatically attached modifications that render the peptides more stable, e.g. against protease degradation, that allow to provide the peptides or peptidomimetics as pharmaceutically acceptable salts, or which e.g. improve the biological properties of the cyclic peptides or peptidomimetics such as half-life. Exemplary modifications comprise amino acids, amino acid derivatives, and aromatic-hydrophobic modifications, optionally phenyl acetic acid or 3-indole acetic acid. In a preferred embodiment, the modification is not DOTA or a myristoyl group. Further modifications of peptides are known to the skilled person. Such modified cyclic peptides or peptidomimetics are generally referred to, in the context of the present invention, as compounds or peptide compounds. These compounds or cyclic peptide compounds may be formulated for oral administration, e.g. by inhalation, for nasal administration, or administration by injection such as intravenous or subcutaneous administration.

In one embodiment the present invention also relates to compounds and pharmaceutical compositions for use in treating cancers when metastases have already formed such as metastasizing forms of Hodgkin lymphoma, colorectal cancer, cervical cancer, head and neck cancer, gastric cancer, pancreatic cancer and breast cancer in a human being wherein these pharmaceutical compositions comprise the compounds/peptide compounds as described above. These pharmaceutical compositions may comprise pharmaceutically acceptable excipients and the compounds and pharmaceutical compositions may be formulated for oral administration such as by inhalation, nasal administration or administration by injection.

The invention also relates to methods of treating cancer, an angiogenesis related disease, a disease from the field of ophthalmology, diseases associated with an increased invasive potential of cells, and inflammatory disorders in a human being. Further, the invention relates to methods of treating cancers when metastases have already formed such as metastasizing forms of Hodgkin lymphoma, colorectal cancer, cervical cancer, head and neck cancer, gastric cancer, pancreatic cancer and breast cancer in a human being in need thereof by administering the cyclic peptides, peptidomimetics thereof or modified forms thereof, i.e. the compounds in accordance with the present invention, or pharmaceutical compositions comprising compounds in accordance with the present invention to a human being in need thereof.

The compounds in accordance with the present invention, i.e. the cyclic peptides, peptidomimetics thereof or modified forms thereof, the pharmaceutical compositions of the present invention, and the methods in accordance with the present invention are considered for treating cancers where metastases have already formed and may have even spread across the body. These cancers are also designated as metastasizing cancers.

Metastasizing cancers in accordance with the invention include metastasizing forms of cancers for which expression of CD44v6 has been observed on cancer tissues or can be observed upon corresponding testing e.g. with CD44v6 antibodies. Metastasizing cancers in accordance with the invention include metastasizing forms of Hodgkin lymphoma, colorectal cancer, cervical cancer, head and neck cancer, gastric cancer, pancreatic cancer, head and neck squamous cell cancer and breast cancer and other forms of cancer mentioned above and in the claims.

Such metastasizing cancer forms of the various cancers such as Hodgkin lymphoma, colorectal cancer, cervical cancer, head and neck cancer, gastric cancer, pancreatic cancer and breast cancer can be identified according to the TNM Anatomic Stage/Prognostic Group System of the Cancer Staging Manual of the American Joint Committee on Cancer ($7^{th}$ edition, 2010, Springer). Metastasizing cancers in accordance with the invention will typically be classified as a Stage IV cancer according to the TNM Anatomic Stage/Prognostic Group System, particularly if M is set as 1. The Cancer Staging Manual of the American Joint Committee on Cancer ($7^{th}$ edition, 2010, Springer) describes the TNM Anatomic Stage/Prognostic Group System and under which conditions a cancer is considered to be of e.g. Stage I, II, III and IV for the various cancers mentioned herein and is thus included by reference as far.

For example, in a particularly preferred embodiment the present invention considers the compounds of the present invention, i.e. the cyclic peptides, preferably comprising D2-epal1, D6-alga3, Alga-2, Alga1 and D3-alga1, peptidomimetics thereof or modified forms thereof, the pharmaceutical compositions described hereinafter and methods described hereinafter for treating breast cancer or colorectal cancer in a human subject, for which the breast or colorectal cancer is classifiable as Stage IV according to the TNM Anatomic Stage/Prognostic Group System of the Cancer Staging Manual of the American Joint Committee on Cancer ($7^{th}$ edition, 2010, Springer, see pages 145 to 166 for colorectal cancer and pages 347 to 378 for breast cancer).

It is to be understood that for all aspects and embodiments of the present invention, i.e. the compounds, cyclic peptides, pharmaceutical compositions and methods as described hereinafter, it is always preferred to use the cyclic peptides as described herein for treating metastasizing cancers in a human being, and in particular for treating metastasizing cancers which are classifiable as Stage IV according to the TNM Anatomic Stage/Prognostic Group System of the Cancer Staging Manual of the American Joint Committee on Cancer ($7^{th}$ edition, 2010, Springer).

In a particularly preferred embodiment, the pharmaceutical composition of the invention comprises a cyclic peptide comprising the amino acid sequence K-R-W-H-E (SEQ ID No.: 41) and comprising a chemical bond between the N-terminal amino group of the amino acid K and the carboxyl group of the amino acid side chain of the amino acid E, wherein the amino acid W is a D-amino acid, such as D3alga1 (cf. FIG. 9), and a pharmaceutically acceptable carrier, optionally, formulated for intravenous, oral, nasal, or subcutaneous administration, preferably for formulated for intravenous administration. The invention also provides in a particularly preferred embodiment, a cyclic peptide comprising the amino acid sequence K-R-W-H-E (SEQ ID No.: 41) comprising a chemical bond between the N-terminal amino group of K and the carboxyl group of the amino acid side chain of E, wherein W is a D-amino acid, such as D3alga1 (cf. FIG. 9) for use as a medicament. Preferably, this particular cyclic peptide is for use in treating a disease selected from the group consisting of cancer, an angiogenesis related disease, a disease from the field of ophthalmology, diseases associated with an increased invasive potential of cells, and inflammatory disorders in a human being, more preferably for use in the treatment of cancer, preferably metastasizing cancer and more preferably metastasizing cancer which has already formed metastases.

In a particularly preferred embodiment, the pharmaceutical composition of the invention comprises a cyclic peptide comprising the amino acid sequence as depicted in SEQ ID No.: 35 and a chemical bond between the N-terminal amino group of the amino acid K, and the carboxyl group of the amino acid side chain of the amino acid E, such as Alga-2 (cf. FIG. 12), and a pharmaceutically acceptable carrier, optionally, formulated for intravenous, oral, nasal, or subcutaneous administration, preferably for formulated for intravenous administration. The invention also provides in a particularly preferred embodiment, a cyclic peptide comprising the amino acid sequence as depicted in SEQ ID No.: 35 and a chemical bond between the N-terminal amino group of K and the carboxyl group of the amino acid side chain of E, such as Alga-2 (cf. FIG. 12) for use as a medicament. Preferably, this particular cyclic peptide is for use in treating a disease selected from the group consisting of cancer, an angiogenesis related disease, a disease from the field of ophthalmology, diseases associated with an increased invasive potential of cells, and inflammatory disorders in a human being, more preferably for use in the treatment of cancer, preferably metastasizing cancer and more preferably metastasizing cancer which has already formed metastases.

In a particularly preferred embodiment, the pharmaceutical composition of the invention comprises a cyclic peptide comprising the amino acid sequence as depicted in SEQ ID No.: 36 and a chemical bond between the N-terminal amino group of the amino acid K and the carboxyl group of an amino acid side chain of the amino acid E, wherein the amino acid H is a D-amino acid, such as D6-alga3 (cf. FIG. 10), and a pharmaceutically acceptable carrier, optionally, formulated for intravenous, oral, nasal, or subcutaneous administration, preferably for formulated for intravenous administration. The invention also provides in a particularly preferred embodiment, a cyclic peptide comprising an amino acid sequence as depicted in SEQ ID No.: 36 and a chemical bond between the N-terminal amino group of the amino acid K and the carboxyl group of the amino acid E, wherein the amino acid H is a D-amino acid, such as D6-alga3 (cf. FIG. 10) for use as a medicament. Preferably, this particular cyclic peptide is for use in treating a disease selected from the group consisting of cancer, an angiogenesis related disease, a disease from the field of ophthalmology, diseases associated with an increased invasive potential of cells, and inflammatory disorders in a human being, more preferably for use in the treatment of cancer, preferably metastasizing cancer and more preferably metastasizing cancer which has already formed metastases.

In a particularly preferred embodiment, the pharmaceutical composition of the invention comprises a cyclic peptide comprising the amino acid sequence K-R-W-H-E (SEQ ID No.: 42) and a chemical bond between the amino group of the amino acid side chain of the amino acid K, and the C-terminal carboxyl group of the amino acid E, wherein the amino acid R is a D-amino acid, such as D2-epal1 (cf. FIG. 11), and a pharmaceutically acceptable carrier, optionally, formulated for intravenous, oral, nasal, or subcutaneous administration, preferably for formulated for intravenous administration. The invention also provides in a particularly preferred embodiment, a cyclic peptide comprising the amino acid sequence K-R-W-H-E (SEQ ID No.: 42) and a chemical bond between the amino group of the amino acid side chain of the amino acid K and the C-terminal carboxyl group of the amino acid E, wherein the amino acid R is a D-amino acid, such as D2-epal1 (cf. FIG. 11) for use as a medicament. Preferably, this particular cyclic peptide is for use in treating a disease selected from the group consisting of cancer, an angiogenesis related disease, a disease from the field of ophthalmology, diseases associated with an increased invasive potential of cells, and inflammatory disorders in a human being, more preferably for use in the treatment of cancer, preferably metastasizing cancer and more preferably metastasizing cancer which has already formed metastases.

FIGURE LEGENDS

FIG. 1: FIG. 1 provides structural information on the cyclic peptides of the present invention. It further shows the structure of the pentapeptide K-R-W-H-E (SEQ ID NO: 34) and possible abbreviations depending on the kind of chemical bonds which have been used in the method of producing for the cyclization step. For example, the first syllable gives the chemical group on the N-terminal side of the tripeptide R-W-H which participates in cyclization: "al" (alpha) denotes the N-terminal amino group and "ep" (epsilon) the amino group of the amino acid side chain of the amino acid K. The Greek letter is thus the position in the amino acid side chain where the reaction occurs. Greek letters are commonly used to number the carbon atoms of an amino acid side chains starting from the alpha carbon atom being the carbon atom in the peptide backbone. The second syllable gives the chemical group which participates in cyclisation on the C-terminal site of the tripeptide R-W-H: "al" (alpha) denotes the C-terminal carboxyl group and "ga" (gamma) the carboxyl group of the amino acid side chain of the amino acid E. The number in the abbreviations indicates the length of the peptide according to the list given in FIG. 1. FIG. 1 discloses SEQ ID NOS 34, 34, 34, 34, 35, 35, 35, 35, 36, 36, 36, 36, 44 and 34, respectively, in order of appearance.

FIG. 2: Exemplary cyclic peptides according to the present invention and focuses in particular on modified peptides.

FIG. 3: A cyclic CD44v6 5mer (alga1, cf. FIG. 1) and a cyclic CD44v6 5mer containing a D-amino acid at position 3 (D3alga1, cf. FIGS. 1 and 9) block activation of c-Met and Erk. A: alga1; B: D3alga1. The first row shows the activation status of Met, below the loading control of total Met protein. The third row shows the activation status of the Erk, a downstream target of the Met pathway, below total Erk protein amount is presented. "ctrl peptide"=control peptide N-A-A-A-E (SEQ ID NO: 37)

Figure 4:
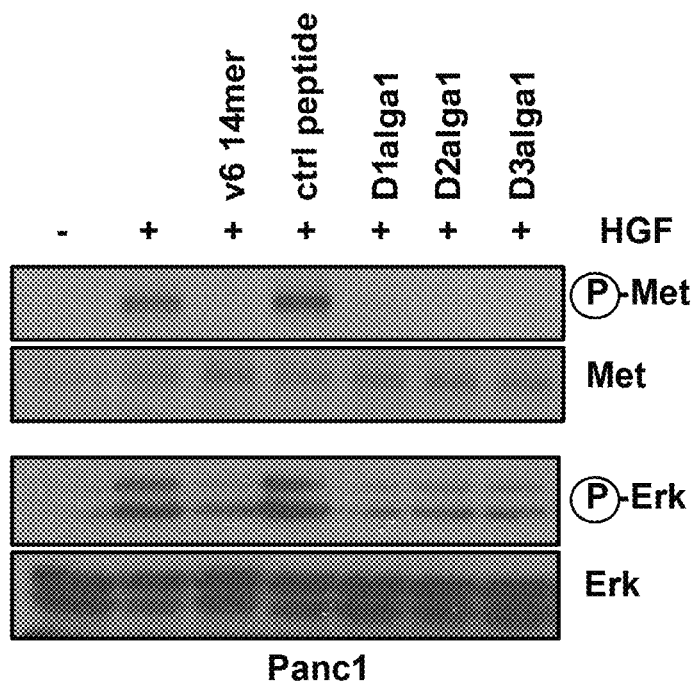

FIG. 4: Cyclic CD44v6 5mer containing a D-amino acid at positions 1, 2 and 3, respectively (D1alga1, D2alga1, D3alga1), blocks activation of c-Met and Erk. The first row shows the activation status of Met, below the loading control of total Met protein. The third row shows the activation status of the Erk, a downstream target of the Met pathway, below total Erk protein amount is presented. "ctrl peptide"=control peptide N-A-A-A-E (SEQ ID NO: 37)

Figure 5:
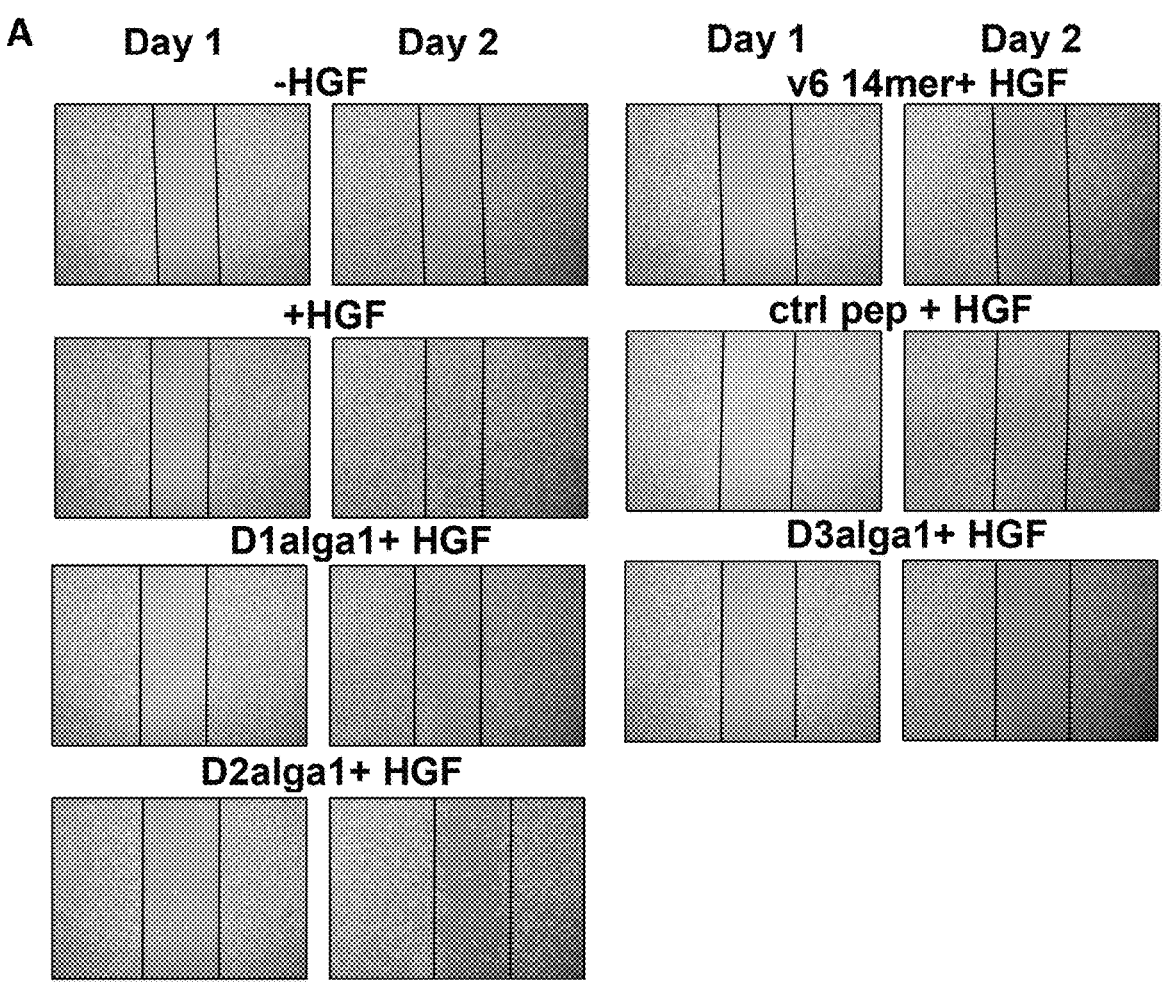
Figure 5:
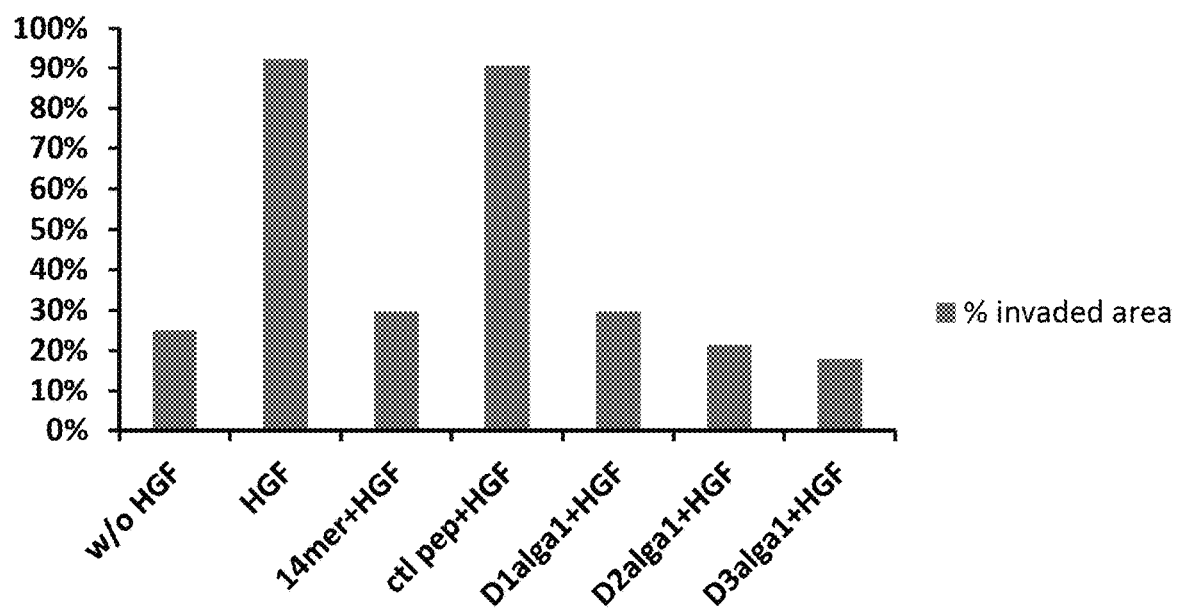

FIG. 5: A: Wound healing assay. B: Quantitative evaluation of the wound healing assay with the computer program ImageJ. "ctrl pep"=control peptide N-A-A-A-E (SEQ ID NO: 37)

Figure 6:
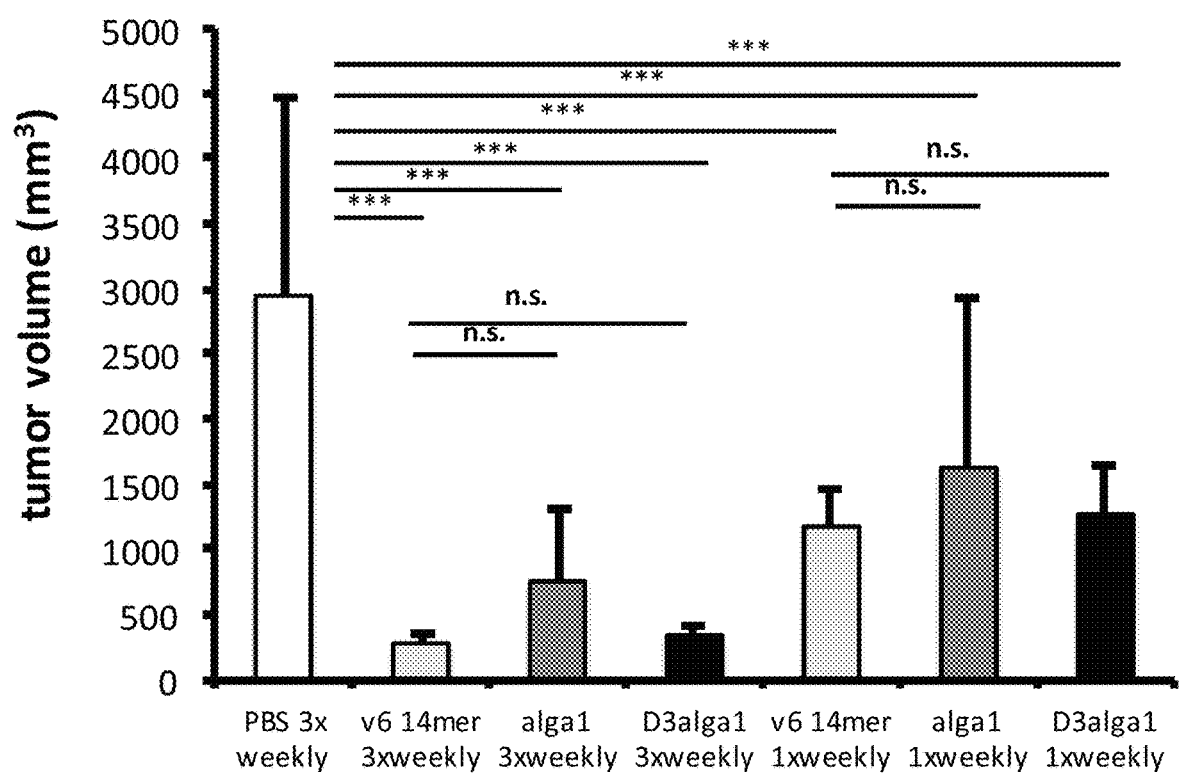
Figure 6:
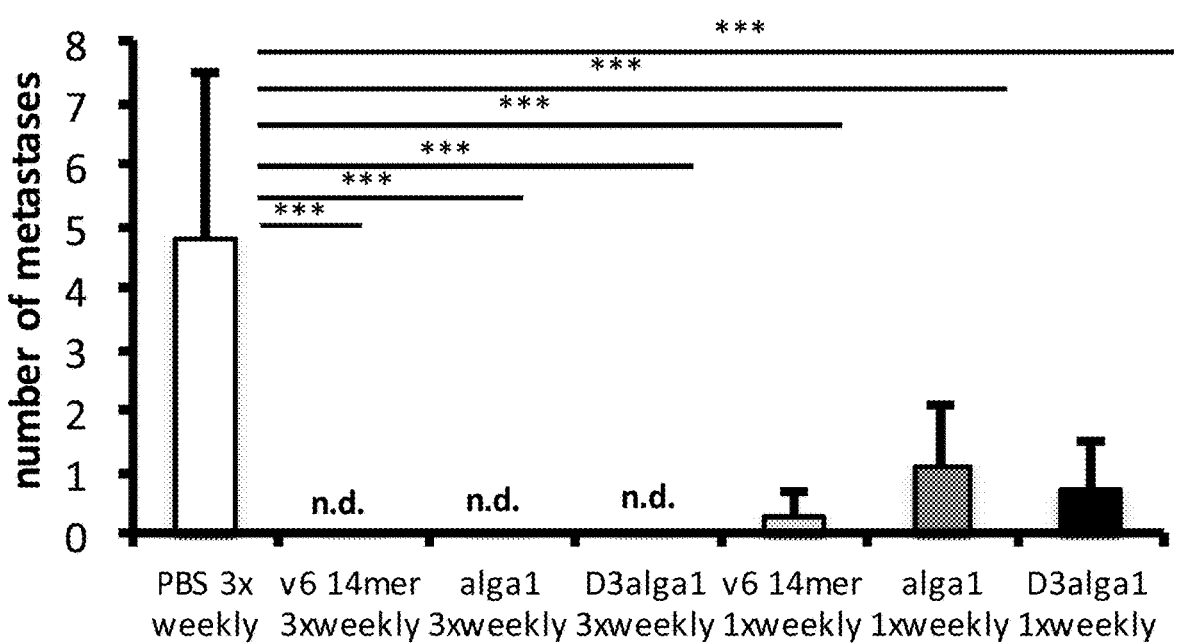

FIG. 6: Side by side comparison of the human CD44v6 14mer (V6 14MER), alga1 and D3alga1 for their effect on tumor growth inhibition and inhibition on tumor metastasis. A: Inhibition of tumor growth. Bar chart representing the average tumor volume of each treatment group. Significance was calculated using Student's t test: *p<0.001. B: Inhibition of metastatic spreading to the liver. Bar chart representing the average tumor number of metastases of each treatment group. Significance was calculated using Student's t test: *p<0.001. "ctrl pep"=control peptide N-A-A-A-E (SEQ ID NO: 37)

Figure 7:
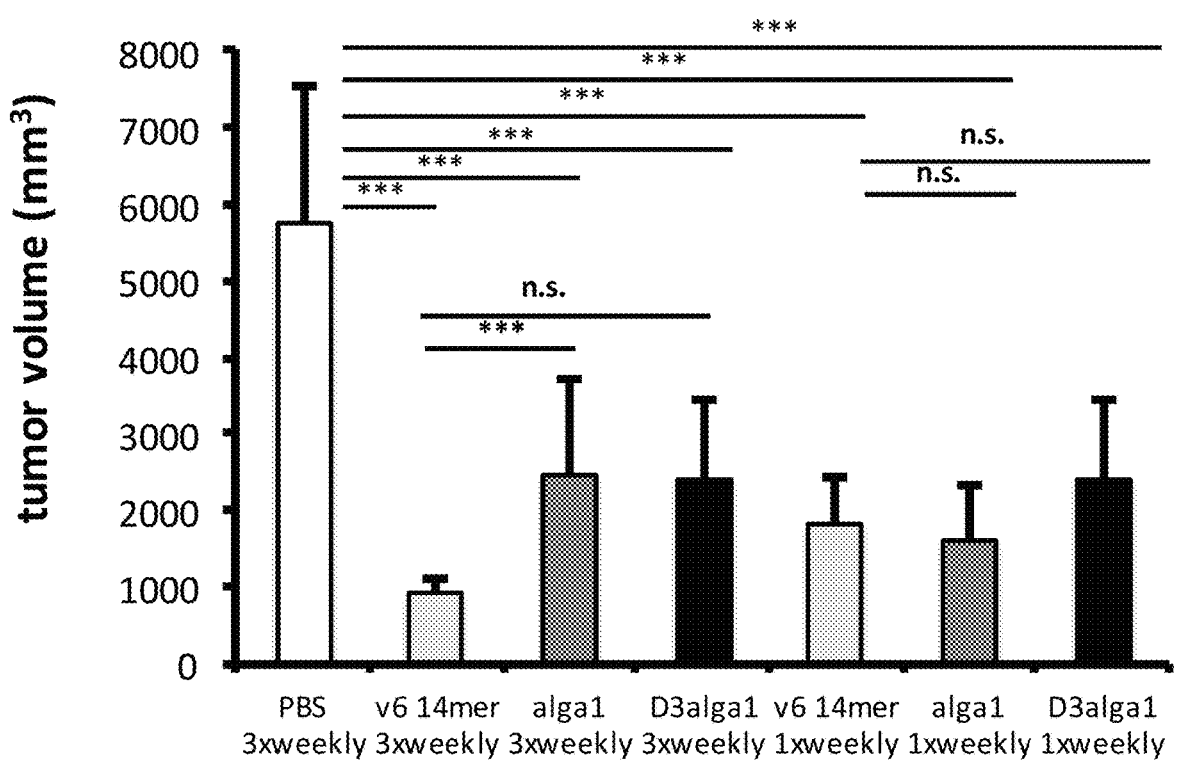
Figure 7:
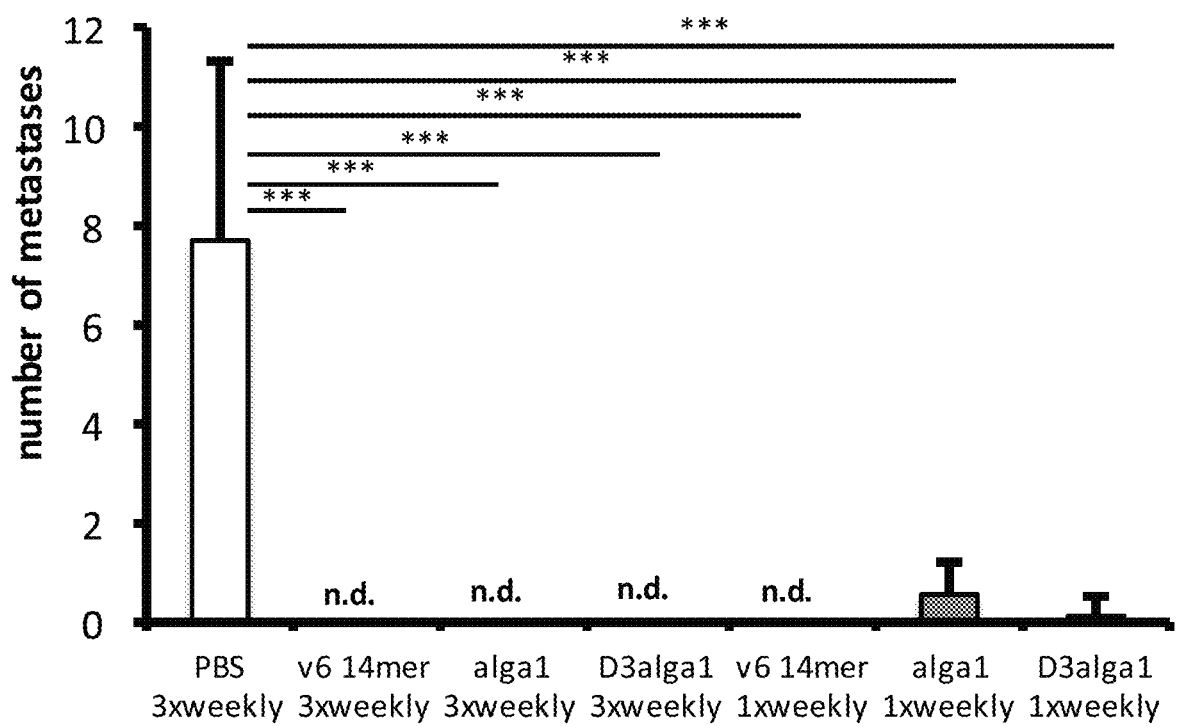

FIG. 7: Side by side comparison of the human CD44v6 14mer (V614MER), alga1 and D3alga 1 for their effect on regression of already established metastases. A: Inhibition of tumor growth. Bar chart representing the average tumor volume of each treatment group. Significance was calculated using Student's t test: *p<0.001. B: Regression of established liver metastases. Bar chart representing the average tumor number of metastases of each treatment group. Significance was calculated using Student's t test: *p<0.001. "ctrl pep"=control peptide N-A-A-A-E (SEQ ID NO: 37).

Figure 8:
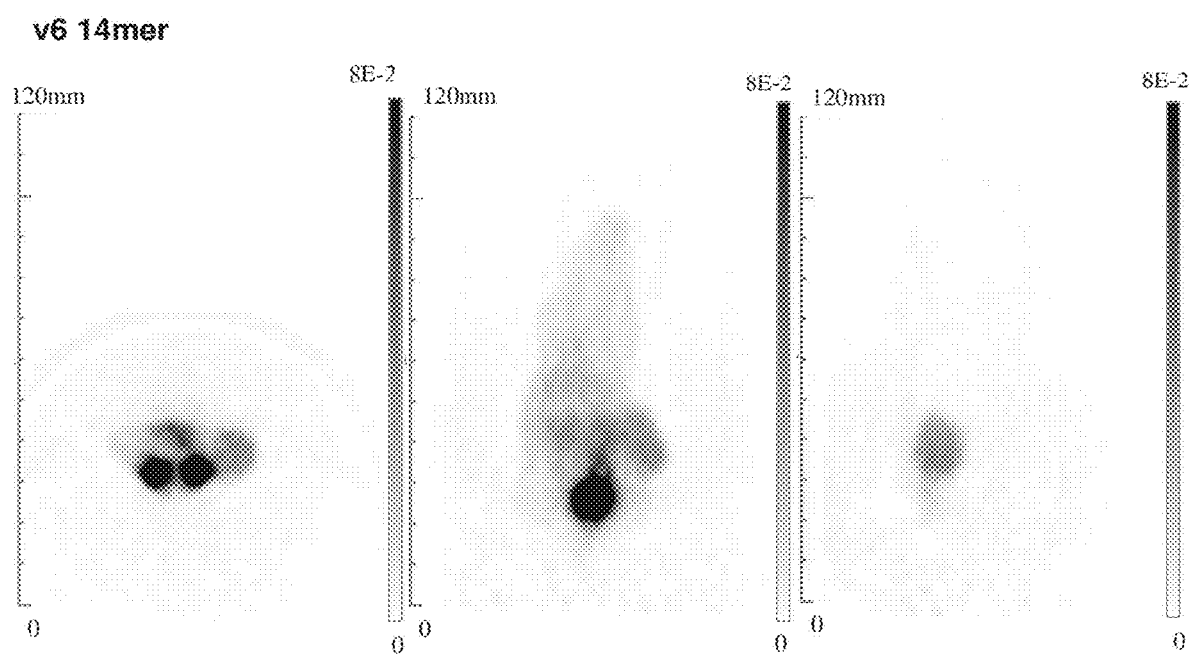
Figure 8:
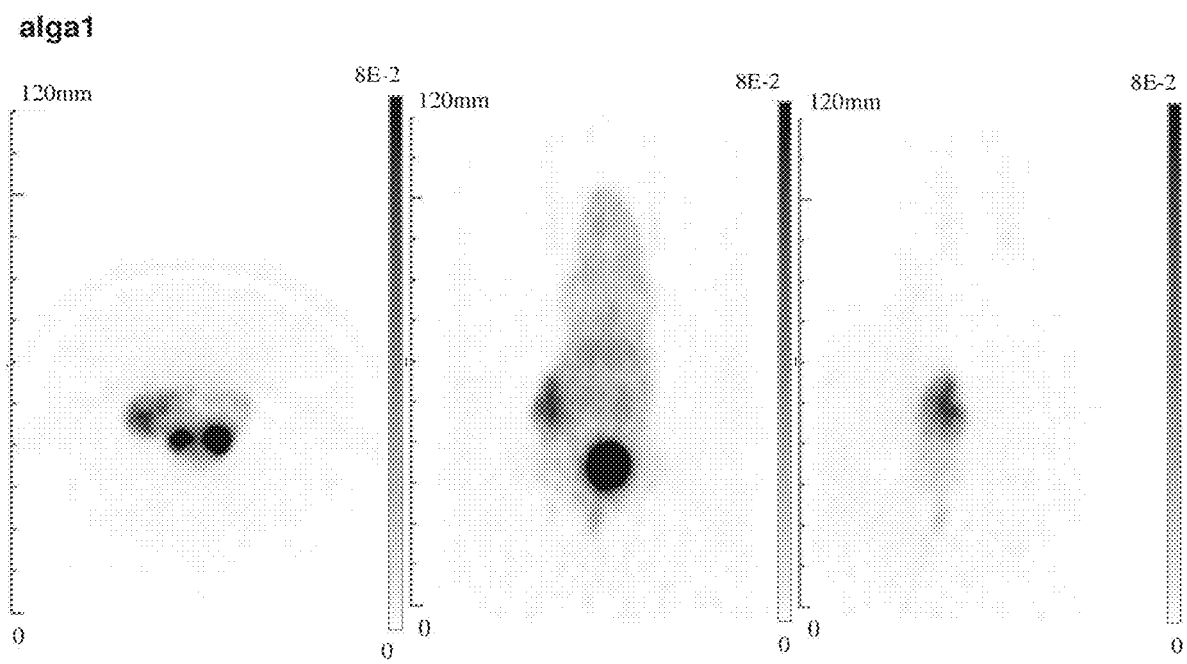
Figure 8:
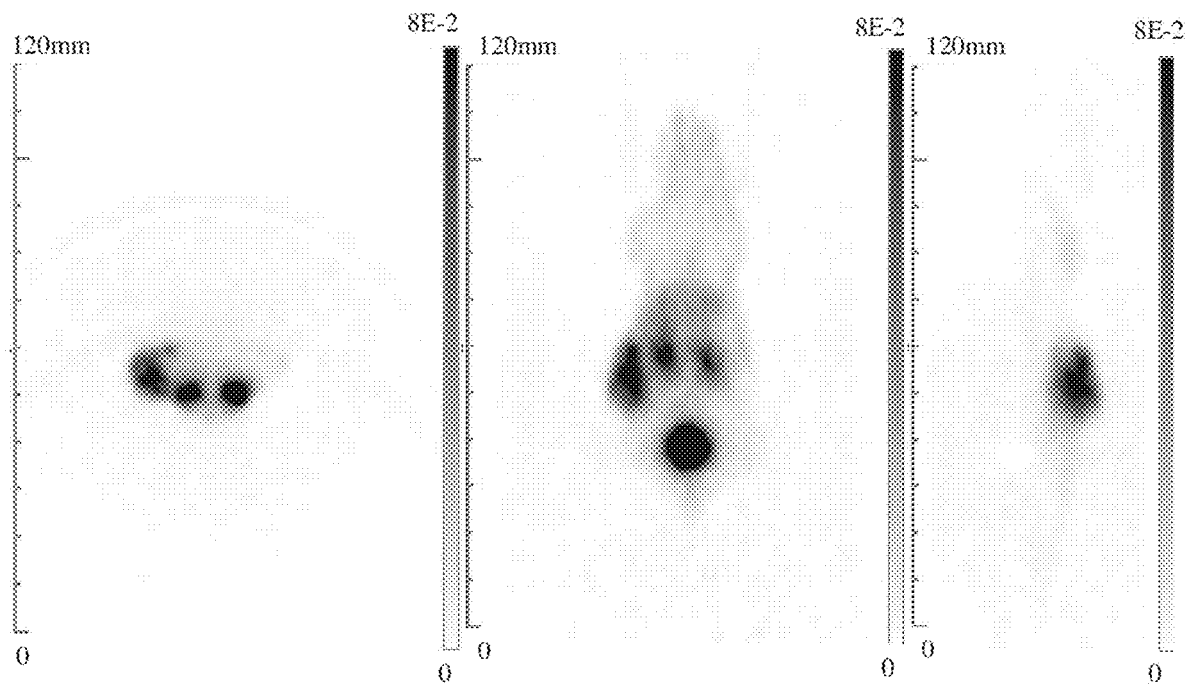

FIG. 8: Comparison of the tumor accumulation of the v6 14-mer linear peptide and alga1 and D3alga1 after labelling with $^{68}$Ga using PET imaging. Each image shows a coronar view of the tumor xenograft of L3.6pl cells in comparison to the kidneys (left, kidneys appear as two black blots, xenograft on the right for v6 14mer, on the left for alga1 and D3alga1), in comparison to the bladder (middle, bladder appears as one black blot, xenograft on the right of the bladder for v6 14mer, on the left of the bladder for alga1 and D3alga1), and in an isolated view of the xenograft (right).

FIG. 9: Structure of D3 alga1 (cf. FIG. 1, cyclic K-R-W-H-E (SEQ ID NO: 41), wherein cyclisation is via the N-terminal amino group and the carboxyl group in the amino acid side chain of E, and wherein W is a D-amino acid).

FIG. 10: Structure of D6-alga3 (cy[αKGNRWHEγ], wherein cyclisation is via the N-terminal amino group of K and the carboxyl group in the amino acid side chain of E, and wherein H is a D-amino acid).

FIG. 11: Structure of D2-epal1 (cy[εKRWHEα]γ] (SEQ ID NO: 42), wherein cyclisation is via the amino group in the amino acid side chain of K and the C-terminal carboxyl group of E, and wherein R is a D-amino acid).

FIG. 12: Structure of alga2 (cy[αKNRWHEγ] (SEQ ID NO: 35), wherein cyclisation is via the N-terminal amino group of K and the carboxyl group in the amino acid side chain of E).

FIG. 13: List of preferred D-amino acid containing cyclic peptides of the invention which comprise at least one non-peptide bond between two adjacent amino acids in the circle. The sequence information is to be read as follows: the part in square brackets indicates the two adjacent amino acids which are connected via a chemical bond which is not a peptide bond. The Greek letters give further information on the chemical bond between the two adjacent amino acids. For example, [εKγE] in the sequence of D2-apga-1 denotes that the cyclic peptides comprises a bond between the amino group at ε-position in the amino acid side chain of lysine (K) and the carboxyl group in the γ-position in the amino acid side chain of glutamic acid (E) (cf. FIG. 1). "cy" denotes that the peptide is a cyclic peptide. In round brackets, the amino acid sequence of the cyclic peptide is given. Here, a lowercase letter indicates that the amino acid is a D-amino acid, while capital letters indicate a L-amino acid. Hence, D2-apga-1 contains the D-amino acid arginine (R). Regarding the indicated name of the peptides, D denotes that at least one D-amino acid is present. The Figure after the letter "D" indicates the position of the D-amino acid in the sequence starting with the first K on the N-terminal side of the motif R-W-H as the amino acid at position 1. The first syllable of the second part of the name indicates the chemical group on the N-terminal side of the central motif sequence R-W-H which participates in the chemical bond which is not a peptide bond: "al" (alpha) denotes the N-terminal amino group and "ep" (epsilon) the amino group of the amino acid side chain of K. The Greek letter is thus the position in the amino acid side chain where the cyclisation reaction occurs and which participates in the chemical bond which is not a peptide bond. The second syllable gives the chemical group which participates in cyclisation on the C-terminal site of the tripeptide R-W-H: "al" (alpha) as second syllable is the C-terminal carboxyl group and "ga" (gamma) the carboxyl group of the amino acid side chain of the amino acid E. The number in the abbreviations indicates the length of the peptide according to the list as also given in FIG. 1. Hence, "1" indicates a "5" mer as the minimal peptide length, "2" indicates a 6 mer, "3" indicates a 7 mer and so forth. FIG. 13 the sequence "D3-epga-1" as SEQ ID NO: 41 and the sequence "D2-epal-1" as SEQ ID NO: 42.

FIG. 14: List of cyclic peptides not comprising a D-amino acid. The names and sequences are indicated as in the Figure legend of FIG. 13. FIG. 14 discloses SEQ ID NOS 34, 34, 35 and 36, respectively, in order of appearance.

Figure 15:
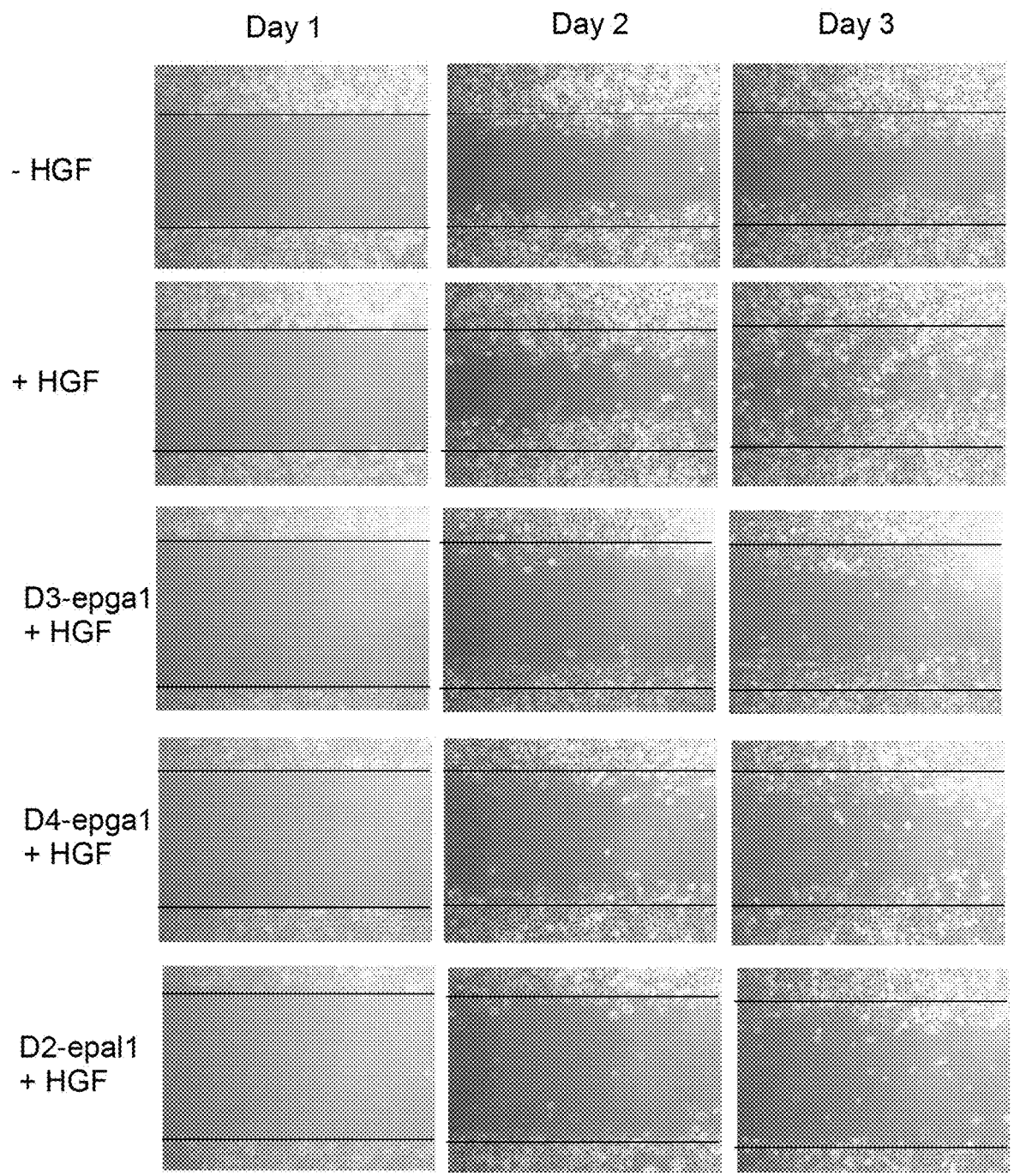
Figure 15:
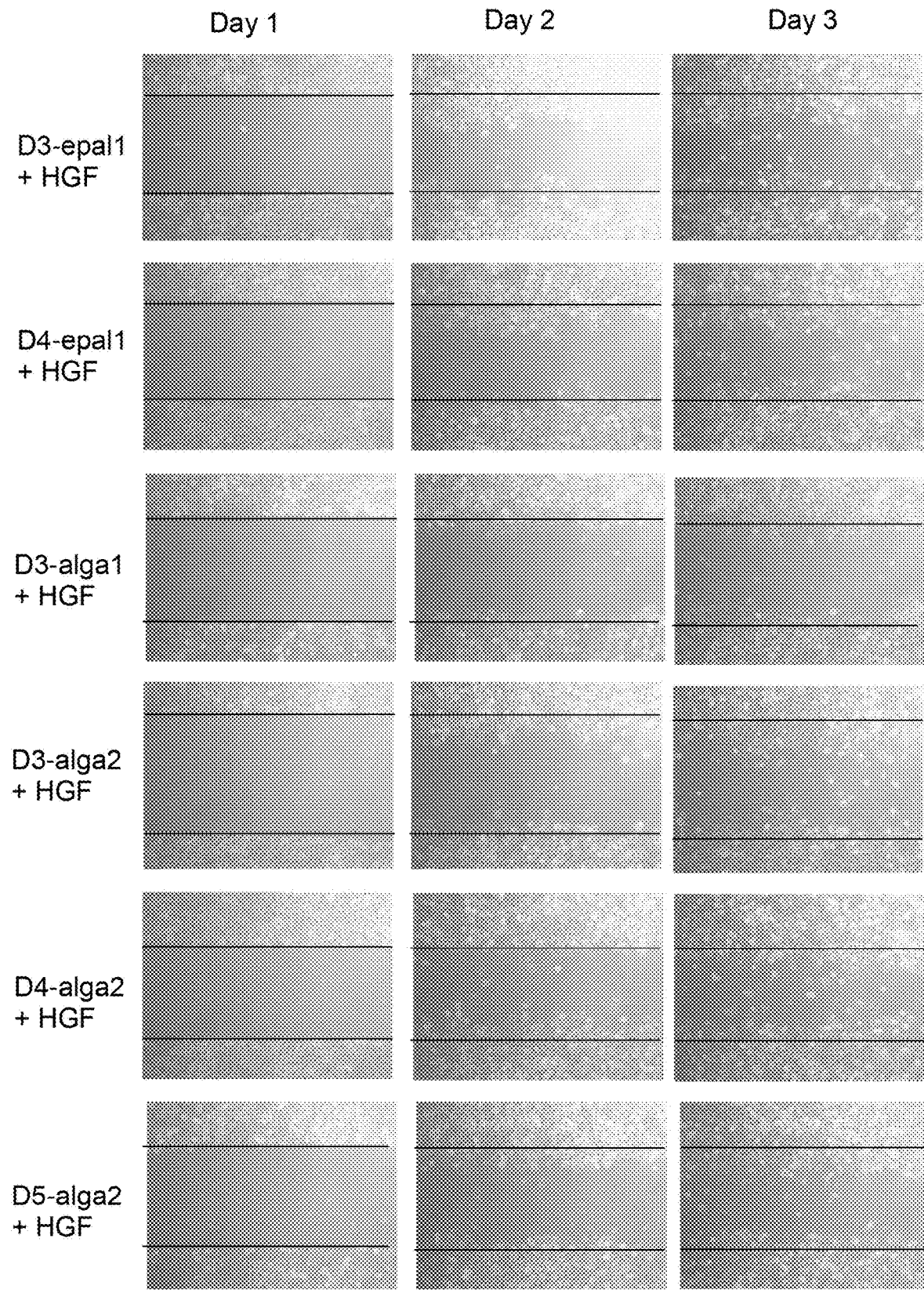
Figure 15:
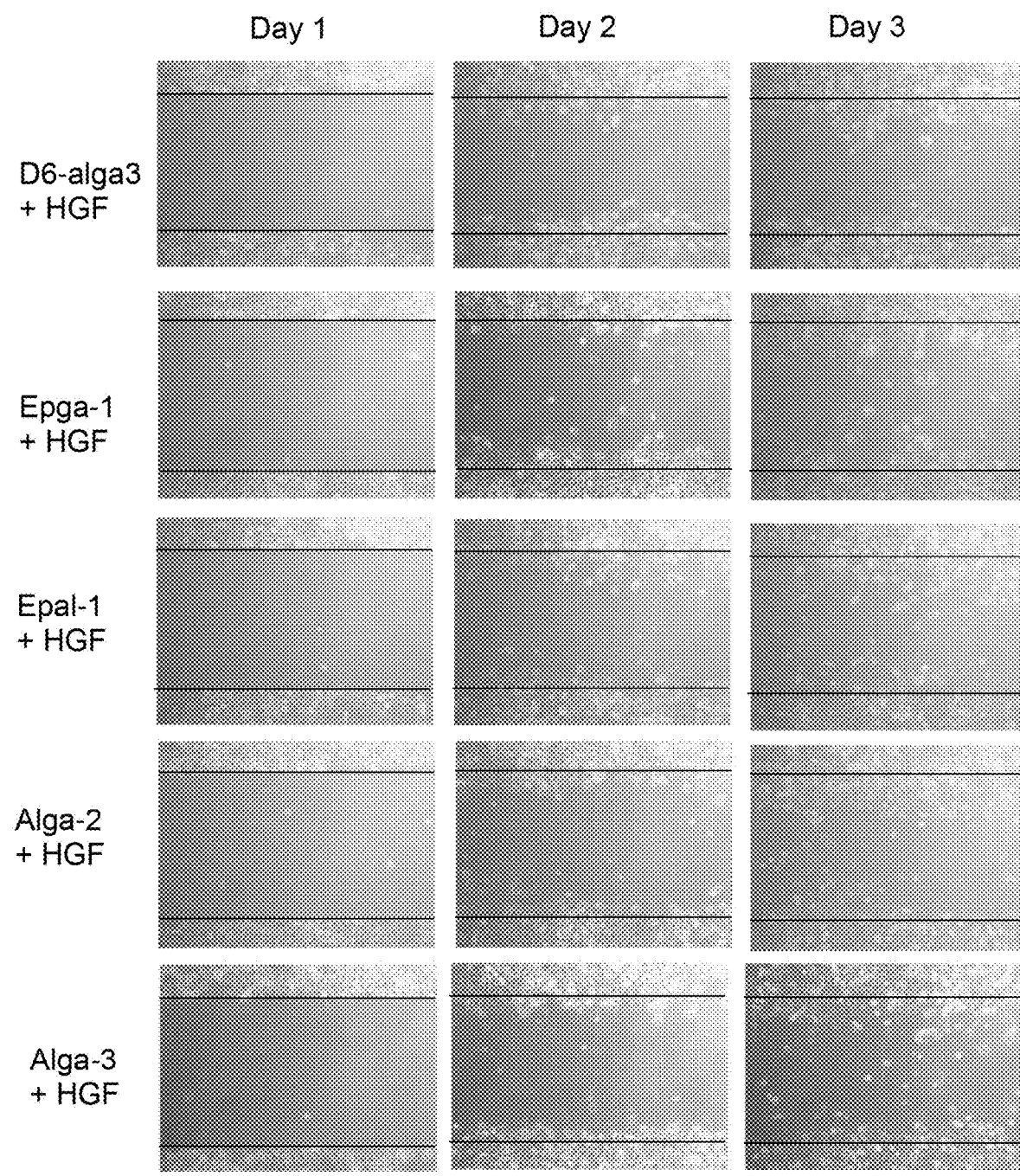

FIG. 15: Results of the wound healing assay according to Example 9, wherein the blocking efficiency of the indicated peptides is tested.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody, which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±20%, preferably ±15%, more preferably ±10%, and even more preferably ±5%.

Furthermore, the terms "first", "second", "third" or "(a)", "(b)", "(c)", "(d)" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps unless indicated otherwise, i.e. the steps may be carried out simultaneously or there may be time intervals of seconds, minutes, hours, days, weeks, months or even years between such steps, unless otherwise indicated in the application as set forth herein above or below.

Technical terms are used by their common sense. If a specific meaning is conveyed to certain terms, definitions of terms will be given in the following in the context of which the terms are used.

As mentioned above, the present invention is concerned with cyclic peptides or peptide compounds useful in treating metastasizing cancer in a human being. "Cyclic peptides" in the sense of the invention are according to the general knowledge in the field of protein chemistry polypeptide chains wherein the N-terminal amino group and carboxyl group of the C-terminus, the amino group of the N-terminus and an amino acid side chain, the C-terminal carboxyl group and an amino acid side chain, or two amino acid side chains are linked with a covalent bond that generates the ring or circle. Preferably, the cyclic peptides of invention are polypeptide chains wherein at least one covalent bond is selected from a chemical bond between the amino group of the N-terminus and an amino acid side chain, between the C-terminal carboxyl group and an amino acid side chain, or between two amino acid side chains.

The present invention is based to some extent on the experimental findings described hereinafter that a cyclic peptide, such as of amino acid sequence K-R-W-H-E (SEQ ID No. 34) with or without D-amino acid is capable of inhibiting metastasis in a mouse animal model. It thus seems reasonable to assume that the same efficacy can be observed in different metastasizing cancers in human, particularly where these cancers show expression of CD44v6. It was moreover shown that introducing D-amino acids in the cyclic peptide even increases the inhibitory effect of the peptide on cell migration and metastasis. Therefore, it seems reasonable to assume that a cyclic peptide as defined herein and in the claims can be used for cancers in general, preferably metastasizing cancers, angiogenesis related diseases and other related diseases. Tumors observed in the experimental section were smaller and less vascularized demonstrating the effectiveness of the cyclic peptides described herein as anti-angiogenesis reagents. Additionally, the cyclic peptides inhibited cell migration in the wound healing assay (cf. Example 5 (cf. FIG. 5).

The term "peptide" as used herein refers to any compound comprising at least the above mentioned five amino acids.

The term "compound comprising a cyclic peptide" refers to compounds which comprise a cyclic peptide optionally e.g. in the form of a pharmaceutically acceptable salt. The term equally refers to peptides which have been e.g. chemically or enzymatically modified such that the cyclic peptide comprises additional modifications as they are described hereinafter.

The term "compound comprising a peptide" or "compound comprising a cyclic peptide" and its grammatical variation such as "cyclic peptide compound" or "peptide compound" thus includes salts, preferably pharmaceutically acceptable salts of the peptides described herein. Salts encompassed within the term "pharmaceutically acceptable salts" refer to non-toxic salts of the peptide compounds of this invention. Representative salts and esters include the following: acetate, ascorbate, benzenesulfonate, benzoate, bicarbonate, bisulfate, bitartrate, borate, caamsylate, carbonate, citrate, dihydrochloride, methanesulfonate, ethanesulfonate, p-toluenesulfonate, cyclohexylsulfamate, quinate, edetate, edisylate, estolate, esylate, fumarate, gluconate, glutamate, glycerophophates, hydrobromide, hydrochloride, hydroxynaphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, tosylate, trifluoroacetate, and valerate. Other salts include Ca, Li, Mg, Na, and K salts; salts of amino acids such as lysine or arginine; guanidine, diethanolamine or choline; ammonium, substituted ammonium salts or aluminum salts. The salts are prepared by conventional methods.

It is preferred that the peptide component of the invention is an isolated cyclic peptide. The term "isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

It is also preferred that the cyclic peptide of the invention is in a pure state. Preferably, the peptide is ≥80% pure, preferably ≥90% pure, more preferably ≥95% pure, even more preferably ≥99% pure and particularly preferred is a pharmaceutically pure state that is greater than 99.9% pure with respect to contaminating macromolecules, particularly other peptides. It is preferred that the peptide is free of infectious and pyrogenic agents.

Preferably, a purified cyclic peptide is substantially free of other peptides. When used in this context, the term "pure" does not exclude the presence of the same peptide in alternative physical forms, such as dimers.

The peptides of the invention may be prepared by chemical synthesis or by recombinant expression in host cells. The preparation by chemical synthesis is preferred (cf. Examples 1 and 2). As protein products, compounds or any of the other peptides of the present invention are amenable to production by the technique of solution- or solid-phase peptide synthesis. The synthetic peptide synthesis approach generally entails the use of automated synthesizers and appropriate resin as solid phase, to which is attached the C-terminal amino acid of the desired peptide. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984).

The term "peptidomimetic" refers to a small protein-like chain designed to mimic a corresponding peptide. Peptidomimetics can typically arise either from modification of an existing peptide, or by designing similar systems that mimic peptides, such as peptoids and β-peptides. Irrespective of the approach, the altered chemical structure is designed to advantageously adjust the molecular properties such as metabolic stability and bioavailability without negatively affecting biological activity.

Typically a peptidomimetic will have an altered backbone such as a methylated amide group instead of the amide group of a peptide bond to increase the stability of the peptidomimetic against degradation by proteases. Alternatively or in addition, the peptidomimetic may also comprise non-natural amino acids or D-enantiomers. A common theme of peptidomimetics is that the molecular changes in the backbone structure and/or in the amino acids should not have a substantial effect on the overall conformation of the peptidomimetic in comparison to the corresponding peptide in order to not negatively affect the biological activity of the peptidomimetic. Thus, a peptidomimetic is an isostere of the corresponding peptide. Preferred peptidomimetics are e.g. isosteric peptoids, which comprise poly-N-substituted glycines in the peptide bonds of the backbone. In accordance with the invention, peptidomimetic shall therefore have the same activity in the experiments described hereinafter as the peptides as described hereinafter, such as e.g. a peptide of SEQ ID NO. 1-36 or 41-42. The most preferred peptidomimetics are those having five amino acids such as a peptidomimetic of a peptide of SEQ ID No. 37, 6 amino acids (such as a peptidomimetic of SEQ ID NO: 35) or 7 amino acids (cf. SEQ ID NO: 36). Such peptidomimetics are preferably isosteric peptoids, which comprise poly-N-substituted glycines in the peptide bonds of the backbone.

The present invention also contemplates modified forms of cyclic peptides or peptidomimetics. Such modified forms relate e.g. to cyclic peptides or peptidomimetics which have been chemically modified at their amino acid side chains, such as by alkylation such as methylation to reduce degradation of the peptides or peptidomimetics e.g. by proteases and to increase stability thereof. Other modifications include amino acids, amino acid derivatives, or aromatic hydrophobic modifications; wherein optionally the modification comprises phenyl acetic acid or 3-indole acetic acid; acetylating, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, i.e. a cyclic peptide, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, ubiquitination and sumoylation. A typical peptidomimetic can have one or more modification, i.e. can comprise D-amino acids and have an aromatic or hydrophobic modification. Typical examples of peptidomimetics include those which have SEQ ID Nos: 1 to 36 or 41 to 42 with L- and/or D-amino acids.

Cyclization of peptides is performed by methods generally known by a person skilled in the art, such as described in Zitzmann et al. (2005, Journal of Nuclear Medicine, 46(5):782). More detailed information can also be taken from Example 1 and 2.

The compounds of the invention can also be administered in combination with cytotoxic compounds, immunopharmaceuticals, antibodies against a receptor tyrosine kinase (RTK), and/or chemotherapeutic agents, preferably the compound of the invention is administered in combination with a compound selected from the group consisting of an epidermal growth factor receptor (EGFR) inhibitor, preferably selected from the group consisting of gefitinib, erlotinib, lapatinib, cetuximab, panitumumab, vandetanib and mixtures thereof, an hepatocyte growth factor receptor (HGF/c-Met) inhibitor, preferably selected from the group consisting of ficlatuzumab, crizotinib, tivantinib, cabozantinib, capmatinib, MGCD265, volitinib, MK8033, MK-2461, and mixtures thereof, a programmed cell death protein 1 (PD-1) inhibitor, preferably selected from the group consisting of nivolumab/BMS-936558, lambrolizumab, pidilizumab, AMP-224, pembrolizumab and mixtures thereof, a programmed death-ligand 1 (PD-L1) inhibitor, preferably selected from the group consisting of BMS-936559, RG7446/MPDL3280A, MEDI4736, MSB0010718C/Avelumab and mixtures thereof, a cytotoxic T-lymphocyte-associated protein 4 (CTLA-4) inhibitor, preferably ipilimumab, a vascular endothelial growth factor receptor (VEGFR) inhibitors, preferably selected from the group consisting of bevacicumab, pazopanib, sorafenib, sunitinib, axitinib, ponatinib, regorafenib, vandetanib, cabozantinib, lenvatinib, ramucirumab and mixtures thereof, a chemotherapeutic agent, preferably selected from the group consisting of an alkylating agent, preferably selected from the group consisting of a nitrogen mustard, such as mechlorethamine, chlorambucil, cyclophosphamide, ifosfamide and melphalan, nitrosourea, such as streptozocin, carmustine (BCNU) and lomustine, an alkyl sulfonate, such as busulfan, a triazine, such as dacarbazine (DTIC) and temozolomide, an ethylenimine, such as thiotepa and altretamine (hexamethylmelamine), and mixtures thereof, a platinum drug, preferably selected from the group consisting of cisplatin, carboplatin, oxalaplatin and a mixture thereof, an antimetabolite, preferably selected from the group consisting of 5-fluorouracil (5-FU), 6-mercaptopurine (6-MP), capecitabine, cytarabine, floxuridine, fludarabine, gemcitabine, hydroxyurea, methotrexate, pemetrexed, and mixtures thereof, an taxane, an eribulin, folfirinox, folfox, an anthracycline, preferably selected from the group consisting of daunorubicin, doxorubicin, epirubicin, idarubicin and a mixture thereof and a mixture thereof and combinations thereof. In addition or alternatively preferred modified forms of peptides or peptidomimetics in accordance with the invention include e.g. chemically or enzymatically modified forms thereof which have improved biological properties such as improved solubility, absorption, biological half-life, etc. The modifications may alternatively decrease the toxicity of the molecule, eliminate or attenuate any undesirable side effect of the molecule, etc. Modifications which increase e.g. the biological half-life include pegylation, hesylation, pasylation, glycosylation with glycosyl structure having sialic acid residues at their end, etc.

Below it is set out how the compounds in accordance with the present invention, i.e. the cyclic peptides, peptidomimetics thereof and modified forms thereof, the pharmaceutical compositions comprising these compounds and methods making use of these compounds may be used for the treatment of cancer, an angiogenesis related disease, a disease from the field of ophthalmology, diseases associated with an increased invasive potential of cells, and inflammatory disorders in a human being, preferably metastasizing cancer in a human being. It is to be understood that, whenever reference is made in the following to the treatment of metastasizing cancer, this reference, as a preferred embodiment, always contemplates to use the cyclic peptides as described hereinafter, preferably those of SEQ ID NO:34 or 41-42, SEQ ID NO:35 and SEQ ID NO:36.

As can be taken from the experiments described hereinafter, the cyclic peptides used in the experiments were capable of inhibiting metastasis formation in adenocarcinoma models. As mentioned, the invention further relates to the use of compounds, pharmaceutical compositions and the application of methods as described herein for the treatment of metastasizing cancers.

Metastasizing cancers in accordance with the invention include metastasizing forms of cancers for which expression of CD44v6 has been observed on cancer tissues or can be observed upon corresponding testing e.g. with CD44v6 antibodies. Thus, in order to see whether a patient is eligible for treatment with compounds and pharmaceutical compositions as described herein, one may take a biopsy of tumor tissue and test for expression of CD44v6. If the tumor can be shown to express CD44v6 and if metastases have started to form or have already formed and maybe even spread through the body, this tumor is considered as a metastasizing cancer in accordance with the invention. Metastasizing cancers in accordance with the invention include metastasizing forms of Hodgkin lymphoma, colorectal cancer, cervical cancer, lung cancer, skin cancer such as squamous cell cancer or basal cell carcinoma, head and neck cancer, gastric cancer, pancreatic cancer, head and neck squamous cell cancer, breast cancer, and others.

Such metastasizing cancer forms of the various cancers such as Hodgkin lymphoma, colorectal cancer, cervical cancer, lung cancer, skin cancer such as squamous cell cancer or basal cell carcinoma, head and neck cancer, gastric cancer, pancreatic cancer and breast cancer can be identified according to the TNM Anatomic Stage/Prognostic Group System of the Cancer Staging Manual of the American Joint Committee on Cancer ($7^{th}$ edition, 2010, Springer).

Metastasizing cancers in accordance with the invention may be classified as Stage III or Stage IV cancers according to the TNM Anatomic Stage/Prognostic Group System of the Cancer Staging Manual of the American Joint Committee on Cancer (7$^{th}$ edition, 2010, Springer). The TNM (tumor node metastasis) staging system of the American Joint Committee on Cancer allows staging, i.e. classification of cancers by the size and extent of the primary tumor (T), the question if regional lymph nodes (N) are affected and if distant metastases can already be detected (M). This indication is then typically taken as an indication for different routes to take in treating the patient and also allows a reliable prognosis of the diseases. This is why the TNM system has become an indispensable tool for oncologists.

The parameter M receives a value of 0, i.e. M0 if no distant metastases can be detected clinically although they may have started to develop. If M is set at M0, a patient depending on the values of T and N may be classified as Stage III. Thus for e.g. any T, N3 and M0, a patient may be classified as Stage III, or Stage IIIc in case of e.g. breast cancer (see page 362, Cancer Staging Manual of the American Joint Committee on Cancer (7$^{th}$ edition, 2010, Springer). If such a Stage III patient or a patient having the highest subclass of Stage III (such as Stage IIIC for breast cancer) additionally displays circulating tumor cells and micrometastases in the bone marrow, this will worsen the prognosis. Thus, for the purposes of the present invention a metastasizing cancer may be classifiable as Stage III according to the TNM Anatomic Stage/Prognostic Group System of the Cancer Staging Manual of the American Joint Committee on Cancer (7$^{th}$ edition, 2010, Springer).

Preferably, for a metastasizing cancer in accordance with the invention M is Ml, i.e. that distant metastasis can be clinically detected so that such a metastasizing tumor can be classified as Stage IV according to the TNM Anatomic Stage/Prognostic Group System of the Cancer Staging Manual of the American Joint Committee on Cancer (7$^{th}$ edition, 2010, Springer).

It is to be understood that wherever the present invention makes reference to a metastasizing cancer, this most preferably relates to a cancer such as Hodgkin lymphoma, colorectal cancer, cervical cancer, lung cancer, skin cancer such as squamous cell cancer or basal cell carcinoma, head and neck cancer, gastric cancer, pancreatic cancer, or breast cancer, which is classified as Stage IV according to the TNM Anatomic Stage/Prognostic Group System of the Cancer Staging Manual of the American Joint Committee on Cancer (7$^{th}$ edition, 2010, Springer). The specific requirements for classifying each cancer according to this system, which can be found in the respective chapters of the Cancer Staging Manual of the American Joint Committee on Cancer (7$^{th}$ edition, 2010, Springer), see e.g. page 143 to 146 for colorectal cancer, page 241 to 250 for pancreatic cancer, page 301 to 314 for squamous cell cancer, page 347 to 376, etc.), are hereby incorporated by reference.

A particularly preferred embodiment thus refers to the use of the cyclic peptides described hereinafter, e.g. of SEQ ID NO:19-36 or 41-42 and most preferably of SEQ ID NO:34-36 or 41-42, peptidomimetics thereof or modified forms thereof, and pharmaceutical compositions comprising these compounds for the treatment of metastasizing cancers such as Hodgkin lymphoma, colorectal cancer, cervical cancer, lung cancer, skin cancer such as squamous cell cancer or basal cell carcinoma, head and neck cancer, gastric cancer, pancreatic cancer, or breast cancer, which are classifiable as Stage IV according to the Cancer Staging Manual of the American Joint Committee on Cancer.

The compounds and salts thereof can be formulated as mentioned above as pharmaceutical compositions (e.g. liquids, suspensions, emulsions, lozenges, sachets, ampoules, aerosols, powders, granules, tablets, pills, capsules, injections, solutions etc.) comprising at least one such compound alone or optionally in a mixture with pharmaceutically acceptable carriers, excipients and/or diluents.

The compounds/salts thereof and pharmaceutical compositions may be formulated for intravenous or oral administration, e.g. by inhalation, for nasal administration or for administration by injection such as subcutaneous injection.

The following paragraphs are preferred embodiments of the invention:

1. A compound comprising:
    a cyclic peptide comprising at least
    (a) an amino acid $X_1$ being selected from the group consisting of A, C, D, E, F, G, H, I, K, L, M, N, P, Q, R, S, T, V, W, and Y, further
    (b) an amino acid sequence R-W-H, and further
    (c) an amino acid $X_{11}$ being selected from the group consisting of A, C, D, E, F, G, H, I, K, L, M, N, P, Q, R, S, T, V, W, and Y, or a peptidomimetic thereof, or
    a cyclic peptide comprising at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein the amino acid $X_1$ is selected from the group consisting of A, C, D, E, F, G, H, I, K, L, M, N, P, Q, R, S, T, V, W, and Y, wherein the amino acids $X_2$, $X_3$, $X_4$, $X_5$, $X_6$, $X_7$, $X_{11}$, $X_{12}$, $X_{13}$, and $X_{14}$ are independently selected from the group consisting of A, C, D, E, F, G, H, I, K, L, M, N, P, Q, R, S, T, V, W, and Y, and wherein $X_2$, $X_3$, $X_4$, $X_5$, $X_6$, $X_7$, $X_{12}$, $X_{13}$, and $X_{14}$ are optionally present in the amino acid sequence, or a peptidomimetic thereof.

2. The compound of paragraph 1, wherein the amino acid $X_1$ is an amino acid having an $NH_2$ group, such as K, R, N, or Q, and/or
    wherein $X_2$ is optionally present and optionally selected from the group consisting of amino acids with negatively charged side chains such as E or D, or amino acids with non-polar side chains such as A, V, L or I, wherein $X_3$ is optionally present and optionally selected from the group consisting of amino acids with an $NH_2$ group such as K, R, N, or Q, and amino acids with non-polar side chains such as A, V, L or I, wherein $X_4$ is optionally present and optionally selected from the group consisting of amino acids with non-polar or non-charged side changes and aromatic ring structures such as F, W, or Y, and amino acids with non-polar side chains such as A, V, L or I, wherein $X_5$ is optionally present and optionally selected from the group consisting of amino acids with non-polar or non-charged side changes and aromatic rings structures such as F, W, or Y, and amino acids with non-polar side chains such as A, V, L or I, wherein $X_6$ is optionally present and optionally selected from the group consisting of G and amino acids with non-polar side chains such as A, V, L or I, wherein $X_7$ is optionally present and optionally selected from the group consisting of amino acids with an $NH_2$ group such as K, R, N, or Q, and amino acids with non-polar side chains such as A, V, L or I, wherein $X_{11}$ is selected from the group consisting of amino acids with negatively charged side chains such as E or D, and amino acids with non-polar side chains such as A, V, L or I, wherein $X_{12}$ is optionally present and optionally selected from the group consisting of G and amino acids with non-polar side chains such as A, V, L or I, wherein $X_{13}$ is optionally present and optionally selected from the group consisting of amino acids with non-polar or non-charged side chains and aromatic rings structures such F, W, or Y, and amino acids with non-polar side chains such as A, V, L or I, and wherein $X_{14}$ is optionally present and optionally selected from the group consisting of amino acids with an NH$_2$ group such as K, R, N, or Q, and amino acids with non-polar side chains such as A, V, L or I.

3. The compound of paragraph 1 or 2,
wherein X$_1$ is selected from the group consisting of K, R, N, and Q, wherein X$_2$ is optionally present and optionally selected from the group consisting of amino acids E and D, wherein X$_3$ is optionally present and optionally selected from the group consisting of amino acids K, R, N, and Q, wherein X$_4$ is optionally present and optionally selected from the group consisting of amino acids F, W, and Y, wherein X$_5$ is optionally present and optionally selected from the group consisting of amino acids F, W, and Y, wherein X$_6$ is optionally present and optionally selected from the group consisting of amino acids G, A, V, L and I, wherein X$_7$ is optionally present and optionally selected from the group consisting of amino acids K, R, N, and Q, wherein X$_{11}$ is present and optionally E or D, wherein X$_{12}$ is optionally present and optionally selected from the group consisting of amino acids G, A, V, L and I, wherein X$_{13}$ is optionally present and optionally selected from the group consisting of amino acids F, W, and Y, and wherein X$_{14}$ is optionally present and optionally selected from the group consisting of amino acids K, R, N, and Q.

4. The compound of any one of the preceding paragraphs, wherein the cyclic peptide comprises at least the amino acid sequence X$_1$-X$_2$-X$_3$-X$_4$-X$_5$-X$_6$-X$_7$-R-W-H-X$_{11}$-X$_{12}$-X$_{13}$-X$_{14}$, wherein X$_1$ is present and optionally selected from the group consisting of K, R, N, and Q, preferably K, wherein X$_2$ is optionally present and optionally selected from the group consisting of amino acids E and D, wherein X$_3$ is optionally present and optionally selected from the group consisting of amino acids K, R, N, and Q, wherein X$_4$ is optionally present and optionally selected from the group consisting of amino acids F, W, and Y, wherein X$_5$ is optionally present and optionally selected from the group consisting of amino acids F, W, and Y, wherein X$_6$ is optionally present and optionally selected from the group consisting of amino acids G, A, V, L and I, wherein X$_7$ is present and optionally selected from the group consisting of amino acids K, R, N, and Q, wherein X$_{11}$ is present and E or D, wherein X$_{12}$ is optionally present and optionally selected from the group consisting of amino acids G, A, V, L and I, wherein X$_{13}$ is optionally present and optionally selected from the group consisting of amino acids F, W, and Y, and wherein X$_{14}$ is optionally present and optionally selected from the group consisting of amino acids K, R, N, and Q, or a peptidomimetic thereof.

5. The compound of any one of the preceding paragraphs, wherein the cyclic peptide comprises at least the amino acid sequence X$_1$-X$_2$-X$_3$-X$_4$-X$_5$-X$_6$-X$_7$-R-W-H-X$_{11}$-X$_{12}$-X$_{13}$-X$_{14}$, wherein X$_1$ is present and optionally selected from the group consisting of K, R, N, and Q, preferably K, wherein X$_2$ is optionally present and optionally selected from the group consisting of amino acids E and D, wherein X$_3$ is optionally present and optionally selected from the group consisting of amino acids K, R, N, and Q, wherein X$_4$ is optionally present and optionally selected from the group consisting of amino acids F, W, and Y, wherein X$_5$ is optionally present and optionally selected from the group consisting of amino acids F, W, and Y, wherein X$_6$ is present and optionally selected from the group consisting of amino acids G, A, V, L and I, wherein X$_7$ is present and optionally selected from the group consisting of amino acids K, R, N, and Q, wherein X$_{11}$ is present and E or D, wherein X$_{12}$ is optionally present and optionally selected from the group consisting of amino acids G, A, V, L and I, wherein X$_{13}$ is optionally present and optionally selected from the group consisting of amino acids F, W, and Y, and wherein X$_{14}$ is optionally present and optionally selected from the group consisting of amino acids K, R, N, and Q, or a peptidomimetic thereof.

6. The compound of any one of the preceding paragraphs, wherein the cyclic peptide comprises at least the amino acid sequence X$_1$-X$_2$-X$_3$-X$_4$-X$_5$-X$_6$-X$_7$-R-W-H-X$_{11}$-X$_{12}$-X$_{13}$-X$_{14}$, wherein X$_1$ is present and optionally selected from the group consisting of K, R, N, and Q, preferably K, wherein X$_2$ is optionally present and optionally selected from the group consisting of amino acids E and D, wherein X$_3$ is optionally present and optionally selected from the group consisting of amino acids K, R, N, and Q, wherein X$_4$ is optionally present and optionally selected from the group consisting of amino acids F, W, and Y, wherein X$_5$ is present and optionally selected from the group consisting of amino acids F, W, and Y, wherein X$_6$ is present and optionally selected from the group consisting of amino acids G, A, V, L and I, wherein X$_7$ is present and optionally selected from the group consisting of amino acids K, R, N, and Q, wherein X$_{11}$ is E or D, wherein X$_{12}$ is optionally present and optionally selected from the group consisting of amino acids G, A, V, L and I, wherein X$_{13}$ is optionally present and optionally selected from the group consisting of amino acids F, W, and Y, and wherein X$_{14}$ is optionally present and optionally selected from the group consisting of amino acids K, R, N, and Q, or a peptidomimetic thereof.

7. The compound of any one of the preceding paragraphs, wherein the cyclic peptide comprises at least the amino acid sequence X$_1$-X$_2$-X$_3$-X$_4$-X$_5$-X$_6$-X$_7$-R-W-H-X$_{11}$-X$_{12}$-X$_{13}$-X$_{14}$, wherein X$_1$ is present and optionally selected from the group consisting of K, R, N, and Q, preferably K, wherein X$_2$ is optionally present and optionally selected from the group consisting of amino acids E and D, wherein X$_3$ is optionally present and optionally selected from the group consisting of amino acids K, R, N, and Q, wherein X$_4$ is present and optionally selected from the group consisting of amino acids F, W, and Y, wherein X$_5$ is present and optionally selected from the group consisting of amino acids F, W, and Y, wherein X$_6$ is present and optionally selected from the group consisting of amino acids G, A, V, L and I, wherein X$_7$ is present and optionally selected from the group consisting of amino acids K, R, N, and Q, wherein X$_{11}$ is present and optionally E or D, wherein X$_{12}$ is optionally present and optionally selected from the group consisting of amino acids G, A, V, L and I, wherein X$_{13}$ is optionally present and optionally selected from the group consisting of amino acids F, W, and Y, and wherein X$_{14}$ is optionally present and optionally selected from the group consisting of amino acids K, R, N, and Q, or a peptidomimetic thereof.

8. The compound of any one of the preceding paragraphs, wherein the cyclic peptide comprises at least the amino acid sequence X$_1$-X$_2$-X$_3$-X$_4$-X$_5$-X$_6$-X$_7$-R-W-H-X$_{11}$-X$_{12}$-X$_{13}$-X$_{14}$, wherein X$_1$ is present and optionally selected from the group consisting of K, R, N, and Q, preferably K, wherein X$_2$ is optionally present and optionally selected from the group consisting of amino acids E and D, wherein X$_3$ is present and optionally selected from the group consisting of amino acids K, R, N, and Q, wherein X$_4$ is present and optionally selected from the group consisting of amino acids F, W, and Y, wherein X$_5$ present and is optionally selected from the group consisting of amino acids F, W, and Y, wherein X$_6$ is present and optionally selected from the group consisting of amino acids G, A, V, L and I, wherein X$_7$ is selected from the group consisting of amino acids K, R, N, and Q, wherein X$_{11}$ is present and optionally E or D, wherein $X_{12}$ is optionally present and optionally selected from the group consisting of amino acids G, A, V, L and I, wherein $X_{13}$ is optionally present and optionally selected from the group consisting of amino acids F, W, and Y, and wherein $X_{14}$ is optionally present and optionally selected from the group consisting of amino acids K, R, N, and Q, or a peptidomimetic thereof.

9. The compound of any one of the preceding paragraphs, wherein the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is present and optionally selected from the group consisting of amino acids E and D, wherein $X_3$ is present and optionally selected from the group consisting of amino acids K, R, N, and Q, wherein $X_4$ is present and optionally selected from the group consisting of amino acids F, W, and Y, wherein $X_5$ is present and is optionally selected from the group consisting of amino acids F, W, and Y, wherein $X_6$ is present and optionally selected from the group consisting of amino acids G, A, V, L and I, wherein $X_7$ is present and optionally selected from the group consisting of amino acids K, R, N, and Q, wherein $X_{11}$ is present and optionally E or D, wherein $X_{12}$ is optionally present and optionally selected from the group consisting of amino acids G, A, V, L and I, wherein $X_{13}$ is optionally present and optionally selected from the group consisting of amino acids F, W, and Y, and wherein $X_{14}$ is optionally present and optionally selected from the group consisting of amino acids K, R, N, and Q, or a peptidomimetic thereof.

10. The compound of any one of the preceding paragraphs, wherein the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is present and optionally selected from the group consisting of amino acids E and D, wherein $X_3$ is present and is optionally selected from the group consisting of amino acids K, R, N, and Q, wherein $X_4$ is present and is optionally selected from the group consisting of amino acids F, W, and Y, wherein $X_5$ is present and optionally selected from the group consisting of amino acids F, W, and Y, wherein $X_6$ is present and is optionally selected from the group consisting of amino acids G, A, V, L and I, wherein $X_7$ is present and optionally selected from the group consisting of amino acids K, R, N, and Q, wherein $X_{11}$ is optionally E or D, wherein $X_{12}$ is present and optionally selected from the group consisting of amino acids G, A, V, L and I, wherein $X_{13}$ is optionally present and optionally selected from the group consisting of amino acids F, W, and Y, and wherein $X_{14}$ is optionally present and optionally selected from the group consisting of amino acids K, R, N, and Q, or a peptidomimetic thereof.

11. The compound of any one of the preceding paragraphs, wherein the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$, wherein $X_1$ is present and optionally selected from the group consisting of K, R, N, and Q, preferably K, wherein $X_2$ is present and optionally selected from the group consisting of amino acids E and D, wherein $X_3$ is present and is optionally selected from the group consisting of amino acids K, R, N, and Q, wherein $X_4$ is present and optionally selected from the group consisting of amino acids F, W, and Y, wherein $X_5$ is present and optionally selected from the group consisting of amino acids F, W, and Y, wherein $X_6$ is present and optionally selected from the group consisting of amino acids G, A, V, L and I, wherein $X_7$ is present and optionally selected from the group consisting of amino acids K, R, N, and Q, wherein $X_{11}$ is present and optionally E or D, wherein $X_{12}$ is present and optionally selected from the group consisting of amino acids G, A, V, L and I, wherein $X_{13}$ is present and optionally selected from the group consisting of amino acids F, W, and Y, and wherein $X_{14}$ is optionally present and optionally selected from the group consisting of amino acids K, R, N, and Q, or a peptidomimetic thereof.

12. The compound of any one of the preceding paragraphs, wherein the cyclic peptide comprises at least the amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is present and optionally selected from the group consisting of K, R, N, and Q, preferably K, wherein $X_2$ is present and optionally selected from the group consisting of amino acids E and D, wherein $X_3$ is present and is optionally selected from the group consisting of amino acids K, R, N, and Q, wherein $X_4$ is present and optionally selected from the group consisting of amino acids F, W, and Y, wherein $X_5$ is present and optionally selected from the group consisting of amino acids F, W, and Y, wherein $X_6$ is present and optionally selected from the group consisting of amino acids G, A, V, L and I, wherein $X_7$ is present and optionally selected from the group consisting of amino acids K, R, N, and Q, wherein $X_{11}$ is present and optionally E or D, wherein $X_{12}$ is present and optionally selected from the group consisting of amino acids G, A, V, L and I, wherein $X_{13}$ is present and optionally selected from the group consisting of amino acids F, W, and Y, and wherein $X_{14}$ is present and is optionally selected from the group consisting of amino acids K, R, N, and Q, or a peptidomimetic thereof.

13. The compound of any one of the preceding paragraphs, wherein $X_1$ is selected from the group consisting of K, R, N, and Q, preferably K, wherein $X_2$, if present, is selected from the group consisting of amino acids E and D, wherein $X_3$, if present, is selected from the group consisting of amino acids K, R, N, and Q, wherein $X_4$, if present, is selected from the group consisting of amino acids F, W, and Y, wherein $X_5$, if present, is selected from the group consisting of amino acids F, W, and Y, wherein $X_6$, if present, is selected from the group consisting of amino acids G, A, V, L and I, wherein $X_7$, if present, is selected from the group consisting of amino acids K, R, N, and Q, wherein $X_{11}$ is D or E, wherein $X_{12}$, if present, is selected from the group consisting of amino acids G, A, V, L and I, wherein $X_{13}$, if present, is selected from the group consisting of amino acids F, W, and Y, and wherein $X_{14}$, if present, is selected from the group consisting of amino acids K, R, N, and Q.

14. The compound of any one of the preceding paragraphs, wherein $X_1$ is K, wherein $X_2$, if present, is E, wherein $X_3$, if present, is Q, wherein $X_4$, if present, is W, wherein $X_5$, if present, is F, wherein $X_6$, if present, is G, wherein $X_7$, if present, is N, wherein $X_{11}$ is E, wherein $X_{12}$, if present, is G, wherein $X_{13}$, if present, is Y, and wherein $X_{14}$, if present, is R.

15. The compound of any one of the preceding paragraphs, wherein the cyclic peptide comprises, optionally consists of, the amino acid sequence K-R-W-H-E (SEQ ID No.: 34), K-N-R-W-H-E (SEQ ID No.: 35), K-G-N-R-W-H-E (SEQ ID No: 36), or a peptidomimetic thereof.

16. The compound of any one of the preceding paragraphs, wherein said peptide does not comprise the amino acid sequence N-R-W-H-E (SEQ ID No.: 2), the amino acid sequence K-R-W-H-E (SEQ ID NO: 34) and a DOTA modification, the amino acid sequence K-G-N-R-W-H-E-G (SEQ ID NO: 18), the amino acid sequence K-E-Q-W-F-G-N-R-W-H-E-G-Y-R (SEQ ID No.: 6), or a peptidomimetic thereof.

17. The compound of any one of the preceding paragraphs, wherein the cyclic peptide or peptidomimetic thereof comprises a modification.

18. The compound of paragraph 17, wherein the modification comprises an amino acid, amino acid derivative, a lipophilic modification, or an aromatic hydrophobic modification, optionally the modification comprises phenyl acetic acid or 3-indole acetic acid.

19. The compound of paragraph 17 or 18, wherein the modification is not DOTA or a myristoyl group.

20. The compound of any one of the preceding paragraphs, comprising a chemical bond between two adjacent amino acids of the cyclic peptide which is not a chemical bond between the N-terminus of the a amino acid and the C-terminus of a second amino acid of the two adjacent amino acids.

21. The compound of paragraph 20, wherein the chemical bond between the two adjacent amino acids involves the amino acid side chain of at least one of said two adjacent amino acids.

22. The compound of any one of the preceding paragraphs, wherein the cyclic peptide comprises a chemical bond selected from the group consisting of a chemical bond between an N-terminal amino group of an amino acid and an amino acid side chain, a chemical bond between a C-terminal carboxyl group of an amino acid and an amino acid side chain, and a chemical bond between an amino acid side chain of a first amino acid of the peptide and an amino acid side chain of a second amino acid of the peptide.

23. The compound of any one of the preceding paragraphs, wherein the cyclic peptide comprises a chemical bond selected from the group consisting of a chemical bond between an N-terminal amino group of an amino acid and a carboxyl group of an amino acid side chain, preferably of E or D, a chemical bond between a C-terminal carboxyl group of an amino acid and an amino group of an amino acid side chain, preferably of K, R, N or Q, and a chemical bond between an amino group of an amino acid side chain of a first amino acid of the peptide, preferably of K, R, N or Q, and a carboxyl group of an amino acid side chain of a second amino acid of the peptide, preferably of E or D.

24. The compound of any one of the preceding paragraphs, wherein the peptide has the amino acid sequence K-R-W-H-E (SEQ ID No.: 34), K-N-R-W-H-E (SEQ ID No.: 35) or K-G-N-R-W-H-E (SEQ ID NO.: 36), comprising a chemical bond selected from the group consisting of a chemical bond between an N-terminal amino group of an amino acid and an amino acid side chain, optionally a carboxyl group of an amino acid side chain, a chemical bond between a C-terminal carboxyl group of an amino acid and an amino acid side chain, optionally an amino group of an amino acid side chain, and a chemical bond between an amino acid side chain of a first amino acid of the peptide and an amino acid side chain of a second amino acid of the peptide, optionally between a carboxyl group of the amino acid side chain of the first amino acid and an amino group of the amino acid side chain of the second amino acid.

25. The compound of paragraph 23, wherein the peptide has the amino acid sequence K-R-W-H-E (SEQ ID No.: 34) and comprises a chemical bond between an N-terminal amino group of an amino acid and an amino acid side chain, preferably between an N-terminal amino group of an amino acid and a carboxyl group of an amino acid side chain, optionally of E.

26. The compound of any one of paragraphs 21 to 25, wherein the amino acid side chain is the amino acid side chain of an amino acid selected from the group consisting of the amino acids E, D, K, R, N and Q.

27. The compound of any one of paragraphs 20 to 26, wherein the chemical bond comprises the carboxyl group of an amino acid side chain of an amino acid E or D and/or wherein the chemical bond comprises the amino group of an amino acid side chain of any one of the amino acids K, R, N or Q.

28. The compound of any one of paragraphs 21 to 27, wherein the amino acid side chain is modified or truncated.

29. The compound of any one of the preceding paragraphs, wherein at least one amino acid of the cyclic peptide is a D-amino acid.

30. The compound of paragraph 29, wherein 2, 3, 4, 5, 6, 7, 8, 9, 10, 11, 12, 13 or 14 amino acids are D-amino acids.

31. The compound of any one of the preceding paragraphs, wherein at least one amino acid of the amino acid sequence R-W-H is a D-amino acid.

32. The compound of any one of paragraph 31, wherein at least W is a D-amino acid.

33. The compound of any one of the preceding paragraphs, wherein W is a D-amino acid.

34. The compound of any one of the preceding paragraphs, wherein the peptide has the amino acid sequence K-R-W-H-E (SEQ ID No.: 34), K-N-R-W-H-E (SEQ ID No.: 35) or K-G-N-R-W-H-E (SEQ ID NO.: 36), comprising a chemical bond selected from the group consisting of a chemical bond between an N-terminal amino group of an amino acid and an amino acid side chain, optionally a carboxyl group of an amino acid side chain, a chemical bond between a C-terminal carboxyl group of an amino acid and an amino acid side chain, optionally an amino group of an amino acid side chain, and a chemical bond between an amino acid side chain of a first amino acid of the peptide and an amino acid side chain of a second amino acid of the peptide, optionally between a carboxyl group of the amino acid side chain of the first amino acid and an amino group of the amino acid side chain of the second amino acid, wherein at least one amino acid is a D-amino acid, preferably at least one amino acid of the amino acid sequence R-W-H is a D-amino acid.

35. The compound of any one of the preceding paragraphs, wherein the peptide has the amino acid sequence K-R-W-H-E (SEQ ID No.: 34) comprising a chemical bond between an N-terminal amino group of an amino acid and an amino acid side chain, preferably a carboxyl group of an amino acid side chain, more preferably between the N-terminal amino group of K and the carboxyl group of the amino acid side chain of E, wherein at least one amino acid is a D-amino acid, preferably at least one amino acid of the amino acid sequence R-W-H is a D-amino acid.

36. The compound of any one of the preceding paragraphs, wherein the peptide has the amino acid sequence K-R-W-H-E (SEQ ID No.: 41) comprising a chemical bond between the N-terminal amino group of K and the carboxyl group of the amino acid side chain of E, and wherein W is a D-amino acid.

37. A pharmaceutical composition comprising the compound of any one of the preceding paragraphs and a pharmaceutically acceptable carrier.

38. The compound of any one of paragraphs 1 to 36 or the pharmaceutical composition of paragraph 37, wherein the compound is formulated for intravenous, oral, nasal, or subcutaneous administration.

39. The compound of any one of paragraphs 1 to 36 or 38 or the pharmaceutical composition of paragraph 37 or 38 for use as a medicament.

40. The compound of any one of paragraphs 1 to 36, 38 or 39 or the pharmaceutical composition of any one of the preceding paragraphs 37 to 39 for use in treating a disease selected from the group consisting of cancer, an angiogenesis related disease, a disease from the field of ophthalmology, diseases associated with an increased invasive potential of cells, and inflammatory disorders in a human being.

41. The compound of paragraph 40 or the pharmaceutical composition of paragraph 40, wherein the cancer is a metastasizing cancer.

42. The compound of paragraph 40 or 41, or the pharmaceutical composition of paragraph 40 or 41, wherein the disease is selected from the group consisting of estrogen receptor-dependent breast cancer, estrogen receptor-independent breast cancer, hormone receptor-dependent prostate cancer, hormone receptor-independent prostate cancer, brain cancer, renal cancer, colon cancer, familial adenomatous polyposis (FAP), colorectal cancer, pancreatic cancer, bladder cancer, esophageal cancer, stomach cancer, genitourinary cancer, gastrointestinal cancer, uterine cancer, ovarian cancer, astrocytomas, gliomas, skin cancer, squamous cell carcinoma, Keratoakantoma, Bowen disease, cutaneous T-Cell Lymphoma, melanoma, basal cell carcinoma, actinic keratosis; ichtiosis; acne, acne vulgaris, sarcomas, Kaposi's sarcoma, osteosarcoma, head and neck cancer, small cell lung carcinoma, non-small cell lung carcinoma, leukemia, lymphomas and/or other blood cell cancers, thyroid resistance syndrome, diabetes, thalassemia, cirrhosis, protozoal infection, rheumatoid arthritis, rheumatoid spondylitis, all forms of rheumatism, osteoarthritis, gouty arthritis, multiple sclerosis, insulin dependent diabetes mellitus, non-insulin dependent diabetes, asthma, rhinitis, uveithis, lupus erythematoidis, ulcerative colitis, Morbus Crohn, inflammatory bowel disease, chronic diarrhea, psoriasis, atopic dermatitis, bone disease, fibroproliferative disorders, atherosclerosis, aplastic anemia, DiGeorge syndrome, Graves' disease, epilepsia, status epilepticus, alzheimer's disease, depression, schizophrenia, schizoaffective disorder, mania, stroke, mood-incongruent psychotic symptoms, bipolar disorder, affective disorders, meningitis, muscular dystrophy, multiple sclerosis, agitation, cardiac hypertrophy, heart failure, reperfusion injury, diabetic retinopathy, age-related macular degeneration, and obesity in a human being.

43. The compound of any one of paragraphs 40 to 42 or pharmaceutical composition for use of any one of paragraphs 40 to 42, wherein said cancer shows expression of CD44v6.

44. The compound of any one of paragraphs 40 to 43 or pharmaceutical composition for use of any one of paragraphs 40 to 43, wherein said cancer is classifiable as Stage III or Stage IV according to the TNM anatomic/prognostic group system of the cancer staging system of the American Joint Committee on Cancer.

45. The compound of any one of paragraphs 40 to 43 or pharmaceutical composition for use of any one of paragraphs 40 to 43, wherein said cancer is classifiable as Stage IV according to the TNM anatomic/prognostic group system of the cancer staging system of the American Joint Committee on Cancer.

46. The compound for use of any of paragraphs 40 to 45 or pharmaceutical composition for use of any of paragraphs 40 to 45, wherein said cancer is a metastasizing cancer selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, pancreatic cancer, head and neck squamous cell cancer, and breast cancer.

47. The compound for use of any of paragraphs 40 to 46 or pharmaceutical composition for use of any of paragraphs 40 to 46, wherein said cancer is a metastasizing cancer selected from the group consisting of metastasizing forms of Hodgkin lymphoma, colorectal cancer, cervical cancer, lung cancer, skin cancer such as squamous cell cancer or basal cell carcinoma, head and neck cancer, gastric cancer, pancreatic cancer, and breast cancer, wherein said metastasizing cancer is classifiable as Stage IV according to the TNM anatomic/prognostic group system of the cancer staging system of the American Joint Committee on Cancer, and wherein said metastasizing cancer shows expression of CD44v6.

The invention is now described with respect to experiments which, however, are not to be construed in a limiting sense.

EXAMPLES

Example 1—Synthesis Protocol of D3alga1 (Cf. FIGS. 1 and 9) by Solid Phase Cyclisation Resin loading: 200 mg (ca. 320 µmol) 2-chlorotrityl chloride (Iris Biotech GmbH, Marktredwitz, Germany; Code BR-1060) in a filter equipped 5 mL-syringe are swelled with ca. 3 mL of dichloromethane for 10 min; excess solvent is removed before incubation with 40.9 mg (100 µmol) Fmoc-Glu(OA11)-OH and 70 µL (51.9 mg, 402 µmol) DIPEA in 2 mL dichloromethane for 90 min; then capping with 10% methanol, 5% DIPEA in dichloromethane for 2×10 min; final washing with each 2×DMF, dichloromethane & diethylether followed by (short) drying on vacuum line.

SPPS: Resin is transferred to a reaction vessel (ABI 433A), using standard FastmocUV0.05 mmol-chemistry (solvent: NMP; amino acids: each 500 µmol weighed in cartridges; HBTU-activation; base: DIPEA; deprotection: 20% piperidinein NMP) building blocks used: Fmoc-Lys(Boc)-OH, Fmoc-Arg(Pbf)-OH, Fmoc-D-Trp(Boc)-OH, Fmoc-His(Trt)-OH (all obtained from Orpegen Peptide Chemicals GmbH, Heidelberg, Germany); 158 mg (300 µmol) Fmoc-D-Trp(Boc)-OH are activated with 110 mg (290 µmol) HATU, which are weighed in one amino acid cartridge, then standard amount DIPEA is added and coupling time is elongated by 15 min; final Fmoc-deprotection.

OA11-deprot.: Product resin is transferred to a filter equipped 5 mL-syringe and swollen in dichloromethane; excess solvent is removed before incubation with ca. 5 mg (ca. 4 µmol) palladium-tetrakis(triphenylphosphine) and ca. 50 mg (ca. 850 µmol) dimethylamine borane in 2 mL dichloromethane for 25 min in the stoppered syringe; solution is removed, resin washed with dichloromethane and incubated 2×5 min with 3 mL of 5% 2-aminoethanol in dichloromethane in the stoppered syringe; washing with each 3× dichloromethane, NMP, methanol, dichloromethane and diethyl ether.

Cyclisation: (Next day) the resin is swollen in dichloromethane and washed with NMP 3×3 mL; after removal of excess solvent 130 mg (250 µmol) PyAOP in 2 mL NMP are added; 5 min later 100 µL (74.2 mg, 574 µmol) DIPEA in 500 µL NMP are added and the whole reaction mixture is shaken for 30 min; resin is washed each 3×NMP, methanol, dichloromethane and diethyl ether before drying on vacuum line (300 mg product resin).

Deprotection: Dried resin is directly treated with 5 mL of 2.5% water, 2.5% triisopropylsilane in TFA for 45 min; after filtration TFA is removed by coevaporation with 2×20 mL dichloromethane; raw peptide is precipitated and washed with diethylether, collected by centrifugation and dried in vacuo (ca. 70 mg).

Purification: Raw peptide is taken up in 5 mL water and heated to 45° C. for 90 min before separation on a waters XBridge BEH130Prep C18 (5 μm, 19×150 mm) column; gradient: 8-20% acetonitrile/water (0.1% TFA) in 10 min flow: 20 mL/min; ambient temperature.

Yield: 21.65 mg (29.4 μmol; 29.4% based on resin loading) after lyophilisation.

Gradient: 0-66% acetonitrile/water (0.05% TFA) in 20 min; Thermo Scientific Hypersil gold (1.9 μm 200×2.1 mm), flow: 200 μL/min Temp: 60° C.

Correct product was confirmed by mass spectronomy.

Example 2—Synthesis Protocol of Alga1 (Cf. FIG. 1) by Solution Phase Cyclisation Resin loading: 200 mg (ca. 320 μmol) 2-chlorotrityl chloride in a filter equipped 5 mL-syringe are swelled with ca. 3 mL of dichloromethane for 10 min; excess solvent is removed before incubation with 40.9 mg (100 μmol) Fmoc-Glu(OH)-OtBu and 70 μL (51.9 mg, 402 μmol) DIPEA in 2 mL dichloromethane for 90 min; then capping with 10% methanol and 5% DIPEA in dichloromethane for 2×10 min; final washing with each 2×NMP, dichloromethane and diethylether followed by (short) drying on the vacuum line.

SPPS: Resin is transferred to a reaction vessel (ABI 433A), using standard FastmocUV0.05 mmol-chemistry (solvent: NMP; amino acids: each 500 μmol weighed in cartridges; HBTU-activation; base: DIPEA; deprotection: 20% piperidine) building blocks used: Fmoc-Lys(Boc)-OH, Fmoc-Arg(Pbf)-OH, Fmoc-Trp(Boc)-OH, Fmoc-His(Trt)-OH (see Example 1); final Fmoc-deprotection.

Cleavage: Product resin is transferred to a filter equipped 10 mL-syringe and swollen in dichloromethane; excess solvent is removed before incubation with 7.5 mL of 10% acetic acid and 20% trifluoroethanol in dichloromethane for 2×60 min in the stoppered syringe; trifluoroethanol and dichloromethane are removed in vacuo from the collected filtrates, acetic acid is removed by coevaporation with 2×30 mL toluene.

Cyclisation: The residue is taken up in 30 mL of DMF and 69.7 μL (50.6 mg, 500 μmol) triethylamine before 130 mg (250 μmol) PyAOP are added; reaction is carried out for 30 min after solution turns intense yellow (otherwise 250 μmol of additional triethylamine are added); reaction is quenched by addition of 50 μL of water; solvent and triethylamine are removed in high vacuo.

Deprotection: The residue of the DMF removal is directly treated with 5 mL of 2.5% water, 2.5% triisopropylsilane in TFA for 45 min; TFA is removed by 2× coevaporation with 20 mL dichloromethane; raw peptide is precipitated and washed with diethylether, collected by centrifugation and dried on the vacuum line. (ca. 100 mg).

Purification: Raw peptide is taken up in 5 mL water and heated to 45° C. for 90 min before separation on a waters XBridge BEH130Prep C18 (5 μm, 19×150 mm) column; gradient: 8-20% acetonitrile/water (0.1% TFA) in 10 min.

Yield: 42.84 mg (58.1 μmol; 58.1% based on resin loading) after lyophilisation.

The control peptide in the following Examples is N-A-A-A-E (SEQ ID NO: 37).

Example 3—a Cyclic CD44v6 5Mer (Alga1, Cf. FIG. 1) and a Cyclic CD44v6 5Mer Containing a D-Amino Acid at Position 3 (D3alga1, Cf. FIGS. 1 and 9) Block Activation of c-Met and Erk (Cf. FIG. 3)

Human adenocarcinoma cells, Panc1, were seeded at $2 \times 10^5$ cells per well in a 6-well plate. The day after seeding the cells, they were starved for 24 h. The following day, the cells were treated as indicated with either alga1 or D3alga1, a control peptide (N-A-A-A-E (SEQ ID NO: 37)) at a concentration of 30 nM for 5 min at 37° C. prior to induction with HGF (10 ng/ml) at 37° C. for 5 min. Results are given in FIG. 3 (A: alga1; B: D3alga1).

Example 4—Cyclic CD44v6 5Mers Containing a D-Amino Acid at Positions 1, 2 or 3, Respectively (D-Amino Acid at Position 1: D1alga1, at Position 2: D2alga1, at Position 3: D3alga1) Blocks Activation of c-Met and Erk (FIG. 4)

Human adenocarcinoma cells, Panc1, were seeded at $2 \times 10^5$ cells per well in a 6-well plate. The day after seeding, the cells were starved for 24 h. The following day, the cells were treated as indicated with either D1alga1, D2alga1 or D3alga1, a human CD44v6 14mer (h14mer) or control peptide (N-A-A-A-E (SEQ ID NO: 37)) at a concentration of 30 nM for 5 min at 37° C. prior to induction with HGF (10 ng/ml) at 37° C. for 5 min. Results are given in FIG. 4.

Example 5—Wound Healing Assay (Cf. FIG. 5)

A wound healing assay is used to demonstrate the blocking capacity of the tested reagents in respect of migration of cells. Cell migration is connected to angiogenesis where cells need to migrate in order to form new blood vessels. Hence, if a reagent blocks cell migration in a wound healing assay, this also strongly indicates the reagent's ability to prevent angiogenesis. FIG. 5A: Panc 1 cells were seeded in 12-well plates at a concentration of $2.5 \times 10^5$ cells per well. After 24 hours, the cells form a confluent monolayer in which a scratch is inserted using a sterile pipette tip. Medium was aspirated to remove scratched cells and replaced by new growth medium containing reagents as indicated (v6 14mer, D1alga1, D2alga1 or D3alga1) at a concentration of 30 nM tested for their blocking quality. After an incubation time of 10 min at 37° C., growth factor HGF was added to induce migration (HGF 20 ng/ml). Photos of the cells were taken 24 hours after induction using a Canon Power Shot S620 digital camera. FIG. 5B: The computer program ImageJ was used for quantitative evaluation. An area in the wound was defined and the cell invaded area was measured. The efficiency of wound closure is represented as percentage of invasion into the scratch. In particular, D3alga1 blocks cell migration most efficiently.

Example 6—Side by Side Comparison of the Human CD44v6 14Mer (V6 14MER), Alga1 and D3alga1 for their Effect on Tumor Growth Inhibition and Inhibition on Tumor Metastasis (FIG. 6)

To evaluate the inhibition of tumor growth, L3.6pl cells were orthotopically implanted into nude mice. The treatment of all animals started one week after tumor growth. The groups consisted of 8 animals, the PBS group of 6 animals. This inhibition experiment shows that the primary tumor was drastically inhibited in with a dose of 20 µg 3× weekly (cf. FIG. 6A). The reduction of the application frequency to once weekly 60 µg resulted as well in reduction of the tumor growth. All treatments were successful and significant compared to the control group (PBS 3× weekly).

To evaluate the inhibition of metastatic spreading to the liver, the groups consisted of 8 animals, the PBS group of 6 animals. With an application of 3× weekly, no macroscopic metastases were observed. Application once weekly with all compounds resulted in tumor metastasis to the liver with the ranking V6 14MER<D3alga1<alga1, and the number of metastases per animal was lower compared to the control group. "ctrl pep"=control peptide N-A-A-A-E (SEQ ID NO: 37)

Example 7—Side by Side Comparison of the Human CD44v6 14Mer (V6 14MER), Alga1 and D3alga 1 for their Effect on Regression of Already Established Metastases (FIG. 7)

L3.6pl cells were orthotopically implanted into nude mice. In contrast to Example 6 (FIG. 6), the treatment was started 3 weeks after tumor implantation; at this time all animals showed liver metastases. FIG. 7A shows inhibition of the tumor growth. The groups consisted of 8 animals, the PBS group of 6 animals. This inhibition experiment shows that the primary tumor was drastically inhibited in with a dose of 20 µg 3× weekly. The reduction of the application frequency to once weekly 60 µg resulted in reduction of the tumor growth as well. All treatments were successful and significant compared to the control group (PBS 3× weekly).

FIG. 7B depicts regression of established liver metastases. The groups consisted of 8 animals, the PBS group of 6 animals. With an application 3× weekly, no macroscopic metastases could be detected. Application once weekly with all compounds resulted in a regression of metastases with the ranking V6 14MER<D3alga1<alga1, and the number of metastases per animal was lower compared to the PBS control group. "ctrl pep"=control peptide N-A-A-A-E (SEQ ID NO: 37)

Example 8—Comparison of the Tumor Accumulation of the 14-Mer Linear Peptide and Alga1 and D3alga 1 after Labelling with $^{68}$Ga Using PET Imaging L3.6pl cells were subcutaneously implanted into nude mice. Animals were treated using $^{68}$Ga labeled forms of the 14-mer linear peptide (V6 14MER), alga1, and D3alga and PET imaging was performed 4 h after treatment. Given a similar accumulation in the kidney (FIG. 8 images on the left), it can be shown, that the tumor accumulation of the substances is increasing with the order v6 14mer<alga1<D3alga1.

Example 9—Wound Healing Assay (Cf. FIG. 15)

A wound healing assay is used to demonstrate the blocking capacity of the indicated reagents in respect of migration of cells. Cell migration is connected to angiogenesis where cells need to migrate in order to form new blood vessels. Angiogenesis is related to cancer metastasis.

Hence, if a reagent blocks cell migration in a wound healing assay, this also strongly indicates the reagent's ability to prevent angiogenesis. Panc 1 cells were seeded in 6-well plates at a concentration of 3×10$^5$ cells per well and were allowed to adhere and form a confluent monolayer. After a starving period of 24 hours, a scratch was inserted using a sterile pipette tip. Medium was aspirated to remove scratched cells and replaced by new starving medium. containing reagents as indicated at a concentration of 30 nM tested for their blocking quality.

The following reagents were added to the medium at a concentration of 500 nM to test their blocking efficiency: D3-epga1, D4-epga1, D2-epal1, D3-epal1, D4-epal1, D3-alga1, D3-alga2, D4-alga2, D5-alga2, D6-alga3, Epga-1, Epal-1, Alga-2 and Alga-3. After 30 min incubation at 37° C., growth factor HGF was added to induce migration (HGF 100 ng/ml). Photos of the cells were taken immediately after scratch (Day 1), 24 hours (Day 2) and 48 hours (D3) after induction using a Canon Power Shot G12 digital camera. As can be taken from the photo series, all tested peptides are efficient in blocking cell migration. Most efficient blocking of cell migration was observed for D2-epal1, D3-alga1, D6-alga3 and Alga-2.

Example 10—Clinical Study

Monotherapy with intravenous infusion of D2-epal1, D3-alga1, D6-alga3 and Alga-2 (cf. FIGS. 9-12) is performed. In a first step, this includes a Phase I dose escalation study on tolerability, safety and pharmacokinetics in patients with various end stage epithelial cancer types and correlative studies on CD44v6 expression. Further, the expansion cohort for preliminary efficacy in selected epithelial cancer types is tested for the aforementioned cyclic peptides. Subsequently, a multi-center (n=2-4) European study is performed.

The invention claimed is:

1. A compound comprising a cyclic peptide comprising the amino acid sequence selected from K-R-W-H-E (SEQ ID NO:34), K-N-R-W-H-E (SEQ ID NO:35), and K-G-N-R-W-H-E (SEQ ID NO:36), wherein the amino acid K is bonded to the amino acid E by a non-classical peptide bond, and wherein at least one amino acid of the cyclic peptide is a D-amino acid.

2. The compound of claim 1, wherein the cyclic peptide comprises the non-classical peptide bond selected from the group consisting of
- a peptide bond between an N-terminal amino group of K and an amino acid side chain of E,
- a peptide bond between a C-terminal carboxyl group of E and an amino acid side chain of K, and
- a peptide bond between an amino acid side chain of K of the peptide and an amino acid side chain of E of the peptide.

3. The compound of claim 2, wherein the non-classical peptide bond between the amino acid K and the amino acid E involves an amino acid side chain of at least one of the amino acid K and the amino acid E.

4. The compound of claim 1, wherein the peptide comprises the amino acid sequence K-R-W-H-E (SEQ ID NO:34) and comprises the non-classical peptide bond between an N-terminal amino group of K and a carboxyl group of an amino acid side chain of E.

5. The compound of claim 1, wherein the peptide comprises the amino acid sequence SEQ ID NO:35 and comprises the non-classical peptide bond between an N-terminal amino group of K and a carboxyl group of an amino acid side chain of E.

6. The compound of claim 1, wherein the peptide comprises the amino acid sequence SEQ ID NO:36 and comprises the non-classical peptide bond between an N-terminal amino group of K and a carboxyl group of an amino acid side chain of E.

7. The compound of claim 1, wherein the peptide comprises the amino acid sequence K-R-W-H-E (SEQ ID NO:34) and comprises the non-classical peptide bond between an amino group of an amino acid side chain of K and a C-terminal carboxyl group of E.

8. The compound of claim 1, wherein at least one amino acid of the amino acid sequence R-W-H is a D-amino acid.

9. The compound of claim 1, wherein at least W is a D-amino acid.

10. The compound of claim 1, wherein at least H is a D-amino acid.

11. The compound of claim 1, wherein at least R is a D-amino acid.

12. The compound of claim 1, wherein the peptide comprises the amino acid sequence K-R-W-H-E (SEQ ID NO:34) comprising the non-classical peptide bond between an N-terminal amino group of K and a carboxyl group of an amino acid side chain of E, wherein at least one amino acid of the amino acid sequence R-W-H is a D-amino acid.

13. The compound of claim 1, wherein the peptide comprises the amino acid sequence K-R-W-H-E (SEQ ID NO:41) and comprises the non-classical peptide bond between an N-terminal amino group of the K and a carboxyl group of an amino acid side chain of E, and wherein the amino acid W is a D-amino acid.

14. The compound of claim 1, wherein the peptide comprises the amino acid sequence SEQ ID NO:35 and comprises the non-classical peptide bond between an N-terminal amino group of K, and a carboxyl group of an amino acid side chain of E, wherein at least one amino acid is a D-amino acid.

15. The compound of claim 1, wherein the peptide comprises the amino acid sequence SEQ ID NO:36 and comprises the non-classical peptide bond between an N-terminal amino group of K, and a carboxyl group of an amino acid side chain of E, wherein the amino acid H is a D-amino acid.

16. The compound of claim 1, wherein the peptide comprises the amino acid sequence K-R-W-H-E (SEQ ID NO:42) and comprises the non-classical peptide bond between an amino group of an amino acid side chain of K, and a C-terminal carboxyl group of E, wherein the amino acid R is a D-amino acid.

17. The compound of claim 1, wherein the peptide is selected from the group consisting of
- a peptide having the amino acid sequence K-R-W-H-E (SEQ ID NO:41), comprising the non-classical peptide bond between an N-terminal amino group of K and a carboxyl group of an amino acid side chain of E, and wherein the amino acid W is a D-amino acid, a peptide having the amino acid sequence SEQ ID NO:35, comprising the non-classical peptide bond between an N-terminal amino group of K and a carboxyl group of an amino acid side chain of E, a peptide comprising the amino acid sequence SEQ ID NO:36, comprising the non-classical peptide bond between an N-terminal amino group of K and a carboxyl group of an amino acid side chain of E, wherein the amino acid H is a D-amino acid, and a peptide comprising the amino acid sequence K-R-W-H-E (SEQ ID NO:42), comprising the non-classical peptide bond between an amino group of an amino acid side chain of K and a C-terminal carboxyl group of E, wherein the amino acid R is a D-amino acid.

18. A pharmaceutical composition comprising the compound of claim 1 and a pharmaceutically acceptable carrier.

19. The compound of claim 1, wherein the compound is formulated for intravenous, oral, nasal, or subcutaneous administration.

* * * * *

SEQUENCE LISTING

```
<160> NUMBER OF SEQ ID NOS: 44

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
```

```
<220> FEATURE:
<221> NAME/KEY: MOD_RES
<222> LOCATION: (5)..(5)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr

<400> SEQUENCE: 1

Xaa Arg Trp His Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Arg Trp His Glu
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Trp His Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Lys, Arg, Gln, Ala, Val, Leu or Ile
<220> FEATURE:
<221> NAME/KEY: MOD_RES
<222> LOCATION: (5)..(5)
<223> OTHER INFORMATION: Glu, Asp, Ala, Val, Leu or Ile

<400> SEQUENCE: 4

Xaa Arg Trp His Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Lys, Arg or Gln
<220> FEATURE:
<221> NAME/KEY: MOD_RES
<222> LOCATION: (5)..(5)
<223> OTHER INFORMATION: Glu or Asp

<400> SEQUENCE: 5
```

```
Xaa Arg Trp His Xaa
1               5

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Glu Gln Trp Phe Gly Asn Arg Trp His Glu Gly Tyr Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (3)..(3)
<223> OTHER INFORMATION: Gln, Ala, Cys, Asp, Glu, Phe, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (4)..(4)
<223> OTHER INFORMATION: Trp, Ala, Cys, Asp, Glu, Phe, Gly, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (5)..(5)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (6)..(6)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (7)..(7)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
<220> FEATURE:
<221> NAME/KEY: MOD_RES
<222> LOCATION: (11)..(11)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (12)..(12)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (13)..(13)
<223> OTHER INFORMATION: Tyr, Ala, Cys, Asp, Glu, Phe, Gly, His, Ile,
      Lys, Leu, Met, Asn, Pro, Gln, Arg, Ser, Thr, Val or Trp
<220> FEATURE:
<221> NAME/KEY: MOD_RES
<222> LOCATION: (14)..(14)
```

<223> OTHER INFORMATION: Arg, Ala, Cys, Asp, Glu, Phe, Gly, His, Ile,
      Lys, Leu, Met, Asn, Pro, Gln, Ser, Thr, Val, Trp or Tyr

<400> SEQUENCE: 7

Xaa Xaa Xaa Xaa Xaa Xaa Xaa Arg Trp His Xaa Xaa Xaa Xaa
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Arg, Asn, Gln, Ala, Val, Leu or Ile
<220> FEATURE:
<221> NAME/KEY: MOD_RES
<222> LOCATION: (2)..(2)
<223> OTHER INFORMATION: Glu, Asp, Ala, Val, Leu or Ile
<220> FEATURE:
<221> NAME/KEY: MOD_RES
<222> LOCATION: (3)..(3)
<223> OTHER INFORMATION: Gln, Lys, Arg, Asn, Ala, Val, Leu or Ile
<220> FEATURE:
<221> NAME/KEY: MOD_RES
<222> LOCATION: (4)..(4)
<223> OTHER INFORMATION: Trp, Phe, Tyr, Ala, Val, Leu or Ile
<220> FEATURE:
<221> NAME/KEY: MOD_RES
<222> LOCATION: (5)..(5)
<223> OTHER INFORMATION: Phe, Trp, Tyr, Ala, Val, Leu or Ile
<220> FEATURE:
<221> NAME/KEY: MOD_RES
<222> LOCATION: (6)..(6)
<223> OTHER INFORMATION: Gly, Ala, Val, Leu or Ile
<220> FEATURE:
<221> NAME/KEY: MOD_RES
<222> LOCATION: (7)..(7)
<223> OTHER INFORMATION: Asn, Lys, Arg, Gln, Ala, Val, Leu or Ile
<220> FEATURE:
<221> NAME/KEY: MOD_RES
<222> LOCATION: (11)..(11)
<223> OTHER INFORMATION: Glu, Asp, Ala, Val, Leu or Ile
<220> FEATURE:
<221> NAME/KEY: MOD_RES
<222> LOCATION: (12)..(12)
<223> OTHER INFORMATION: Gly, Ala, Val, Leu or Ile
<220> FEATURE:
<221> NAME/KEY: MOD_RES
<222> LOCATION: (13)..(13)
<223> OTHER INFORMATION: Tyr, Phe, Trp, Ala, Val, Leu or Ile
<220> FEATURE:
<221> NAME/KEY: MOD_RES
<222> LOCATION: (14)..(14)
<223> OTHER INFORMATION: Arg, Lys, Asn, Gln, Ala, Val, Leu or Ile

<400> SEQUENCE: 8

Xaa Xaa Xaa Xaa Xaa Xaa Xaa Arg Trp His Xaa Xaa Xaa Xaa
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Arg, Asn or Gln
<220> FEATURE:

```
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: Gln, Lys, Arg or Asn
<220> FEATURE:
<221> NAME/KEY: MOD_RES
<222> LOCATION: (4)..(4)
<223> OTHER INFORMATION: Trp, Phe or Tyr
<220> FEATURE:
<221> NAME/KEY: MOD_RES
<222> LOCATION: (5)..(5)
<223> OTHER INFORMATION: Phe, Trp or Tyr
<220> FEATURE:
<221> NAME/KEY: MOD_RES
<222> LOCATION: (6)..(6)
<223> OTHER INFORMATION: Gly, Ala, Val, Leu or Ile
<220> FEATURE:
<221> NAME/KEY: MOD_RES
<222> LOCATION: (7)..(7)
<223> OTHER INFORMATION: Asn, Lys, Arg or Gln
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (12)..(12)
<223> OTHER INFORMATION: Gly, Ala, Val, Leu or Ile
<220> FEATURE:
<221> NAME/KEY: MOD_RES
<222> LOCATION: (13)..(13)
<223> OTHER INFORMATION: Tyr, Phe or Trp
<220> FEATURE:
<221> NAME/KEY: MOD_RES
<222> LOCATION: (14)..(14)
<223> OTHER INFORMATION: Arg, Lys, Asn or Gln

<400> SEQUENCE: 9

Xaa Xaa Xaa Xaa Xaa Xaa Xaa Arg Trp His Xaa Xaa Xaa Xaa
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Glu Lys Trp Phe Glu Asn Glu Trp Gln Gly Lys Asn Pro
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Glu Trp Gln Gly
1               5

<210> SEQ ID NO 12
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 12

Trp Phe Glu Asn Glu Trp Gln Gly Lys Asn Pro
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Phe Gln Asn Gly Trp Gln Gly Lys Asn Pro
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Phe Gly Asn Arg Trp His Glu Gly Tyr Arg
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Ala Ala Ala Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Gly Asn Arg Trp His Glu Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
```

```
<222> LOCATION: (2)..(2)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (3)..(3)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
<220> FEATURE:
<221> NAME/KEY: MOD_RES
<222> LOCATION: (7)..(7)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (8)..(8)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr

<400> SEQUENCE: 17

Xaa Xaa Xaa Arg Trp His Xaa Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Gly Asn Arg Trp His Glu Gly
1               5

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Asn, Arg or Gln
<220> FEATURE:
<221> NAME/KEY: MOD_RES
<222> LOCATION: (2)..(2)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (3)..(3)
<223> OTHER INFORMATION: Gln, Ala, Cys, Asp, Glu, Phe, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (4)..(4)
<223> OTHER INFORMATION: Trp, Ala, Cys, Asp, Glu, Phe, Gly, His, Ile,
      Lys, Leu, Met, Asn, Pro, Gln, Arg, Ser, Thr, Val, Trp or Tyr
<220> FEATURE:
<221> NAME/KEY: MOD_RES
<222> LOCATION: (5)..(5)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (6)..(6)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (7)..(7)
<223> OTHER INFORMATION: Asn, Ala, Cys, Asp, Glu, Phe, Gly, His, Ile,
```

Lys, Leu, Met, Pro, Gln, Arg, Ser, Thr, Val, Trp or Tyr
<220> FEATURE:
<221> NAME/KEY: MOD_RES
<222> LOCATION: (11)..(11)
<223> OTHER INFORMATION: Glu, Ala, Cys, Asp, Phe, Gly, His, Ile, Lys,
        Leu, Met, Asn, Pro, Gln, Arg, Ser, Thr, Val, Trp or Tyr
<220> FEATURE:
<221> NAME/KEY: MOD_RES
<222> LOCATION: (12)..(12)
<223> OTHER INFORMATION: Gly, Ala, Cys, Asp, Glu, Phe, His, Ile, Lys,
        Leu, Met, Asn, Pro, Gln, Arg, Ser, Thr, Val, Trp or Tyr
<220> FEATURE:
<221> NAME/KEY: MOD_RES
<222> LOCATION: (13)..(13)
<223> OTHER INFORMATION: Tyr, Ala, Cys, Asp, Glu, Phe, Gly, His, Ile,
        Lys, Leu, Met, Asn, Pro, Gln, Arg, Ser, Thr, Val or Trp
<220> FEATURE:
<221> NAME/KEY: MOD_RES
<222> LOCATION: (14)..(14)
<223> OTHER INFORMATION: Arg, Ala, Cys, Asp, Glu, Phe, Gly, His, Ile,
        Lys, Leu, Met, Asn, Pro, Gln, Ser, Thr, Val, Trp or Tyr

<400> SEQUENCE: 19

Xaa Xaa Xaa Xaa Xaa Xaa Xaa Arg Trp His Xaa Xaa Xaa Xaa
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: Lys, Asn, Gln or Arg
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: Gln, Lys, Asn, Arg, Ala, Val, Leu or Ile
<220> FEATURE:
<221> NAME/KEY: MOD_RES
<222> LOCATION: (4)..(4)
<223> OTHER INFORMATION: Trp, Ala, Phe, Ile, Leu, Val or Tyr
<220> FEATURE:
<221> NAME/KEY: MOD_RES
<222> LOCATION: (5)..(5)
<223> OTHER INFORMATION: Phe, Ala, Ile, Leu, Val, Trp or Tyr
<220> FEATURE:
<221> NAME/KEY: MOD_RES
<222> LOCATION: (6)..(6)
<223> OTHER INFORMATION: Gly, Ala, Ile, Leu or Val
<220> FEATURE:
<221> NAME/KEY: MOD_RES
<222> LOCATION: (7)..(7)
<223> OTHER INFORMATION: Asn, Gln, Arg or Lys
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (12)..(12)
<223> OTHER INFORMATION: Gly, Ala, Ile, Leu or Val
<220> FEATURE:
<221> NAME/KEY: MOD_RES
<222> LOCATION: (13)..(13)
<223> OTHER INFORMATION: Tyr, Ala, Phe, Ile, Leu, Val or Trp
<220> FEATURE:
<221> NAME/KEY: MOD_RES
<222> LOCATION: (14)..(14)
<223> OTHER INFORMATION: Arg, Lys, Gln or Asn

```
<400> SEQUENCE: 20

Xaa Xaa Xaa Xaa Xaa Xaa Xaa Arg Trp His Xaa Xaa Xaa Xaa
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Gln, Ala, Cys, Asp, Glu, Phe, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (3)..(3)
<223> OTHER INFORMATION: Trp, Ala, Cys, Asp, Glu, Phe, Gly, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (4)..(4)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (5)..(5)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (6)..(6)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
<220> FEATURE:
<221> NAME/KEY: MOD_RES
<222> LOCATION: (10)..(10)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (11)..(11)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (12)..(12)
<223> OTHER INFORMATION: Tyr, Ala, Cys, Asp, Glu, Phe, Gly, His, Ile,
      Lys, Leu, Met, Asn, Pro, Gln, Arg, Ser, Thr, Val or Trp
<220> FEATURE:
<221> NAME/KEY: MOD_RES
<222> LOCATION: (13)..(13)
<223> OTHER INFORMATION: Arg, Ala, Cys, Asp, Glu, Phe, Gly, His, Ile,
      Lys, Leu, Met, Asn, Pro, Gln, Ser, Thr, Val, Trp or Tyr

<400> SEQUENCE: 21

Xaa Xaa Xaa Xaa Xaa Xaa Arg Trp His Xaa Xaa Xaa Xaa
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Trp, Ala, Cys, Asp, Glu, Phe, Gly, His, Ile,
      Lys, Leu, Met, Asn, Pro, Arg, Ser, Thr, Val or Tyr
<220> FEATURE:
<221> NAME/KEY: MOD_RES
<222> LOCATION: (3)..(3)
<223> OTHER INFORMATION: Phe, Ala, Cys, Asp, Glu, Trp, Gly, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (4)..(4)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (5)..(5)
<223> OTHER INFORMATION: Asn, Ala, Cys, Asp, Glu, Phe, His, Ile, Lys,
      Leu, Met, Gly, Pro, Gln, Arg, Ser, Thr, Val, Trp or Tyr
<220> FEATURE:
<221> NAME/KEY: MOD_RES
<222> LOCATION: (9)..(9)
<223> OTHER INFORMATION: Glu, Ala, Cys, Asp, Gly, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (10)..(10)
<223> OTHER INFORMATION: Gly, Ala, Cys, Asp, Glu, Phe, Tyr, His, Ile,
      Lys, Leu, Met, Asn, Pro, Gln, Arg, Ser, Thr, Val or Trp
<220> FEATURE:
<221> NAME/KEY: MOD_RES
<222> LOCATION: (11)..(11)
<223> OTHER INFORMATION: Tyr, Ala, Cys, Asp, Glu, Phe, Gly, His, Ile,
      Lys, Leu, Met, Asn, Pro, Gln, Ser, Thr, Val or Trp

<400> SEQUENCE: 22

Xaa Xaa Xaa Xaa Xaa Arg Trp His Xaa Xaa Xaa Arg
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Phe, Ala, Cys, Asp, Glu, Gln, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (3)..(3)
<223> OTHER INFORMATION: Gly, Ala, Cys, Asp, Glu, Phe, Trp, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (4)..(4)
<223> OTHER INFORMATION: Asn, Ala, Cys, Asp, Glu, Gly, His, Ile, Lys,
      Leu, Met, Phe, Pro, Gln, Arg, Ser, Thr, Val, Trp or Tyr
<220> FEATURE:
<221> NAME/KEY: MOD_RES
<222> LOCATION: (8)..(8)
<223> OTHER INFORMATION: Glu, Ala, Cys, Asp, Gly, Phe, His, Ile, Lys,
      Leu, Met, Asn, Pro, Gln, Arg, Ser, Thr, Val, Trp or Tyr
<220> FEATURE:
```

```
<221> NAME/KEY: MOD_RES
<222> LOCATION: (9)..(9)
<223> OTHER INFORMATION: Gly, Ala, Cys, Asp, Glu, Phe, Asn, His, Ile,
      Lys, Leu, Met, Pro, Gln, Arg, Ser, Thr, Val, Trp or Tyr
<220> FEATURE:
<221> NAME/KEY: MOD_RES
<222> LOCATION: (10)..(10)
<223> OTHER INFORMATION: Tyr, Ala, Cys, Asp, Phe, Gly, His, Ile, Lys,
      Leu, Met, Asn, Pro, Gln, Arg, Ser, Thr, Val or Trp
<220> FEATURE:
<221> NAME/KEY: MOD_RES
<222> LOCATION: (11)..(11)
<223> OTHER INFORMATION: Arg, Ala, Cys, Asp, Glu, Phe, His, Ile, Lys,
      Leu, Met, Asn, Pro, Gln, Gly, Ser, Thr, Val, Trp or Tyr

<400> SEQUENCE: 23

Xaa Xaa Xaa Xaa Arg Trp His Xaa Xaa Xaa Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Gly, Ala, Cys, Asp, Glu, Phe, Gln, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (3)..(3)
<223> OTHER INFORMATION: Asn, Ala, Cys, Asp, Glu, Phe, Gly, His, Ile,
      Lys, Leu, Met, Trp, Pro, Gln, Arg, Ser, Thr, Val or Tyr
<220> FEATURE:
<221> NAME/KEY: MOD_RES
<222> LOCATION: (7)..(7)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (8)..(8)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (9)..(9)
<223> OTHER INFORMATION: Tyr, Ala, Cys, Asp, Glu, Phe, Gly, His, Ile,
      Lys, Leu, Met, Pro, Gln, Arg, Ser, Thr, Val, Trp or Asn
<220> FEATURE:
<221> NAME/KEY: MOD_RES
<222> LOCATION: (10)..(10)
<223> OTHER INFORMATION: Arg Ala, Cys, Asp, Phe, Gly, His, Ile, Lys,
      Leu, Met, Asn, Pro, Gln, Glu, Ser, Thr, Val, Trp or Tyr

<400> SEQUENCE: 24

Xaa Xaa Xaa Arg Trp His Xaa Xaa Xaa Xaa
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

-continued

```
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Asn, Ala, Cys, Asp, Glu, Phe, Gly, His, Ile,
      Lys, Leu, Met, Gln, Pro, Arg, Ser, Thr, Val, Trp or Tyr
<220> FEATURE:
<221> NAME/KEY: MOD_RES
<222> LOCATION: (6)..(6)
<223> OTHER INFORMATION: Glu, Ala, Cys, Asp, Trp, Phe, Gly, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (7)..(7)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (8)..(8)
<223> OTHER INFORMATION: Tyr, Ala, Cys, Asp, Glu, Phe, His, Ile, Lys,
      Leu, Met, Asn, Pro, Gln, Arg, Ser, Thr, Val, Trp or Gly
<220> FEATURE:
<221> NAME/KEY: MOD_RES
<222> LOCATION: (9)..(9)
<223> OTHER INFORMATION: Arg, Ala, Cys, Asp, Glu, Phe, Gly, His, Ile,
      Lys, Leu, Met, Pro, Gln, Asn, Ser, Thr, Val, Trp or Tyr

<400> SEQUENCE: 25

Xaa Xaa Arg Trp His Xaa Xaa Xaa Xaa
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (5)..(5)
<223> OTHER INFORMATION: Glu, Ala, Cys, Asp, Gln, Phe, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (6)..(6)
<223> OTHER INFORMATION: Gly, Ala, Cys, Asp, Glu, Phe, Trp, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (7)..(7)
<223> OTHER INFORMATION: Tyr, Ala, Cys, Asp, Glu, Gly, His, Ile, Lys,
      Leu, Met, Asn, Pro, Gln, Arg, Ser, Thr, Val, Trp or Phe
<220> FEATURE:
<221> NAME/KEY: MOD_RES
<222> LOCATION: (8)..(8)
<223> OTHER INFORMATION: Arg Ala, Cys, Asp, Glu, Phe, His, Ile, Lys,
      Leu, Met, Asn, Pro, Gln, Gly, Ser, Thr, Val, Trp or Tyr

<400> SEQUENCE: 26

Xaa Arg Trp His Xaa Xaa Xaa Xaa
1               5

<210> SEQ ID NO 27
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Asn, Gln or Arg
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: Gln, Lys, Asn, Arg, Ala, Val, Leu or Ile
<220> FEATURE:
<221> NAME/KEY: MOD_RES
<222> LOCATION: (4)..(4)
<223> OTHER INFORMATION: Trp, Ala, Phe, Ile, Leu, Val or Tyr
<220> FEATURE:
<221> NAME/KEY: MOD_RES
<222> LOCATION: (5)..(5)
<223> OTHER INFORMATION: Phe, Ala, Ile, Leu, Val, Trp or Tyr
<220> FEATURE:
<221> NAME/KEY: MOD_RES
<222> LOCATION: (6)..(6)
<223> OTHER INFORMATION: Gly, Ala, Ile, Leu or Val
<220> FEATURE:
<221> NAME/KEY: MOD_RES
<222> LOCATION: (7)..(7)
<223> OTHER INFORMATION: Asn, Gln, Arg or Lys
<220> FEATURE:
<221> NAME/KEY: MOD_RES
<222> LOCATION: (11)..(11)
<223> OTHER INFORMATION: Glu or Asp

<400> SEQUENCE: 27

Xaa Xaa Xaa Xaa Xaa Xaa Xaa Arg Trp His Xaa
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Asn, Gln or Arg
<220> FEATURE:
<221> NAME/KEY: MOD_RES
<222> LOCATION: (2)..(2)
<223> OTHER INFORMATION: Gln, Ala, Cys, Asp, Glu, Phe, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (3)..(3)
<223> OTHER INFORMATION: Trp, Ala, Cys, Asp, Glu, Phe, Gly, His, Ile,
      Lys, Leu, Met, Asn, Pro, Gln, Arg, Thr, Val or Tyr
<220> FEATURE:
<221> NAME/KEY: MOD_RES
<222> LOCATION: (4)..(4)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (5)..(5)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (6)..(6)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
<220> FEATURE:
<221> NAME/KEY: MOD_RES
```

```
<222> LOCATION: (10)..(10)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr

<400> SEQUENCE: 28

Xaa Xaa Xaa Xaa Xaa Xaa Arg Trp His Xaa
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Asn, Gln or Arg
<220> FEATURE:
<221> NAME/KEY: MOD_RES
<222> LOCATION: (2)..(2)
<223> OTHER INFORMATION: Trp, Ala, Cys, Asp, Glu, Phe, Gly, His, Ile,
      Lys, Leu, Met, Asn, Pro, Arg, Ser, Thr, Val, Gln or Tyr
<220> FEATURE:
<221> NAME/KEY: MOD_RES
<222> LOCATION: (3)..(3)
<223> OTHER INFORMATION: Phe, Ala, Cys, Asp, Glu, Trp, Gly, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (4)..(4)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (5)..(5)
<223> OTHER INFORMATION: Asn, Ala, Cys, Asp, Glu, Phe, His, Ile, Lys,
      Leu, Met, Gly, Pro, Gln, Arg, Ser, Thr, Val, Trp or Tyr
<220> FEATURE:
<221> NAME/KEY: MOD_RES
<222> LOCATION: (9)..(9)
<223> OTHER INFORMATION: Glu, Ala, Cys, Asp, Gly, Phe, His, Ile, Lys,
      Leu, Met, Asn, Pro, Gln, Arg, Ser, Thr, Val, Trp or Tyr

<400> SEQUENCE: 29

Xaa Xaa Xaa Xaa Xaa Arg Trp His Xaa
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Asn, Gln or Arg
<220> FEATURE:
<221> NAME/KEY: MOD_RES
<222> LOCATION: (2)..(2)
<223> OTHER INFORMATION: Phe, Ala, Cys, Asp, Glu, Gln, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (3)..(3)
<223> OTHER INFORMATION: Gly, Ala, Cys, Asp, Glu, Phe, Trp, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (4)..(4)
<223> OTHER INFORMATION: Asn, Ala, Cys, Asp, Glu, Gly, His, Ile, Lys,
      Leu, Met, Phe, Pro, Gln, Arg, Ser, Thr, Val, Trp or Tyr
```

```
<220> FEATURE:
<221> NAME/KEY: MOD_RES
<222> LOCATION: (8)..(8)
<223> OTHER INFORMATION: Glu, Ala, Cys, Asp, Gly, Phe, His, Ile, Lys,
      Leu, Met, Asn, Pro, Gln, Arg, Ser, Thr, Val, Trp or Tyr

<400> SEQUENCE: 30

Xaa Xaa Xaa Xaa Arg Trp His Xaa
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Gly, Ala, Cys, Asp, Glu, Phe, Gln, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (3)..(3)
<223> OTHER INFORMATION: Asn, Ala, Cys, Asp, Glu, Phe, Gly, His, Ile,
      Lys, Leu, Met, Trp, Pro, Gln, Arg, Ser, Thr, Val or Tyr
<220> FEATURE:
<221> NAME/KEY: MOD_RES
<222> LOCATION: (7)..(7)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr

<400> SEQUENCE: 31

Xaa Xaa Xaa Arg Trp His Xaa
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Asn, Ala, Cys, Asp, Glu, Phe, Gly, His, Ile,
      Lys, Leu, Met, Gln, Pro, Arg, Ser, Thr, Val, Trp or Tyr
<220> FEATURE:
<221> NAME/KEY: MOD_RES
<222> LOCATION: (6)..(6)
<223> OTHER INFORMATION: Glu, Ala, Cys, Asp, Trp, Phe, Gly, His, Ile,
      Lys, Leu, Met, Asn, Pro, Gln, Arg, Ser, Thr, Val or Tyr

<400> SEQUENCE: 32

Xaa Xaa Arg Trp His Xaa
1               5

<210> SEQ ID NO 33
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (5)..(5)
<223> OTHER INFORMATION: Glu, Ala, Cys, Asp, Gln, Phe, Gly, His, Ile,
      Lys, Leu, Met, Asn, Pro, Arg, Ser, Thr, Val, Trp or Tyr

<400> SEQUENCE: 33

Xaa Arg Trp His Xaa
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 34

Lys Arg Trp His Glu
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 35

Lys Asn Arg Trp His Glu
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 36

Lys Gly Asn Arg Trp His Glu
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 37

Asn Ala Ala Ala Glu
1               5

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (3)..(3)
<223> OTHER INFORMATION: Gln, Ala, Cys, Asp, Glu, Phe, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (4)..(4)
<223> OTHER INFORMATION: Trp, Ala, Cys, Asp, Glu, Phe, Gly, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (5)..(5)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (6)..(6)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (7)..(7)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
<220> FEATURE:
<221> NAME/KEY: MOD_RES
<222> LOCATION: (11)..(11)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (12)..(12)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (13)..(13)
<223> OTHER INFORMATION: Tyr, Ala, Cys, Asp, Glu, Phe, Gly, His, Ile,
      Lys, Leu, Met, Asn, Pro, Gln, Arg, Ser, Thr, Val, Trp or Tyr

<400> SEQUENCE: 38

Xaa Xaa Xaa Xaa Xaa Xaa Xaa Arg Trp His Xaa Xaa Xaa
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (3)..(3)
<223> OTHER INFORMATION: Gln, Ala, Cys, Asp, Glu, Phe, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (4)..(4)
<223> OTHER INFORMATION: Trp, Ala, Cys, Asp, Glu, Phe, Gly, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (5)..(5)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (6)..(6)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (7)..(7)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr r
<220> FEATURE:
<221> NAME/KEY: MOD_RES
<222> LOCATION: (11)..(11)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (12)..(12)
<223> OTHER INFORMATION: Gly Ala, Cys, Asp, Glu, Phe, His, Ile, Lys,
      Leu, Met, Asn, Pro, Gln, Arg, Ser, Thr, Val, Trp or Tyr

<400> SEQUENCE: 39

Xaa Xaa Xaa Xaa Xaa Xaa Xaa Arg Trp His Xaa Xaa
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (3)..(3)
<223> OTHER INFORMATION: Gln, Ala, Cys, Asp, Glu, Phe, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (4)..(4)
<223> OTHER INFORMATION: Trp, Ala, Cys, Asp, Glu, Phe, Gly, His, Ile,
      Lys, Leu, Met, Asn, Pro, Gln, Arg, Ser, Thr, Val or Tyr
<220> FEATURE:
<221> NAME/KEY: MOD_RES
```

```
<222> LOCATION: (5)..(5)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (6)..(6)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (7)..(7)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
<220> FEATURE:
<221> NAME/KEY: MOD_RES
<222> LOCATION: (11)..(11)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr

<400> SEQUENCE: 40

Xaa Xaa Xaa Xaa Xaa Xaa Xaa Arg Trp His Xaa
1               5                   10

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Trp
<220> FEATURE:
<223> OTHER INFORMATION: See specification as filed for detailed
      description of substitutions and preferred embodiments

<400> SEQUENCE: 41

Lys Arg Trp His Glu
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Arg
<220> FEATURE:
<223> OTHER INFORMATION: See specification as filed for detailed
      description of substitutions and preferred embodiments

<400> SEQUENCE: 42

Lys Arg Trp His Glu
1               5

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 43
```

```
Lys Arg Trp His
1

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Aminobutyric acid
<220> FEATURE:
<223> OTHER INFORMATION: See specification as filed for detailed
      description of substitutions and preferred embodiments

<400> SEQUENCE: 44

Lys Arg Trp His Xaa
1               5
```